US006265158B1

(12) United States Patent
Shiloh

(10) Patent No.: US 6,265,158 B1
(45) Date of Patent: *Jul. 24, 2001

(54) ATAXIA-TELANGIECTASIA GENE AND ITS GENOMIC ORGANIZATION

(75) Inventor: Yosef Shiloh, Tel Aviv (IL)

(73) Assignee: Ramot-University Authority for Applied Research and Industrial Development, Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 08/952,014

(22) PCT Filed: May 16, 1996

(86) PCT No.: PCT/US96/07025

§ 371 Date: Feb. 2, 1998

§ 102(e) Date: Feb. 2, 1998

(87) PCT Pub. No.: WO96/36691

PCT Pub. Date: Nov. 21, 1996

Related U.S. Application Data

(63) Continuation-in-part of application No. 08/629,001, filed on Apr. 8, 1996, now Pat. No. 5,858,661, which is a continuation-in-part of application No. 08/441,822, filed on May 16, 1995, now Pat. No. 5,756,288.

(51) Int. Cl.[7] .............................. C12Q 1/68; C07H 21/04
(52) U.S. Cl. ........................... 435/6; 536/23.1; 536/24.3; 536/24.31
(58) Field of Search ................................ 435/6; 536/23.1, 536/24.3, 24.31

(56) References Cited

U.S. PATENT DOCUMENTS

| 5,175,383 | 12/1992 | Leder et al. | 800/2 |
|---|---|---|---|
| 5,395,767 | 3/1995 | Murnane et al. | 435/320.3 |
| 5,756,288 * | 5/1998 | Shiloh | 435/6 |
| 5,858,661 * | 1/1999 | Shiloh | 435/6 |

FOREIGN PATENT DOCUMENTS

| WO 9400572 | 1/1994 | (WO) | C12N/15/12 |
|---|---|---|---|
| WO 9503431 | 2/1995 | (WO) | C12Q/1/68 |

OTHER PUBLICATIONS

Rasio et al "Genomic Organization of the ATM Locus involved in Ataxia–Telangiectasia" Cancer Research. vol. 55, pp. 6053–6057, Dec. 1995.*

Uziel et al "Genomic Organization of the ATM gene" Genomic. vol. 33, Apr. 1996, pp. 317–320.*

Kapp, "Cloning of a candidate gene for Ataxia–Telangiectasia Group D" *Am. J. Hum. Genet.,* 51:45–54 (1992).

Leonardt et al., "Nucleotide sequence analysis of a candidate gene for Ataxia–Telangiectasia Group D (ATDC)" *Genomics,* 19:130–136 (1994).

Akentijevitch et al. "Familial mediterranean fever in Moroccan Jews: demonstration of a founder effect by extended haplotype analysis" *Am. J. Hum. Genet.,* 53:644–651 (1993).

Ambrose et al., "A physical map across chromosome 11q22–23 containing the major locus for ataxia–telangiectasia" *Genomics,* 21:612–619 (1994).

Attree et al., "The Lowe's oculocerebrorenal syndrome gene encodes a protein highly homologous to inositol . . . " *Nature,* 358:239–242 (1992).

Beamish and Lavin, "Radiosensitivity in ataxia–telangiectasia: anomalies in radiation–induced cell cycle delay" *J. Radiat. Biol.,* 65:175–184.

Berger et al., "Isolation of a candidate gene for Norrie disease by positional cloning" *Nature Genet.* 1:199–203 (1992).

Buckler et al., "Exon amplification: a strategy to isolate mammalian genes used on RNA splicing" *Proc. Natl. Acad. Sci. USA,* 88:4005–4009 (1991).

Chakravarti et al., "Nonuniform recombination within the human beta–globin gene cluster" *Am. J. Hum. Genet.,* 36:1239–1258 (1984).

Chelly et al., "Isolation of a candidate gene for Menkes disease that encodes a potential heavy metal binding protein" *Nature Genet.,* 3:14–19 (1993).

Church et al., "Isolation of genes from complex sources of mammalian genomic DNA using exon amplification" *Nature Genet.,* 6:98–104 (1993).

Collins, "Positional cloning: let's not call it reverse anymore" *Nature Genet.,* 1:3–6 (1992).

Duyk et al., "Exon trapping: a genetic screen to identify candidate transcribed sequences in cloned mammalian genomic DNA" *Proc. Natl. Acad. Sci. USA,* 87:8995–8999 (1990).

Foroud et al., "Localization of the AT locus to an 8 cM interval defined by STMY and S132" *Am. J. Hum. Genet.,* 49:1263–1279 (1991).

Frohman, *PCR Methods and Applications,* 4:S40–S58 (1994).

Frohman et al., *Proc. Natl. Sci. USA,* 85:8998–9002 (1988).

Gatti et al., "Genetic haplotyping of ataxia–telangiectasia families localizes the major gene to an 850 kb region on chromosome . . . " *Int. J. Radiat. Biol.,* (in press) (1994).

Gatti et al., "Localization of an ataxia–telangiectasia gene to chromosome 11q22–23" *Nature,* 336:577–580 (1988).

Hastbacka et al., "Linkage disequilibrium mapping in isolated founder populations: diastrophic dysplasia in Finland" *Nature Genet.,* 2:204–211 (1992).

(List continued on next page.)

Primary Examiner—W. Gary Jones
Assistant Examiner—Jeanine Goldberg
(74) *Attorney, Agent, or Firm*—Kohn & Associates

(57) ABSTRACT

A purified and isolated gene, designated ATM, mutations of which cause ataxia-telangiectasia, its genomic organization, methods for the detection of the defective gene, the purified polypeptide encoded by the defective gene, and antibodies recognizing the defective protein.

7 Claims, 2 Drawing Sheets

OTHER PUBLICATIONS

Heim et al., "Heterozygous manifestations in four autosomal recessive human cancer–prone syndromes . . . " *Mutat. Res.,* 284:25–36 (1992).

Kastan et al., "A mammalian cell cycle checkpoint pathway utilizing p53 and GADD45 is defective in ataxia–telangiectasia" *Cell,* 71:587–597.

Kerem et al., "Identification of the cystic fibrosis gene: genetic analysis" *Science,* 245:1073–1080 (1989).

Khanna and Lavin, "Ionizing radiation and UV induction of p53 protein by different pathways in ataxia–telangiectasia cells" *Oncogene,* 8:3307–3312 (1993).

Lange et al., "Localization of an ataxia–telangiectasia gene to a 850 kb interval on chromosome 11q23.1 by linkage . . . " (submitted) (1994).

Lehesjoki et al., Localization of the EPM1 gene for progressive myoclonus epilepsy on chromosome 21: linkage disequilibrium . . . *Hum. Mol. Genet.,* 2:1229–1234 (1993).

Litt and Luty, "A hypervariable microsatellite revealed by in vitro amplification of a dinucleotide repeat within the cardiac muscle . . . " *Am. J. Hum. Genet.,* 44:397–401 (1989).

Llerena et al., "Spontaneous and induced chromosome breakage in chorionic villus samples . . . " *J. Med. Genet.,* 26:174–178 (1989).

McConville et al., "Genetic and physical mapping of the ataxia–telangiectasia locus on chromosome 11q22–23" *Int. J. Radiat. Biol.* (1994).

McConville et al., *Hum. Mol. Genet.,* 2:969–974 (1993).

McConville et al., *Nucleic Acids, Res.,* 18:4335–4343 (1990).

Miki et al., "A strong candidate for the breast and ovarian cancer susceptibility gene BRCA1" *Science,* 266:66–71 (1994).

Mitchison et al., "Fine genetic mapping of the Batten Disease locus (CLN3) by haplotype analysis and demonstration . . . " *Genomics,* 16:455–460 (1993).

Morgan et al., "The selective isolation of novel cDNAs encoded by the regions surrounding the human interleukin 4 and 5 genes" *Nucleic Acids Res.,* 20:5173–5179 (1992).

Oskato et al., "Ataxia–telangiectasia: allelic association with 11q22–23 markers in Moroccan–Jewish patients" *43rd Annual Meeting of the American Society of Human Genetics,* New Orleans, LA (1993).

Ozelius et al., "Strong allelic association between the torsion dystonia gene (DYT1) and loci on chromosome . . . " *Am. J. Hum. Genet.,* 50:619–628 (1992).

Parimoo et al., "cDNA selection: efficient PCR approach for the selection of cDNAs encoded in large chromosomal DNA fragments" *Proc. Natl. Acad. Sci. USA,* 88:9623–9627 (1991).

Rotman et al., "Rapid identification of polymorphic CA–repeats in YAC clones" *Molecular Biotechnology* (in press) (1994a).

Rotman et al., "Three dinucleotide repeat polymorphisms at the ataxia–telangiectasia locus" *Human Molecular Genetics* (in press) (1994b).

Rotman et al., "A YAC contig spanning the ataxia–telangiectasia locus (groups A and C) on chromosome 11q22–23" *Genomics* (in press) (1994c).

Rotman et al., "Physical and genetic mapping of the ATA/ATC locus in chromosome 11q22–23" *Int. J. Radiat. Biol.* (in press) (1994d).

Savitsky et al., "A single gene with homologies to phosphatidylinositol 3–kinases and rad3+ is mutated in all . . . " (submitted for publication). (no year).

Sirugo et al., "Friedreich ataxia in Louisiana Acadians: demonstration of a founder effect by analysis . . . " *Am. J. Hum. Genet.,* 50:559–566 (1992).

Shiloh, "Ataxia–telangiectasia: closer to unraveling the mystery" *European Journal of Human Genetics* (in press) (no year).

Shiloh et al., "Carrier detection in ataxia–telangiectasia" *The Lancet,* I:689 (1986).

Swift et al., "Cancer predisposition of ataxia–telangiectasia heterozygotes" *Cancer Genet. Cytogenet.,* 46:21–27 (1990).

Swift et al., "Incidence of cancer in 1616 families affected by ataxia–telangiectasia" *New Engl. J. Med.,* 325:1831–1836 (1991).

Tagle et al., "Magnetic bead capture of expressed sequences encoded within large genomic segments" *Nature,* 361:751–753 (1993).

The European Polycystic Kidney Disease Consortium, "The polycystic kidney disease 1 gene encodes a 14 kb transcript . . . " *Cell,* 77:881–894 (1994).

The Hungington's Disease Collaborative Research Group, "A novel gene containing a trinucleotide repeat that is expanded . . . " *Cell,* 72:971–983 (1993).

Trofatter et al., "A novel moesin–, ezrin–, radixin–like gene is a candidate for the neurofibromatosis 2 tumor suppressor" *Cell,* 72:791–800 (1993).

Vanagaite et al., "Physical localization of microsatellite markers at the ataxia–telangiectasia locus at 11q22–23" *Genomics,* 22:231–233 (1994a).

Vanagaite et al., "A high–density microsatellite map of the ataxia–telangiectasia locus" *Human Genetics* (in press) (1994b).

Vetrie et al., "The gene involved in X–linked agammaglobulinemia is a member of the src family of protein–tyrosine kinases" *Nature,* 361:226–233 (1993).

Weber and May, "Abundant class of human DNA polymorphisms which can be typed using the polymerase chain reaction" *Am. J. Hum. Genet.,* 44:388–396 (1989).

Ziv et al., "Ataxia–telangiectasia: linkage analysis in highly inbred Arab and Druze families and differentiation . . . " *Hum. Genet.,* 88:619–626 (1992).

Ziv et al., "The ATC (ataxia–telangiectasia complementation group C) locus localizes to 11q22–q23" *Genomics,* 9:373–375 (1991).

Porter et al., "A novel selection system for recombinational and mutational events within an intron of a eucaryotic gene" *Nucleic Acids Research,* vol. 18, No. 17, pp. 5173–5179 (1990).

Burke and Olson, "Preparation of Clone Libraries in Yeast Artificial–Chromosome Vectors" in *Methods in Enzymology,* vol. 194, "Guide to Yeast Genetics and Molecular Biology", eds. C. Guthrie and G. Fink, Academic Press, Inc., Chap. 17, pp. 251–270 (1991).

Byrne et al., "Ataxia–without–telangiectasia" *J Neurol. Sci.* 66:307–317 (1984).

Gilad et al., *Hum. Mol. Genet.* 5:433–439 (1996).

Gilboa et al. "Transfer and expression of cloned genes using retroviral vectors" *BioTechniques* 4(6):504–512 (1986).

Kawasakies. Amplification of RNA. In: PCR protocols: A Guide to Methods and Applications, Innis MA, Gelfand DH, Sninsky JJ, White TJ, eds. Academic Press, 1990, pp 21–27.

Kozak et al., "An analysis of 5'-noncoding sequences from 699 vertebrate messenger RNAs" *Nucleic Acids Res.,* 15:8125–8148 (1987). [n/a—will mail in].

Shiloh et al., *Am. J. Hum. Genet.* 55 (suppl.), A49 (1994a) [n/a—will mail in].

Shiloh, et al., 1994b. Genetic, physical and functional analysis of the ataxia–telangiectasia locus on chromosome 11q22–23. 44th Annual Meeting of the American Society of Human Genetics, Montreal. Am. J. Hum. Genet. 55:A49. [n/a—will mail in].

* cited by examiner

SEQUENCE LISTING (1) GENERAL INFORMATION:

(iii) NUMBER OF SEQUENCES: 91

(2) INFORMATION FOR SEQ ID NO:1:

(i) SEQUENCE CHARACTERISTICS:
      (A) LENGTH: 5912 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (B) CLONE: 7-9

(xi) SEQUENCE DESCRIPTION: SEQ ID NO:1:

```
CATACTTTTT CCTCTTAGTC TACAGGTTGG CTGCATAGAA GAAAAAGGTA GAGTTATTTA     60

TAATCTTGTA AATCTTGGAC TTTGAGTCAT CTATTTTCTT TTACAGTCAT CGAATACTTT    120

TGGAAATAAG GTAATATATG CCTTTTGAGC TGTCTTGACG TTCACAGATA TAAAATATTA    180

AATATATTTT AATTTTGTGC CCTTGCAGAT TGATCACTTA TTCATTAGTA ATTTACCAGA    240

GATTGTGGTG GAGTTATTGA TGACGTTACA TGAGCCAGCA AATTCTAGTG CCAGTCAGAG    300

CACTGACCTC TGTGACTTTT CAGGGGATTT GGATCCTGCT CCTAATCCAC CTCATTTTCC    360

ATCGCATGTG ATTAAAGCAA CATTTGCCTA TATCAGCAAT TGTCATAAAA CCAAGTTAAA    420

AAGCATTTTA GAAATTCTTT CCAAAAGCCC TGATTCCTAT CAGAAAATTC TTCTTGCCAT    480

ATGTGAGCAA GCAGCTGAAA CAAATAATGT TTATAAGAAG CACAGAATTC TTAAAATATA    540

TCACCTGTTT GTTAGTTTAT TACTGAAAGA TATAAAAAGT GGCTTAGGAG GAGCTTGGGC    600

CTTTGTTCTT CGAGACGTTA TTTATACTTT GATTCACTAT ATCAACCAAA GGCCTTCTTG    660

TATCATGGAT GTGTCATTAC GTAGCTTCTC CCTTTGTTGT GACTTATTAA GTCAGGTTTG    720

CCAGACAGCC GTGACTTACT GTAAGGATGC TCTAGAAAAC CATCTTCATG TTATTGTTGG    780
```

-continued

```
TACACTTATA CCCCTTGTGT ATGAGCAGGT GGAGGTTCAG AAACAGGTAT TGGACTTGTT      840
GAAATACTTA GTGATAGATA ACAAGGATAA TGAAAACCTC TATATCACGA TTAAGCTTTT      900
AGATCCTTTT CCTGACCATG TTGTTTTTAA GGATTTGCGT ATTACTCAGC AAAAAATCAA      960
ATACAGTAGA GGACCCTTTT CACTCTTGGA GGAAATTAAC CATTTTCTCT CAGTAAGTGT     1020
TTATGATGCA CTTCCATTGA CAAGACTTGA AGGACTAAAG GATCTTCGAA GACAACTGGA     1080
ACTACATAAA GATCAGATGG TGGACATTAT GAGAGCTTCT CAGGATAATC CGCAAGATGG     1140
GATTATGGTG AAACTAGTTG TCAATTTGTT GCAGTTATCC AAGATGGCAA TAAACCACAC     1200
TGGTGAAAAA GAAGTTCTAG AGGCTGTTGG AAGCTGCTTG GGAGAAGTGG GTCCTATAGA     1260
TTTCTCTACC ATAGCTATAC AACATAGTAA AGATGCATCT TATACCAAGG CCCTTAAGTT     1320
ATTTGAAGAT AAAGAACTTC AGTGGACCTT CATAATGCTG ACCTACCTGA ATAACACACT     1380
GGTAGAAGAT TGTGTCAAAG TTCGATCAGC AGCTGTTACC TGTTTGAAAA ACATTTTAGC     1440
CACAAAGACT GGACATAGTT TCTGGGAGAT TTATAAGATG ACAACAGATC CAATGCTGGC     1500
CTATCTACAG CCTTTTAGAA CATCAAGAAA AAAGTTTTTA GAAGTACCCA GATTTGACAA     1560
AGAAAACCCT TTTGAAGGCC TGGATGATAT AAATCTGTGG ATTCCTCTAA GTGAAAATCA     1620
TGACATTTGG ATAAAGACAC TGACTTGTGC TTTTTTGGAC AGTGGAGGCA CAAAATGTGA     1680
AATTCTTCAA TTATTAAAGC CAATGTGTGA AGTGAAAACT GACTTTGTC AGACTGTACT      1740
TCCATACTTG ATTCATGATA TTTTACTCCA AGATACAAAT GAATCATGGA GAAATCTGCT     1800
TTCTACACAT GTTCAGGGAT TTTTCACCAG CTGTCTTCGA CACTTCTCGC AAACGAGCCG     1860
ATCCACAACC CCTGCAAACT TGGATTCAGA GTCAGAGCAC TTTTTCCGAT GCTGTTTGGA     1920
TAAAAAATCA CAAAGAACAA TGCTTGCTGT TGTGGACTAC ATGAGAAGAC AAAAGAGACC     1980
TTCTTCAGGA ACAATTTTTA ATGATGCTTT CTGGCTGGAT TTAAATTATC TAGAAGTTGC     2040
CAAGGTAGCT CAGTCTTGTG CTGCTCACTT TACAGCTTTA CTCTATGCAG AAATCTATGC     2100
AGATAAGAAA AGTATGGATG ATCAAGAGAA AAGAAGTCTT GCATTTGAAG AAGGAAGCCA     2160
GAGTACAACT ATTTCTAGCT TGAGTGAAAA AAGTAAAGAA GAAACTGGAA TAAGTTTACA     2220
GGATCTTCTC TTAGAAATCT ACAGAAGTAT AGGGGAGCCA GATAGTTTGT ATGGCTGTGG     2280
TGGAGGGAAG ATGTTACAAC CCATTACTAG ACTACGAACA TATGAACACG AAGCAATGTG     2340
GGGCAAAGCC CTAGTAACAT ATGACCTCGA ACAGCAATC CCCTCATCAA CACGCCAGGC      2400
AGGAATCATT CAGGCCTTGC AGAATTTGGG ACTCTGCCAT ATTCTTTCCG TCTATTTAAA     2460
AGGATTGGAT TATGAAAATA AAGACTGGTG TCCTGAACTA AAGAACTTC ATTACCAAGC      2520
AGCATGGAGG AATATGCAGT GGGACCATTG CACTTCCGTC AGCAAAGAAG TAGAAGGAAC     2580
CAGTTACCAT GAATCATTGT ACAATGCTCT ACAATCTCTA AGAGACAGAG AATTCTCTAC     2640
ATTTTATGAA AGTCTCAAAT ATGCCAGAGT AAAAGAAGTG GAAGAGATGT GTAAGCGCAG     2700
CCTTGAGTCT GTGTATTCGC TCTATCCCAC ACTTAGCAGG TTGCAGGCCA TTGGAGAGCT     2760
GGAAAGCATT GGGGAGCTTT TCTCAAGATC AGTCACACAT AGACAACTCT CTGAAGTATA     2820
TATTAAGTGG CAGAAACACT CCCAGCTTCT CAAGGACAGT GATTTTAGTT TCAGGAGCC      2880
TATCATGGCT CTACGCACAG TCATTTTGGA GATCCTGATG GAAAAGGAAA TGGACAACTC     2940
ACAAAGAGAA TGTATTAAGG ACATTCTCAC CAAACACCTT GTAGAACTCT CTATACTGGC     3000
CAGAACTTTC AAGAACACTC AGCTCCCTGA AAGGGCAATA TTTCAAATTA AACAGTACAA     3060
TTCAGTTAGC TGTGGAGTCT CTGAGTGGCA GCTGGAAGAA GCACAAGTAT CTGGGCAAA      3120
```

-continued

```
AAAGGAGCAG AGTCTTGCCC TGAGTATTCT CAAGCAAATG ATCAAGAAGT TGGATGCCAG   3180

CTGTGCAGCG AACAATCCCA GCCTAAAACT TACATACACA GAATGTCTGA GGGTTTGTGG   3240

CAACTGGTTA GCAGAAACGT GCTTAGAAAA TCCTGCGGTC ATCATGCAGA CCTATCTAGA   3300

AAAGGCAGTA GAAGTTGCTG GAAATTATGA TGGAGAAAGT AGTGATGAGC TAAGAAATGG   3360

AAAAATGAAG GCATTTCTCT CATTAGCCCG GTTTTCAGAT ACTCAATACC AAAGAATTGA   3420

AAACTACATG AAATCATCGG AATTTGAAAA CAAGCAAGCT CTCCTGAAAA GAGCCAAAGA   3480

GGAAGTAGGT CTCCTTAGGG AACATAAAAT TCAGACAAAC AGATACACAG TAAAGGTTCA   3540

GCGAGAGCTG GAGTTGGATG AATTAGCCCT GCGTGCACTG AAAGAGGATC GTAAACGCTT   3600

CTTATGTAAA GCAGTTGAAA ATTATATCAA CTGCTTATTA AGTGGAGAAG AACATGATAT   3660

GTGGGTATTC CGACTTTGTT CCCTCTGGCT TGAAAATTCT GGAGTTTCTG AAGTCAATGG   3720

CATGATGAAG AGAGACGGAA TGAAGATTCC AACATATAAA TTTTTGCCTC TTATGTACCA   3780

ATTGGCTGCT AGAATGGGGA CCAAGATGAT GGGAGGCCTA GGATTTCATG AAGTCCTCAA   3840

TAATCTAATC TCTAGAATTT CAATGGATCA CCCCCATCAC ACTTTGTTTA TTATACTGGC   3900

CTTAGCAAAT GCAAACAGAG ATGAATTTCT GACTAAACCA GAGGTAGCCA GAAGAAGCAG   3960

AATAACTAAA AATGTGCCTA ACAAAGCTC TCAGCTTGAT GAGGATCGAA CAGAGGCTGC   4020

AAATAGAATA ATATGTACTA TCAGAAGTAG GAGACCTCAG ATGGTCAGAA GTGTTGAGGC   4080

ACTTTGTGAT GCTTATATTA TATTAGCAAA CTTAGATGCC ACTCAGTGGA AGACTCAGAG   4140

AAAAGGCATA AATATTCCAG CAGACCAGCC AATTACTAAA CTTAAGAATT TAGAAGATGT   4200

TGTTGTCCCT ACTATGGAAA TTAAGGTGGA CCACACAGGA GAATATGAA ATCTGGTGAC   4260

TATACAGTCA TTTAAAGCAG AATTTCGCTT AGCAGGAGGT GTAAATTTAC CAAAAATAAT   4320

AGATTGTGTA GGTTCCGATG GCAAGGAGAG GAGACAGCTT GTTAAGGGCC GTGATGACCT   4380

GAGACAAGAT GCTGTCATGC AACAGGTCTT CCAGATGTGT AATACATTAC TGCAGAGAAA   4440

CACGGAAACT AGGAAGAGGA AATTAACTAT CTGTACTTAT AAGGTGGTTC CCCTCTCTCA   4500

GCGAAGTGGT GTTCTTGAAT GGTGCACAGG AACTGTCCCC ATTGGTGAAT TCTTGTTAA   4560

CAATGAAGAT GGTGCTCATA AAGATACAG GCCAAATGAT TCAGTGCCT TCAGTGCCA   4620

AAAGAAAATG ATGGAGGTGC AAAAAAGTC TTTTGAAGAG AAATATGAAG TCTTCATGGA   4680

TGTTTGCCAA AATTTTCAAC CAGTTTTCCG TTACTTCTGC ATGGAAAAAT TCTTGGATCC   4740

AGCTATTTGG TTTGAGAAGC GATTGGCTTA TACGCGCAGT GTAGCTACTT CTTCTATTGT   4800

TGGTTACATA CTTGGACTTG GTGATAGACA TGTACAGAAT ATCTTGATAA ATGAGCAGTC   4860

AGCAGAACTT GTACATATAG ATCTAGGTGT TGCTTTTGAA CAGGGCAAAA TCCTTCCTAC   4920

TCCTGAGACA GTTCCTTTTA GACTCACCAG AGATATTGTG GATGGCATGG GCATTACGGG   4980

TGTTGAAGGT GTCTTCAGAA GATGCTGTGA GAAACCATG GAAGTGATGA GAAACTCTCA   5040

GGAAACTCTG TTAACCATTG TAGAGGTCCT TCTATATGAT CCACTCTTTG ACTGGACCAT   5100

GAATCCTTTG AAAGCTTTGT ATTTACAGCA GAGGCCGGAA GATGAAACTG AGCTTCACCC   5160

TACTCTGAAT GCAGATGACC AAGAATGCAA ACGAAATCTC AGTGATATTG ACCAGAGTTT   5220

CGACAAAGTA GCTGAACGTG TCTTAATGAG ACTACAAGAG AAACTGAAAG GAGTGGAAGA   5280

AGGCACTGTG CTCAGTGTTG GTGGACAGGT GAATTTGCTC ATACAGCAGG CCATAGACCC   5340

CAAAAATCTC AGCCGACTTT TCCCAGGATG GAAAGCTTGG GTGTGATCTT CAGTATATGA   5400

ATTACCCTTT CATTCAGCCT TTAGAAATTA TATTTTAGCC TTTATTTTTA ACCTGCCAAC   5460

ATACTTTAAG TAGGGATTAA TATTTAAGTG AACTATTGTG GGTTTTTTTG AATGTTGGTT   5520
```

```
TTAATACTTG ATTTAATCAC CACTCAAAAA TGTTTTGATG GTCTTAAGGA ACATCTCTGC      5580

TTTCACTCTT TAGAAATAAT GGTCATTCGG GCTGGGCGCA GCGGCTCACG CCTGTAATCC      5640

CAGCACTTTG GGAGGCCGAG GTGAGCGGAT CACAAGGTCA GGAGTTCGAG ACCAGCCTGG      5700

CCAAGAGACC AGCCTGGCCA GTATGGTGAA ACCCTGTCTC TACTAAAAAT ACAAAAATTA      5760

GCCGAGCATG GTGGCGGGCA CCTGTAGTCC CAGCTACTCG AGAGGCTGAG GCAGGAGAAT      5820

CTCTTGAACC TGGGAGGTGA AGGTTGCTGT GGGCCAAAAT CATGCCATTG CACTCCAGCC      5880

TGGGTGACAA GAGCGAAACT CCATCTCAAA AA                                   5912
```

(2) INFORMATION FOR SEQ ID NO:2:

(i) SEQUENCE CHARACTERISTICS:
        (A) LENGTH: 9171 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (viii) POSITION IN GENOME:
        (A) CHROMOSOME/SEGMENT: 11q22-23

(xi) SEQUENCE DESCRIPTION: SEQ ID NO:2:

```
ATGAGTCTAG TACTTAATGA TCTGCTTATC TGCTGCCGTC AACTAGAACA TGATAGAGCT        60

ACAGAACGAA AGAAAGAAGT TGAGAAATTT AAGCGCCTGA TTCGAGATCC TGAAACAATT       120

AAACATCTAG ATCGGCATTC AGATTCCAAA CAAGGAAAAT ATTTGAATTG GGATGCTGTT       180

TTTAGATTTT TACAGAAATA TATTCAGAAA GAAACAGAAT GTCTGAGAAT AGCAAAACCA       240

AATGTATCAG CCTCAACACA AGCCTCCAGG CAGAAAAAGA TGCAGGAAAT CAGTAGTTTG       300

GTCAAATACT TCATCAAATG TGCAAACAGA AGAGCACCTA GGCTAAAATG TCAAGAACTC       360

TTAAATTATA TCATGGATAC AGTGAAAGAT TCATCTAATG GTGCTATTTA CGGAGCTGAT       420

TGTAGCAACA TACTACTCAA AGACATTCTT TCTGTGAGAA AATACTGGTG TGAAATATCT       480

CAGCAACAGT GGTTAGAATT GTTCTCTGTG TACTTCAGGC TCTATCTGAA ACCTTCACAA       540

GATGTTCATA GAGTTTTAGT GGCTAGAATA ATTCATGCTG TTACCAAAGG ATGCTGTTCT       600

CAGACTGACG GATTAAATTC CAAATTTTTG GACTTTTTTT CCAAGGCTAT TCAGTGTGCG       660

AGACAAGAAA AGAGCTCTTC AGGTCTAAAT CATATCTTAG CAGCTCTTAC TATCTTCCTC       720

AAGACTTTGG CTGTCAACTT TCGAATTCGA GTGTGTGAAT TAGGAGATGA AATTCTTCCC       780

ACTTTGCTTT ATATTTGGAC TCAACATAGG CTTAATGATT CTTTAAAAGA AGTCATTATT       840

GAATTATTTC AACTGCAAAT TTATATCCAT CATCCGAAAG GAGCCAAAAC CCAAGAAAAA       900

GGTGCTTATG AATCAACAAA ATGGAGAAGT ATTTTATACA ACTTATATGA TCTGCTAGTG       960

AATGAGATAA GTCATATAGG AAGTAGAGGA AAGTATTCTT CAGGATTTCG TAATATTGCC      1020

GTCAAAGAAA ATTTGATTGA ATTGATGGCA GATATCTGTC ACCAGGTTTT TAATGAAGAT      1080

ACCAGATCCT TGGAGATTTC TCAATCTTAC ACTACTACAC AAAGAGAATC TAGTGATTAC      1140

AGTGTCCCTT GCAAAAGGAA GAAAATAGAA CTAGGCTGGG AAGTAATAAA AGATCACCTT      1200

CAGAAGTCAC AGAATGATTT TGATCTTGTG CCTTGGCTAC AGATTGCAAC CCAATTAATA      1260

TCAAAGTATC CTGCAAGTTT ACCTAACTGT GAGCTGTCTC CATTACTGAT GATACTATCT      1320

CAGCTTCTAC CCCAACAGCG ACATGGGGAA CGTACACCAT ATGTGTTACG ATGCCTTACG      1380
```

```
GAAGTTGCAT TGTGTCAAGA CAAGAGGTCA AACCTAGAAA GCTCACAAAA GTCAGATTTA    1440

TTAAAACTCT GGAATAAAAT TTGGTGTATT ACCTTTCGTG GTATAAGTTC TGAGCAAATA    1500

CAAGCTGAAA ACTTTGGCTT ACTTGGAGCC ATAATTCAGG GTAGTTTAGT TGAGGTTGAC    1560

AGAGAATTCT GGAAGTTATT TACTGGGTCA GCCTGCAGAC CTTCATGTCC TGCAGTATGC    1620

TGTTTGACTT TGGCACTGAC CACCAGTATA GTTCCAGGAA CGGTAAAAAT GGGAATAGAG    1680

CAAAATATGT GTGAAGTAAA TAGAAGCTTT TCTTTAAAGG AATCAATAAT GAAATGGCTC    1740

TTATTCTATC AGTTAGAGGG TGACTTAGAA AATAGCACAG AAGTGCCTCC AATTCTTCAC    1800

AGTAATTTTC CTCATCTTGT ACTGGAGAAA ATTCTTGTGA GTCTCACTAT GAAAAACTGT    1860

AAAGCTGCAA TGAATTTTTT CCAAAGCGTG CCAGAATGTG AACACCACCA AAAAGATAAA    1920

GAAGAACTTT CATTCTCAGA AGTAGAAGAA CTATTTCTTC AGACAACTTT TGACAAGATG    1980

GACTTTTTAA CCATTGTGAG AGAATGTGGT ATAGAAAAGC ACCAGTCCAG TATTGGCTTC    2040

TCTGTCCACC AGAATCTCAA GGAATCACTG GATCGCTGTC TTCTGGGATT ATCAGAACAG    2100

CTTCTGAATA ATTACTCATC TGAGATTACA AATTCAGAAA CTCTTGTCCG GTGTTCACGT    2160

CTTTTGGTGG GTGTCCTTGG CTGCTACTGT TACATGGGTG TAATAGCTGA AGAGGAAGCA    2220

TATAAGTCAG AATTATTCCA GAAAGCCAAG TCTCTAATGC AATGTGCAGG AGAAAGTATC    2280

ACTCTGTTTA AAAATAAGAC AAATGAGGAA TTCAGAATTG GTTCCTTGAG AAATATGATG    2340

CAGCTATGTA CACGTTGCTT GAGCAACTGT ACCAAGAAGA GTCCAAATAA GATTGCATCT    2400

GGCTTTTTCC TGCGATTGTT AACATCAAAG CTAATGAATG ACATTGCAGA TATTTGTAAA    2460

AGTTTAGCAT CCTTCATCAA AAAGCCATTT GACCGTGGAG AAGTAGAATC AATGGAAGAT    2520

GATACTAATG GAAATCTAAT GGAGGTGGAG GATCAGTCAT CCATGAATCT ATTTAACGAT    2580

TACCCTGATA GTAGTGTTAG TGATGCAAAC GAACCTGGAG AGAGCCAAAG TACCATAGGT    2640

GCCATTAATC CTTTAGCTGA AGAATATCTG TCAAAGCAAG ATCTACTTTT CTTAGACATG    2700

CTCAAGTTCT TGTGTTTGTG TGTAACTACT GCTCAGACCA ATACTGTGTC CTTTAGGGCA    2760

GCTGATATTC GGAGGAAATT GTTAATGTTA ATTGATTCTA GCACGCTAGA ACCTACCAAA    2820

TCCCTCCACC TGCATATGTA TCTAATGCTT TTAAAGGAGC TTCCTGGAGA AGAGTACCCC    2880

TTGCCAATGG AAGATGTTCT TGAACTTCTG AAACCACTAT CCAATGTGTG TTCTTTGTAT    2940

CGTCGTGACC AAGATGTTTG TAAAACTATT TTAAACCATG TCCTTCATGT AGTGAAAAAC    3000

CTAGGTCAAA GCAATATGGA CTCTGAGAAC ACAAGGGATG CTCAAGGACA GTTTCTTACA    3060

GTAATTGGAG CATTTGGCA TCTAACAAAG GAGAGGAAAT ATATATTCTC TGTAAGAATG    3120

GCCCTAGTAA ATTGCCTTAA AACTTTGCTT GAGGCTGATC CTTATTCAAA ATGGGCCATT    3180

CTTAATGTAA TGGGAAAAGA CTTTCCTGTA AATGAAGTAT TTACACAATT TCTTGCTGAC    3240

AATCATCACC AAGTTCGCAT GTTGGCTGCA GAGTCAATCA ATAGATTGTT CCAGGACACG    3300

AAGGGAGATT CTTCCAGGTT ACTGAAAGCA CTTCCTTTGA AGCTTCAGCA AACAGCTTTT    3360

GAAAATGCAT ACTTGAAAGC TCAGGAAGGA ATGAGAGAAA TGTCCCATAG TGCTGAGAAC    3420

CCTGAAACTT TGGATGAAAT TTATAATAGA AAATCTGTTT TACTGACGTT GATAGCTGTG    3480

GTTTTATCCT GTAGCCCTAT CTGCGAAAAA CAGGCTTTGT TTGCCCTGTG TAAATCTGTG    3540

AAAGAGAATG GATTAGAACC TCACCTTGTG AAAAAGGTTT TAGAGAAAGT TTCTGAAACT    3600

TTTGGATATA GACGTTTAGA AGACTTTATG GCATCTCATT TAGATTATCT GGTTTTGGAA    3660

TGGCTAAATC TTCAAGATAC TGAATACAAC TTATCTTCTT TTCCTTTTAT TTTATTAAAC    3720
```

-continued

```
TACACAAATA TTGAGGATTT CTATAGATCT TGTTATAAGG TTTTGATTCC ACATCTGGTG    3780

ATTAGAAGTC ATTTTGATGA GGTGAAGTCC ATTGCTAATC AGATTCAAGA GGACTGGAAA    3840

AGTCTTCTAA CAGACTGCTT TCCAAAGATT CTTGTAAATA TTCTTCCTTA TTTTGCCTAT    3900

GAGGGTACCA GAGACAGTGG GATGGCACAG CAAAGAGAGA CTGCTACCAA GGTCTATGAT    3960

ATGCTTAAAA GTGAAAACTT ATTGGGAAAA CAGATTGATC ACTTATTCAT TAGTAATTTA    4020

CCAGAGATTG TGGTGGAGTT ATTGATGACG TTACATGAGC CAGCAAATTC TAGTGCCAGT    4080

CAGAGCACTG ACCTCTGTGA CTTTTCAGGG GATTTGGATC CTGCTCCTAA TCCACCTCAT    4140

TTTCCATCGC ATGTGATTAA AGCAACATTT GCCTATATCA GCAATTGTCA TAAAACCAAG    4200

TTAAAAAGCA TTTTAGAAAT TCTTTCCAAA AGCCCTGATT CCTATCAGAA AATTCTTCTT    4260

GCCATATGTG AGCAAGCAGC TGAAACAAAT AATGTTTATA GAAGCACAG AATTCTTAAA     4320

ATATATCACC TGTTTGTTAG TTTATTACTG AAAGATATAA AAAGTGGCTT AGGAGGAGCT    4380

TGGGCCTTTG TTCTTCGAGA CGTTATTTAT ACTTTGATTC ACTATATCAA CCAAAGGCCT    4440

TCTTGTATCA TGGATGTGTC ATTACGTAGC TTCTCCCTTT GTTGTGACTT ATTAAGTCAG    4500

GTTTGCCAGA CAGCCGTGAC TTACTGTAAG GATGCTCTAG AAAACCATCT TCATGTTATT    4560

GTTGGTACAC TTATACCCCT TGTGTATGAG CAGGTGGAGG TTCAGAAACA GGTATTGGAC    4620

TTGTTGAAAT ACTTAGTGAT AGATAACAAG GATAATGAAA ACCTCTATAT CACGATTAAG    4680

CTTTTAGATC CTTTTCCTGA CCATGTTGTT TTTAAGGATT TGCGTATTAC TCAGCAAAAA    4740

ATCAAATACA GTAGAGGACC CTTTTCACTC TTGGAGGAAA TTAACCATTT TCTCTCAGTA    4800

AGTGTTTATG ATGCACTTCC ATTGACAAGA CTTGAAGGAC TAAAGGATCT TCGAAGACAA    4860

CTGGAACTAC ATAAAGATCA GATGGTGGAC ATTATGAGAG CTTCTCAGGA TAATCCGCAA    4920

GATGGGATTA TGGTGAAACT AGTTGTCAAT TTGTTGCAGT TATCCAAGAT GGCAATAAAC    4980

CACACTGGTG AAAAGAAGT TCTAGAGGCT GTTGGAAGCT GCTTGGGAGA AGTGGGTCCT     5040

ATAGATTTCT CTACCATAGC TATACAACAT AGTAAAGATG CATCTTATAC CAAGGCCCTT    5100

AAGTTATTTG AAGATAAAGA ACTTCAGTGG ACCTTCAAA TGCTGACCTA CCTGAATAAC     5160

ACACTGGTAG AAGATTGTGT CAAAGTTCGA TCAGCAGCTG TTACCTGTTT GAAAAACATT    5220

TTAGCCACAA AGACTGGACA TAGTTTCTGG GAGATTTATA AGATGACAAC AGATCCAATG    5280

CTGGCCTATC TACAGCCTTT TAGAACATCA AGAAAAAAGT TTTTAGAAGT ACCCAGATTT    5340

GACAAAGAAA ACCCTTTTGA AGGCCTGGAT GATATAAATC TGTGGATTCC TCTAAGTGAA    5400

AATCATGACA TTTGGATAAA GACACTGACT TGTGCTTTTT TGGACAGTGG AGGCACAAAA    5460

TGTGAAATTC TTCAATTATT AAAGCCAATG TGTGAAGTGA AAACTGACTT TTGTCAGACT    5520

GTACTTCCAT ACTTGATTCA TGATATTTTA CTCCAAGATA CAAATGAATC ATGGAGAAAT    5580

CTGCTTTCTA CACATGTTCA GGGATTTTTC ACCAGCTGTC TTCGACACTT CTCGCAAACG    5640

AGCCGATCCA CAACCCCTGC AAACTTGGAT TCAGAGTCAG AGCACTTTTT CCGATGCTGT    5700

TTGGATAAAA AATCACAAAG AACAATGCTT GCTGTTGTGG ACTACATGAG AAGACAAAAG    5760

AGACCTTCTT CAGGAACAAT TTTTAATGAT GCTTTCTGGC TGGATTTAAA TTATCTAGAA    5820

GTTGCCAAGG TAGCTCAGTC TTGTGCTGCT CACTTTACAG CTTTACTCTA TGCAGAAATC    5880

TATGCAGATA AGAAAGTAT GGATGATCAA GAGAAAGAA GTCTTGCATT TGAAGAAGGA      5940

AGCCAGAGTA CAACTATTTC TAGCTTGAGT GAAAAAGTA AAGAAGAAAC TGGAATAAGT     6000

TTACAGGATC TTCTCTTAGA AATCTACAGA AGTATAGGGG AGCCAGATAG TTTGTATGGC    6060

TGTGGTGGAG GGAAGATGTT ACAACCCATT ACTAGACTAC GAACATATGA ACACGAAGCA    6120
```

```
ATGTGGGCA AAGCCCTAGT AACATATGAC CTCGAAACAG CAATCCCCTC ATCAACACGC    6180

CAGGCAGGAA TCATTCAGGC CTTGCAGAAT TTGGGACTCT GCCATATTCT TTCCGTCTAT    6240

TTAAAAGGAT TGGATTATGA AAATAAAGAC TGGTGTCCTG AACTAGAAGA ACTTCATTAC    6300

CAAGCAGCAT GGAGGAATAT GCAGTGGGAC CATTGCACTT CCGTCAGCAA AGAAGTAGAA    6360

GGAACCAGTT ACCATGAATC ATTGTACAAT GCTCTACAAT CTCTAAGAGA CAGAGAATTC    6420

TCTACATTTT ATGAAAGTCT CAAATATGCC AGAGTAAAAG AAGTGGAAGA GATGTGTAAG    6480

CGCAGCCTTG AGTCTGTGTA TTCGCTCTAT CCCACACTTA GCAGGTTGCA GGCCATTGGA    6540

GAGCTGGAAA GCATTGGGGA GCTTTTCTCA AGATCAGTCA CACATAGACA ACTCTCTGAA    6600

GTATATATTA AGTGGCAGAA ACACTCCCAG CTTCTCAAGG ACAGTGATTT TAGTTTTCAG    6660

GAGCCTATCA TGGCTCTACG CACAGTCATT TTGGAGATCC TGATGGAAAA GGAAATGGAC    6720

AACTCACAAA GAGAATGTAT TAAGGACATT CTCACCAAAC ACCTTGTAGA ACTCTCTATA    6780

CTGGCCAGAA CTTTCAAGAA CACTCAGCTC CCTGAAAGGG CAATATTTCA AATTAAACAG    6840

TACAATTCAG TTAGCTGTGG AGTCTCTGAG TGGCAGCTGG AAGAAGCACA AGTATTCTGG    6900

GCAAAAAAGG AGCAGAGTCT TGCCCTGAGT ATTCTCAAGC AAATGATCAA GAAGTTGGAT    6960

GCCAGCTGTG CAGCGAACAA TCCCAGCCTA AAACTTACAT ACACAGAATG TCTGAGGGTT    7020

TGTGGCAACT GGTTAGCAGA AACGTGCTTA GAAAATCCTG CGGTCATCAT GCAGACCTAT    7080

CTAGAAAAGG CAGTAGAAGT TGCTGGAAAT TATGATGGAG AAAGTAGTGA TGAGCTAAGA    7140

AATGGAAAAA TGAAGGCATT TCTCTCATTA GCCCGGTTTT CAGATACTCA ATACCAAAGA    7200

ATTGAAAACT ACATGAAATC ATCGGAATTT GAAACAAGC AAGCTCTCCT GAAAAGAGCC    7260

AAAGAGGAAG TAGGTCTCCT TAGGGAACAT AAAATTCAGA CAAACAGATA CACAGTAAAG    7320

GTTCAGCGAG AGCTGGAGTT GGATGAATTA GCCCTGCGTG CACTGAAAGA GGATCGTAAA    7380

CGCTTCTTAT GTAAAGCAGT TGAAAATTAT ATCAACTGCT TATTAAGTGG AGAAGAACAT    7440

GATATGTGGG TATTCCGACT TTGTTCCCTC TGGCTTGAAA ATTCTGGAGT TTCTGAAGTC    7500

AATGGCATGA TGAAGAGAGA CGGAATGAAG ATTCCAACAT ATAAATTTTT GCCTCTTATG    7560

TACCAATTGG CTGCTAGAAT GGGGACCAAG ATGATGGGAG GCCTAGGATT TCATGAAGTC    7620

CTCAATAATC TAATCTCTAG AATTTCAATG GATCACCCCC ATCACACTTT GTTTATTATA    7680

CTGGCCTTAG CAAATGCAAA CAGAGATGAA TTTCTGACTA AACCAGAGGT AGCCAGAAGA    7740

AGCAGAATAA CTAAAAATGT GCCTAAACAA AGCTCTCAGC TTGATGAGGA TCGAACAGAG    7800

GCTGCAAATA GAATAATATG TACTATCAGA AGTAGGAGAC CTCAGATGGT CAGAAGTGTT    7860

GAGGCACTTT GTGATGCTTA TATTATATTA GCAAACTTAG ATGCCACTCA GTGGAAGACT    7920

CAGAGAAAAG GCATAAATAT TCCAGCAGAC CAGCCAATTA CTAAACTTAA GAATTTAGAA    7980

GATGTTGTTG TCCCTACTAT GGAAATTAAG GTGGACCACA CAGGAGAATA TGGAAATCTG    8040

GTGACTATAC AGTCATTTAA AGCAGAATTT CGCTTAGCAG GAGGTGTAAA TTTACCAAAA    8100

ATAATAGATT GTGTAGGTTC CGATGGCAAG GAGAGGAGAC AGCTTGTTAA GGGCCGTGAT    8160

GACCTGAGAC AAGATGCTGT CATGCAACAG GTCTTCCAGA TGTGTAATAC ATTACTGCAG    8220

AGAAACACGG AAACTAGGAA GAGGAAATTA ACTATCTGTA CTTATAAGGT GGTTCCCCTC    8280

TCTCAGCGAA GTGGTGTTCT TGAATGGTGC ACAGGAACTG TCCCCATTGG TGAATTTCTT    8340

GTTAACAATG AAGATGGTGC TCATAAAAGA TACAGGCCAA ATGATTTCAG TGCCTTTCAG    8400

TGCCAAAAGA AAATGATGGA GGTGCAAAAA AAGTCTTTTG AAGAGAAATA TGAAGTCTTC    8460
```

-continued

```
ATGGATGTTT GCCAAAATTT TCAACCAGTT TTCCGTTACT TCTGCATGGA AAAATTCTTG    8520

GATCCAGCTA TTTGGTTTGA GAAGCGATTG GCTTATACGC GCAGTGTAGC TACTTCTTCT    8580

ATTGTTGGTT ACATACTTGG ACTTGGTGAT AGACATGTAC AGAATATCTT GATAAATGAG    8640

CAGTCAGCAG AACTTGTACA TATAGATCTA GGTGTTGCTT TTGAACAGGG CAAAATCCTT    8700

CCTACTCCTG AGACAGTTCC TTTTAGACTC ACCAGAGATA TTGTGGATGG CATGGGCATT    8760

ACGGGTGTTG AAGGTGTCTT CAGAAGATGC TGTGAGAAAA CCATGGAAGT GATGAGAAAC    8820

TCTCAGGAAA CTCTGTTAAC CATTGTAGAG GTCCTTCTAT ATGATCCACT CTTTGACTGG    8880

ACCATGAATC CTTTGAAAGC TTTGTATTTA CAGCAGAGGC CGGAAGATGA AACTGAGCTT    8940

CACCCTACTC TGAATGCAGA TGACCAAGAA TGCAAACGAA ATCTCAGTGA TATTGACCAG    9000

AGTTTCAACA AAGTAGCTGA ACGTGTCTTA ATGAGACTAC AAGAGAAACT GAAAGGAGTG    9060

GAAGAAGGCA CTGTGCTCAG TGTTGGTGGA CAAGTGAATT TGCTCATACA GCAGGCCATA    9120

GACCCCAAAA ATCTCAGCCG ACTTTTCCCA GGATGGAAAG CTTGGGTGTG A             9171
```

(2) INFORMATION FOR SEQ ID NO:3:

(i) SEQUENCE CHARACTERISTICS:
        (A) LENGTH: 3056 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:3:

```
Met Ser Leu Val Leu Asn Asp Leu Leu Ile Cys Cys Arg Gln Leu Glu
1               5                   10                  15

His Asp Arg Ala Thr Glu Arg Lys Lys Glu Val Glu Lys Phe Lys Arg
            20                  25                  30

Leu Ile Arg Asp Pro Glu Thr Ile Lys His Leu Asp Arg His Ser Asp
        35                  40                  45

Ser Lys Gln Gly Lys Tyr Leu Asn Trp Asp Ala Val Phe Arg Phe Leu
    50                  55                  60

Gln Lys Tyr Ile Gln Lys Glu Thr Glu Cys Leu Arg Ile Ala Lys Pro
65                  70                  75                  80

Asn Val Ser Ala Ser Thr Gln Ala Ser Arg Gln Lys Lys Met Gln Glu
                85                  90                  95

Ile Ser Ser Leu Val Lys Tyr Phe Ile Lys Cys Ala Asn Arg Arg Ala
            100                 105                 110

Pro Arg Leu Lys Cys Gln Glu Leu Leu Asn Tyr Ile Met Asp Thr Val
        115                 120                 125

Lys Asp Ser Ser Asn Gly Ala Ile Tyr Gly Ala Asp Cys Ser Asn Ile
    130                 135                 140

Leu Leu Lys Asp Ile Leu Ser Val Arg Lys Tyr Trp Cys Glu Ile Ser
145                 150                 155                 160

Gln Gln Gln Trp Leu Glu Leu Phe Ser Val Tyr Phe Arg Leu Tyr Leu
                165                 170                 175

Lys Pro Ser Gln Asp Val His Arg Val Leu Val Ala Arg Ile Ile His
            180                 185                 190

Ala Val Thr Lys Gly Cys Cys Ser Gln Thr Asp Gly Leu Asn Ser Lys
        195                 200                 205
```

-continued

```
Phe Leu Asp Phe Phe Ser Lys Ala Ile Gln Cys Ala Arg Gln Glu Lys
        210                 215                 220
Ser Ser Ser Gly Leu Asn His Ile Leu Ala Ala Leu Thr Ile Phe Leu
225                 230                 235                 240
Lys Thr Leu Ala Val Asn Phe Arg Ile Arg Val Cys Glu Leu Gly Asp
                245                 250                 255
Glu Ile Leu Pro Thr Leu Val Tyr Ile Trp Thr Gln His Arg Leu Asn
            260                 265                 270
Asp Ser Leu Lys Glu Val Ile Ile Glu Leu Phe Gln Leu Gln Ile Tyr
        275                 280                 285
Ile His His Pro Lys Gly Ala Lys Thr Gln Glu Lys Gly Ala Tyr Glu
    290                 295                 300
Ser Thr Lys Trp Arg Ser Ile Leu Tyr Asn Leu Tyr Asp Leu Leu Val
305                 310                 315                 320
Asn Glu Ile Ser His Ile Gly Ser Arg Gly Lys Tyr Ser Ser Gly Phe
                325                 330                 335
Arg Asn Ile Ala Val Lys Glu Asn Leu Ile Glu Leu Met Ala Asp Ile
            340                 345                 350
Cys His Gln Val Phe Asn Glu Asp Thr Arg Ser Leu Glu Ile Ser Gln
        355                 360                 365
Ser Tyr Thr Thr Thr Gln Arg Glu Ser Ser Asp Tyr Ser Val Pro Cys
    370                 375                 380
Lys Arg Lys Lys Ile Glu Leu Gly Trp Glu Val Ile Lys Asp His Leu
385                 390                 395                 400
Gln Lys Ser Gln Asn Asp Phe Asp Leu Val Pro Trp Leu Gln Ile Ala
                405                 410                 415
Thr Gln Leu Ile Ser Lys Tyr Pro Ala Ser Leu Pro Asn Cys Glu Leu
            420                 425                 430
Ser Pro Leu Leu Met Ile Leu Ser Gln Leu Leu Pro Gln Gln Arg His
        435                 440                 445
Gly Glu Arg Thr Pro Tyr Val Leu Arg Cys Leu Thr Glu Val Ala Leu
    450                 455                 460
Cys Gln Asp Lys Arg Ser Asn Leu Glu Ser Ser Gln Lys Ser Asp Leu
465                 470                 475                 480
Leu Lys Leu Trp Asn Lys Ile Trp Cys Ile Thr Phe Arg Gly Ile Ser
                485                 490                 495
Ser Glu Gln Lys Gln Ala Glu Asn Phe Gly Leu Leu Gly Ala Ile Ile
            500                 505                 510
Gln Gly Ser Leu Val Glu Val Asp Arg Glu Phe Trp Lys Leu Phe Thr
        515                 520                 525
Gly Ser Ala Cys Arg Pro Ser Cys Pro Ala Val Cys Cys Leu Thr Leu
    530                 535                 540
Ala Leu Thr Thr Ser Ile Val Pro Gly Ala Val Lys Met Gly Ile Glu
545                 550                 555                 560
Gln Asn Met Cys Glu Val Asn Arg Ser Phe Ser Leu Lys Glu Ser Ile
                565                 570                 575
Met Lys Trp Leu Leu Phe Tyr Gln Leu Glu Gly Asp Leu Glu Asn Ser
            580                 585                 590
Thr Glu Val Pro Pro Ile Leu His Ser Asn Phe Pro His Leu Val Leu
        595                 600                 605
Glu Lys Ile Leu Val Ser Leu Thr Met Lys Asn Cys Lys Ala Ala Met
    610                 615                 620
Asn Phe Phe Gln Ser Val Pro Glu Cys Glu His His His Lys Asp Lys
```

-continued

```
            625                 630                 635                 640
Glu Glu Leu Ser Phe Ser Glu Val Glu Leu Phe Leu Gln Thr Thr
                    645                 650                 655
Phe Asp Lys Met Asp Phe Leu Thr Ile Val Arg Glu Cys Gly Ile Glu
                660                 665                 670
Lys His Gln Ser Ser Ile Gly Phe Ser Val His Gln Asn Leu Lys Glu
                675                 680                 685
Ser Leu Asp Arg Cys Leu Leu Gly Leu Ser Glu Gln Leu Leu Asn Asn
            690                 695                 700
Tyr Ser Ser Glu Ile Thr Asn Ser Glu Thr Leu Val Arg Cys Ser Arg
705                 710                 715                 720
Leu Leu Val Gly Val Leu Gly Cys Tyr Cys Tyr Met Gly Val Ile Ala
                    725                 730                 735
Glu Glu Glu Ala Tyr Lys Ser Glu Leu Phe Gln Lys Ala Asn Ser Leu
                740                 745                 750
Met Gln Cys Ala Gly Glu Ser Ile Thr Leu Phe Lys Asn Lys Thr Asn
                755                 760                 765
Glu Glu Phe Arg Ile Gly Ser Leu Arg Asn Met Met Gln Leu Cys Thr
            770                 775                 780
Arg Cys Leu Ser Asn Cys Thr Lys Lys Ser Pro Asn Lys Ile Ala Ser
785                 790                 795                 800
Gly Phe Phe Leu Arg Leu Leu Thr Ser Lys Leu Met Asn Asp Ile Ala
                    805                 810                 815
Asp Ile Cys Lys Ser Leu Ala Ser Phe Ile Lys Lys Pro Phe Asp Arg
                820                 825                 830
Gly Glu Val Glu Ser Met Glu Asp Asp Thr Asn Gly Asn Leu Met Glu
                835                 840                 845
Val Glu Asp Gln Ser Ser Met Asn Leu Phe Asn Asp Tyr Pro Asp Ser
850                 855                 860
Ser Val Ser Asp Ala Asn Glu Pro Gly Glu Ser Gln Ser Thr Ile Gly
865                 870                 875                 880
Ala Ile Asn Pro Leu Ala Glu Glu Tyr Leu Ser Lys Gln Asp Leu Leu
                    885                 890                 895
Phe Leu Asp Met Leu Lys Phe Leu Cys Leu Cys Val Thr Thr Ala Gln
                900                 905                 910
Thr Asn Thr Val Ser Phe Arg Ala Ala Asp Ile Arg Arg Lys Leu Leu
                915                 920                 925
Met Leu Ile Asp Ser Ser Thr Leu Glu Pro Thr Lys Ser Leu His Leu
            930                 935                 940
His Met Tyr Leu Met Leu Leu Lys Glu Leu Pro Gly Glu Glu Tyr Pro
945                 950                 955                 960
Leu Pro Met Glu Asp Val Leu Glu Leu Leu Lys Pro Leu Ser Asn Val
                    965                 970                 975
Cys Ser Leu Tyr Arg Arg Asp Gln Asp Val Cys Lys Thr Ile Leu Asn
                980                 985                 990
His Val Leu His Val Val Lys Asn Leu Gly Gln Ser Asn Met Asp Ser
            995                 1000                1005
Glu Asn Thr Arg Asp Ala Gln Gly Gln Phe Leu Thr Val Ile Gly Ala
            1010                1015                1020
Phe Trp His Leu Thr Lys Glu Arg Lys Tyr Ile Phe Ser Val Arg Met
1025                1030                1035                1040
Ala Leu Val Asn Cys Leu Lys Thr Leu Leu Glu Ala Asp Pro Tyr Ser
                    1045                1050                1055
```

-continued

Lys Trp Ala Ile Leu Asn Val Met Gly Lys Asp Phe Pro Val Asn Glu
              1060                1065                1070
Val Phe Thr Gln Phe Leu Ala Asp Asn His His Gln Val Arg Met Leu
         1075                1080                1085
Ala Ala Glu Ser Ile Asn Arg Leu Phe Gln Asp Thr Lys Gly Asp Ser
         1090                1095                1100
Ser Arg Leu Leu Lys Ala Leu Pro Leu Lys Leu Gln Gln Thr Ala Phe
1105                1110                1115                1120
Glu Asn Ala Tyr Leu Lys Ala Gln Glu Gly Met Arg Glu Met Ser His
              1125                1130                1135
Ser Ala Glu Asn Pro Glu Thr Leu Asp Glu Ile Tyr Asn Arg Lys Ser
              1140                1145                1150
Val Leu Leu Thr Leu Ile Ala Val Val Leu Ser Cys Ser Pro Ile Cys
              1155                1160                1165
Glu Lys Gln Ala Leu Phe Ala Leu Cys Lys Ser Val Lys Glu Asn Gly
              1170                1175                1180
Leu Glu Pro His Leu Val Lys Lys Val Leu Glu Lys Val Ser Glu Thr
1185                1190                1195                1200
Phe Gly Tyr Arg Arg Leu Glu Asp Phe Met Ala Ser His Leu Asp Tyr
              1205                1210                1215
Leu Val Leu Glu Trp Leu Asn Leu Gln Asp Thr Glu Tyr Asn Leu Ser
              1220                1225                1230
Ser Phe Pro Phe Ile Leu Leu Asn Tyr Thr Asn Ile Glu Asp Phe Tyr
              1235                1240                1245
Arg Ser Cys Tyr Lys Val Leu Ile Pro His Leu Val Ile Arg Ser His
              1250                1255                1260
Phe Asp Glu Val Lys Ser Ile Ala Asn Gln Ile Gln Glu Asp Trp Lys
1265                1270                1275                1280
Ser Leu Leu Thr Asp Cys Phe Pro Lys Ile Leu Val Asn Ile Leu Pro
              1285                1290                1295
Tyr Phe Ala Tyr Glu Gly Thr Arg Asp Ser Gly Met Ala Gln Gln Arg
              1300                1305                1310
Glu Thr Ala Thr Lys Val Tyr Asp Met Leu Lys Ser Glu Asn Leu Leu
              1315                1320                1325
Gly Lys Gln Ile Asp His Leu Phe Ile Ser Asn Leu Pro Glu Ile Val
              1330                1335                1340
Val Glu Leu Leu Met Thr Leu His Glu Pro Ala Asn Ser Ser Ala Ser
1345                1350                1355                1360
Gln Ser Thr Asp Leu Cys Asp Phe Ser Gly Asp Leu Asp Pro Ala Pro
              1365                1370                1375
Asn Pro Pro His Phe Pro Ser His Val Ile Lys Ala Thr Phe Ala Tyr
              1380                1385                1390
Ile Ser Asn Cys His Lys Thr Lys Leu Lys Ser Ile Leu Glu Ile Leu
              1395                1400                1405
Ser Lys Ser Pro Asp Ser Tyr Gln Lys Ile Leu Leu Ala Ile Cys Glu
              1410                1415                1420
Gln Ala Ala Glu Thr Asn Asn Val Tyr Lys Lys His Arg Ile Leu Lys
1425                1430                1435                1440
Ile Tyr His Leu Phe Val Ser Leu Leu Leu Lys Asp Ile Lys Ser Gly
              1445                1450                1455
Leu Gly Gly Ala Trp Ala Phe Val Leu Arg Asp Val Ile Tyr Thr Leu
              1460                1465                1470

```
Ile His Tyr Ile Asn Gln Arg Pro Ser Cys Ile Met Asp Val Ser Leu
        1475                1480                1485

Arg Ser Phe Ser Leu Cys Cys Asp Leu Leu Ser Gln Val Cys Gln Thr
        1490                1495                1500

Ala Val Thr Tyr Cys Lys Asp Ala Leu Glu Asn His Leu His Val Ile
1505                1510                1515                1520

Val Gly Thr Leu Ile Pro Leu Val Tyr Glu Gln Val Glu Val Gln Lys
            1525                1530                1535

Gln Val Leu Asp Leu Leu Lys Tyr Leu Val Ile Asp Asn Lys Asp Asn
            1540                1545                1550

Glu Asn Leu Tyr Ile Thr Ile Lys Leu Leu Asp Pro Phe Pro Asp His
            1555                1560                1565

Val Val Phe Lys Asp Leu Arg Ile Thr Gln Gln Lys Ile Lys Tyr Ser
        1570                1575                1580

Arg Gly Pro Phe Ser Leu Leu Glu Glu Ile Asn His Phe Leu Ser Val
1585                1590                1595                1600

Ser Val Tyr Asp Ala Leu Pro Leu Thr Arg Leu Glu Gly Leu Lys Asp
            1605                1610                1615

Leu Arg Arg Gln Leu Glu Leu His Lys Asp Gln Met Val Asp Ile Met
            1620                1625                1630

Arg Ala Ser Gln Asp Asn Pro Gln Asp Gly Ile Met Val Lys Leu Val
            1635                1640                1645

Val Asn Leu Leu Gln Leu Ser Lys Met Ala Ile Asn His Thr Gly Glu
        1650                1655                1660

Lys Glu Val Leu Glu Ala Val Gly Ser Cys Leu Gly Glu Val Gly Pro
1665                1670                1675                1680

Ile Asp Phe Ser Thr Ile Ala Ile Gln His Ser Lys Asp Ala Ser Tyr
            1685                1690                1695

Thr Lys Ala Leu Lys Leu Phe Glu Asp Lys Glu Leu Gln Trp Thr Phe
            1700                1705                1710

Ile Met Leu Thr Tyr Leu Asn Asn Thr Leu Val Glu Asp Cys Val Lys
        1715                1720                1725

Val Arg Ser Ala Ala Val Thr Cys Leu Lys Asn Ile Leu Ala Thr Lys
        1730                1735                1740

Thr Gly His Ser Phe Trp Glu Ile Tyr Lys Met Thr Thr Asp Pro Met
1745                1750                1755                1760

Leu Ala Tyr Leu Gln Pro Phe Arg Thr Ser Arg Lys Lys Phe Leu Glu
            1765                1770                1775

Val Pro Arg Phe Asp Lys Glu Asn Pro Phe Glu Gly Leu Asp Asp Ile
            1780                1785                1790

Asn Leu Trp Ile Pro Leu Ser Glu Asn His Asp Ile Trp Ile Lys Thr
        1795                1800                1805

Leu Thr Cys Ala Phe Leu Asp Ser Gly Gly Thr Lys Cys Glu Ile Leu
        1810                1815                1820

Gln Leu Leu Lys Pro Met Cys Glu Val Lys Thr Asp Phe Cys Gln Thr
1825                1830                1835                1840

Val Leu Pro Tyr Leu Ile His Asp Ile Leu Leu Gln Asp Thr Asn Glu
            1845                1850                1855

Ser Trp Arg Asn Leu Leu Ser Thr His Val Gln Gly Phe Phe Thr Ser
            1860                1865                1870

Cys Leu Arg His Phe Ser Gln Thr Ser Arg Ser Thr Thr Pro Ala Asn
        1875                1880                1885

Leu Asp Ser Glu Ser Glu His Phe Phe Arg Cys Cys Leu Asp Lys Lys
```

```
                 1890                1895                1900
Ser Gln Arg Thr Met Leu Ala Val Val Asp Tyr Met Arg Gln Lys
1905                1910                1915                1920

Arg Pro Ser Ser Gly Thr Ile Phe Asn Asp Ala Phe Trp Leu Asp Leu
                1925                1930                1935

Asn Tyr Leu Glu Val Ala Lys Val Ala Gln Ser Cys Ala Ala His Phe
            1940                1945                1950

Thr Ala Leu Leu Tyr Ala Glu Ile Tyr Ala Asp Lys Lys Ser Met Asp
            1955                1960                1965

Asp Gln Glu Lys Arg Ser Leu Ala Phe Glu Glu Gly Ser Gln Ser Thr
            1970                1975                1980

Thr Ile Ser Ser Leu Ser Glu Lys Ser Lys Glu Glu Thr Gly Ile Ser
1985                1990                1995                2000

Leu Gln Asp Leu Leu Leu Glu Ile Tyr Arg Ser Ile Gly Glu Pro Asp
                2005                2010                2015

Ser Leu Tyr Gly Cys Gly Gly Gly Lys Met Leu Gln Pro Ile Thr Arg
            2020                2025                2030

Leu Arg Thr Tyr Glu His Glu Ala Met Trp Gly Lys Ala Leu Val Thr
            2035                2040                2045

Tyr Asp Leu Glu Thr Ala Ile Pro Ser Ser Thr Arg Gln Ala Gly Ile
2050                2055                2060

Ile Gln Ala Leu Gln Asn Leu Gly Leu Cys His Ile Leu Ser Val Tyr
2065                2070                2075                2080

Leu Lys Gly Leu Asp Tyr Glu Asn Lys Asp Trp Cys Pro Glu Leu Glu
                2085                2090                2095

Glu Leu His Tyr Gln Ala Ala Trp Arg Asn Met Gln Trp Asp His Cys
            2100                2105                2110

Thr Ser Val Ser Lys Glu Val Glu Gly Thr Ser Tyr His Glu Ser Leu
            2115                2120                2125

Tyr Asn Ala Leu Gln Ser Leu Arg Asp Arg Glu Phe Ser Thr Phe Tyr
            2130                2135                2140

Glu Ser Leu Lys Tyr Ala Arg Val Lys Glu Val Glu Glu Met Cys Lys
2145                2150                2155                2160

Arg Ser Leu Glu Ser Val Tyr Ser Leu Tyr Pro Thr Leu Ser Arg Leu
                2165                2170                2175

Gln Ala Ile Gly Glu Leu Glu Ser Ile Gly Glu Leu Phe Ser Arg Ser
            2180                2185                2190

Val Thr His Arg Gln Leu Ser Glu Val Tyr Ile Lys Trp Gln Lys His
            2195                2200                2205

Ser Gln Leu Leu Lys Asp Ser Asp Phe Ser Phe Gln Glu Pro Ile Met
            2210                2215                2220

Ala Leu Arg Thr Val Ile Leu Glu Ile Leu Met Glu Lys Glu Met Asp
2225                2230                2235                2240

Asn Ser Gln Arg Glu Cys Ile Lys Asp Ile Leu Thr Lys His Leu Val
                2245                2250                2255

Glu Leu Ser Ile Leu Ala Arg Thr Phe Lys Asn Thr Gln Leu Pro Glu
            2260                2265                2270

Arg Ala Ile Phe Gln Ile Lys Gln Tyr Asn Ser Val Ser Cys Gly Val
            2275                2280                2285

Ser Glu Trp Gln Leu Glu Glu Ala Gln Val Phe Trp Ala Lys Lys Glu
            2290                2295                2300

Gln Ser Leu Ala Leu Ser Ile Leu Lys Gln Met Ile Lys Lys Leu Asp
2305                2310                2315                2320
```

```
Ala Ser Cys Ala Ala Asn Asn Pro Ser Leu Lys Leu Thr Tyr Thr Glu
            2325                2330                2335
Cys Leu Arg Val Cys Gly Asn Trp Leu Ala Glu Thr Cys Leu Glu Asn
            2340                2345                2350
Pro Ala Val Ile Met Gln Thr Tyr Leu Glu Lys Ala Val Glu Val Ala
            2355                2360                2365
Gly Asn Tyr Asp Gly Glu Ser Ser Asp Glu Leu Arg Asn Gly Lys Met
            2370                2375                2380
Lys Ala Phe Leu Ser Leu Ala Arg Phe Ser Asp Thr Gln Tyr Gln Arg
2385                2390                2395                2400
Ile Glu Asn Tyr Met Lys Ser Ser Glu Phe Glu Asn Lys Gln Ala Leu
            2405                2410                2415
Leu Lys Arg Ala Lys Glu Glu Val Gly Leu Leu Arg Glu His Lys Ile
            2420                2425                2430
Gln Thr Asn Arg Tyr Thr Val Lys Val Gln Arg Glu Leu Glu Leu Asp
            2435                2440                2445
Glu Leu Ala Leu Arg Ala Leu Lys Glu Asp Arg Lys Arg Phe Leu Cys
            2450                2455                2460
Lys Ala Val Glu Asn Tyr Ile Asn Cys Leu Leu Ser Gly Glu His
2465                2470                2475                2480
Asp Met Trp Val Phe Arg Leu Cys Ser Leu Trp Leu Glu Asn Ser Gly
            2485                2490                2495
Val Ser Glu Val Asn Gly Met Met Lys Arg Asp Gly Met Lys Ile Pro
            2500                2505                2510
Thr Tyr Lys Phe Leu Pro Leu Met Tyr Gln Leu Ala Ala Arg Met Gly
            2515                2520                2525
Thr Lys Met Met Gly Gly Leu Gly Phe His Glu Val Leu Asn Asn Leu
            2530                2535                2540
Ile Ser Arg Ile Ser Met Asp His Pro His His Thr Leu Phe Ile Ile
2545                2550                2555                2560
Leu Ala Leu Ala Asn Ala Asn Arg Asp Glu Phe Leu Thr Lys Pro Glu
            2565                2570                2575
Val Ala Arg Arg Ser Arg Ile Thr Lys Asn Val Pro Lys Gln Ser Ser
            2580                2585                2590
Gln Leu Asp Glu Asp Arg Thr Glu Ala Ala Asn Arg Ile Ile Cys Thr
            2595                2600                2605
Ile Arg Ser Arg Arg Pro Gln Met Val Arg Ser Val Glu Ala Leu Cys
            2610                2615                2620
Asp Ala Tyr Ile Ile Leu Ala Asn Leu Asp Ala Thr Gln Trp Lys Thr
2625                2630                2635                2640
Gln Arg Lys Gly Ile Asn Ile Pro Ala Asp Gln Pro Ile Thr Lys Leu
            2645                2650                2655
Lys Asn Leu Glu Asp Val Val Pro Thr Met Glu Ile Lys Val Asp
            2660                2665                2670
His Thr Gly Glu Tyr Gly Asn Leu Val Thr Ile Gln Ser Phe Lys Ala
            2675                2680                2685
Glu Phe Arg Leu Ala Gly Gly Val Asn Leu Pro Lys Ile Ile Asp Cys
            2690                2695                2700
Val Gly Ser Asp Gly Lys Glu Arg Arg Gln Leu Val Lys Gly Arg Asp
2705                2710                2715                2720
Asp Leu Arg Gln Asp Ala Val Met Gln Gln Val Phe Gln Met Cys Asn
            2725                2730                2735
```

```
Thr Leu Leu Gln Arg Asn Thr Glu Thr Arg Lys Arg Lys Leu Thr Ile
            2740                2745                2750

Cys Thr Tyr Lys Val Val Pro Leu Ser Gln Arg Ser Gly Val Leu Glu
            2755                2760                2765

Trp Cys Thr Gly Thr Val Pro Ile Gly Glu Phe Leu Val Asn Asn Glu
            2770                2775                2780

Asp Gly Ala His Lys Arg Tyr Arg Pro Asn Asp Phe Ser Ala Phe Gln
2785                2790                2795                2800

Cys Gln Lys Lys Met Met Glu Val Gln Lys Lys Ser Phe Glu Glu Lys
            2805                2810                2815

Tyr Glu Val Phe Met Asp Val Cys Gln Asn Phe Gln Pro Val Phe Arg
            2820                2825                2830

Tyr Phe Cys Met Glu Lys Phe Leu Asp Pro Ala Ile Trp Phe Glu Lys
            2835                2840                2845

Arg Leu Ala Tyr Thr Arg Ser Val Ala Thr Ser Ser Ile Val Gly Tyr
            2850                2855                2860

Ile Leu Gly Leu Gly Asp Arg His Val Gln Asn Ile Leu Ile Asn Glu
2865                2870                2875                2880

Gln Ser Ala Glu Leu Val His Ile Asp Leu Gly Val Ala Phe Glu Gln
            2885                2890                2895

Gly Lys Ile Leu Pro Thr Pro Glu Thr Val Pro Phe Arg Leu Thr Arg
            2900                2905                2910

Asp Ile Val Asp Gly Met Gly Ile Thr Gly Val Glu Gly Val Phe Arg
            2915                2920                2925

Arg Cys Cys Glu Lys Thr Met Glu Val Met Arg Asn Ser Gln Glu Thr
            2930                2935                2940

Leu Leu Thr Ile Val Glu Val Leu Leu Tyr Asp Pro Leu Phe Asp Trp
2945                2950                2955                2960

Thr Met Asn Pro Leu Lys Ala Leu Tyr Leu Gln Gln Arg Pro Glu Asp
            2965                2970                2975

Glu Thr Glu Leu His Pro Thr Leu Asn Ala Asp Asp Gln Glu Cys Lys
            2980                2985                2990

Arg Asn Leu Ser Asp Ile Asp Gln Ser Phe Asp Lys Val Ala Glu Arg
            2995                3000                3005

Val Leu Met Arg Leu Gln Glu Lys Leu Lys Gly Val Glu Glu Gly Thr
            3010                3015                3020

Val Leu Ser Val Gly Gly Gln Val Asn Leu Leu Ile Gln Gln Ala Ile
3025                3030                3035                3040

Asp Pro Lys Asn Leu Ser Arg Leu Phe Pro Gly Trp Lys Ala Trp Val
            3045                3050                3055
```

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
His Glu Pro Ala Asn Ser Ser Ala Ser Gln Ser Thr Asp Leu Cys
1               5                   10                  15
```

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Cys Lys Arg Asn Leu Ser Asp Ile Asp Gln Ser Phe Asp Lys Val
1               5                   10                  15

(2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Pro Glu Asp Glu Thr Glu Leu His Pro Thr Leu Asn Ala Asp Asp Gln
1               5                   10                  15

Glu Cys (2) INFORMATION FOR SEQ ID NO:7:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Cys Lys Ser Leu Ala Ser Phe Ile Lys Lys Pro Phe Asp Arg Gly Glu
1               5                   10                  15

Val Glu Ser Met Glu Asp Asp Thr Asn Gly
            20                  25

(2) INFORMATION FOR SEQ ID NO:8:

(i) SEQUENCE CHARACTERISTICS:
        (A) LENGTH: 3607 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (ix) FEATURE:
        (A) NAME/KEY: 3'UTR
        (B) LOCATION: 1..3607

(xi) SEQUENCE DESCRIPTION: SEQ ID NO:8:

TCTTCAGTAT ATGAATTACC CTTTCATTCA GCCTTTAGAA ATTATATTTT AGCCTTTATT      60

TTTAACCTGC CAACATACTT TAAGTAGGGA TTAATATTTA AGTGAACTAT TGTGGGTTTT     120

TTTGAATGTT GGTTTTAATA CTTGATTTAA TCACCACTCA AAAATGTTTT GATGGTCTTA     180

AGGAACATCT CTGCTTTCAC TCTTTAGAAA TAATGGTCAT TCGGGCTGGG CGCAGCGGCT     240

CACGCCTGTA ATCCCAGCAC TTTGGGAGGC CGAGGTGAGC GGATCACAAG GTCAGGAGTT     300

-continued

```
CGAGACCAGC CTGGCCAAGA GACCAGCCTG GCCAGTATGG TGAAACCCTG TCTCTACTAA      360
AAATACAAAA ATTAGCCGAG CATGGTGGCG GGCACCTGTA ATCCCAGCTA CTCGAGAGGC      420
TGAGGCAGGA GAATCTCTTG AACCTGGGAG GTGAAGGTTG CTGTGGGCCA AAATCATGCC      480
ATTGCACTCC AGCCTGGGTG ACAAGAGCGA AACTCCATCT CAAAAAAAAA AAAAAAAAAC      540
AGAAACTTAT TTGGATTTTT CCTAGTAAGA TCACTCAGTG TTACTAAATA ATGAAGTTGT      600
TATGGAGAAC AAATTTCAAA GACACAGTTA GTGTAGTTAC TATTTTTTTA AGTGTGTATT      660
AAAACTTCTC ATTCTATTCT CTTTATCTTT TAAGCCCTTC TGTACTGTCC ATGTATGTTA      720
TCTTTCTGTG ATAACTTCAT AGATTGCCTT CTAGTTCATG AATTCTCTTG TCAGATGTAT      780
ATAATCTCTT TTACCCTATC CATTGGGCTT CTTCTTTCAG AAATTGTTTT TCATTTCTAA      840
TTATGCATCA TTTTTCAGAT CTCTGTTTCT TGATGTCATT TTTAATGTTT TTTTAATGTT      900
TTTTATGTCA CTAATTATTT TAAATGTCTG TACCTGATAG ACACTGTAAT AGTTCTATTA      960
AATTTAGTTC CTGCTGTTTA TATCTGTTGA TTTTTGTATT TGATAGGCTG TTCATCCAGT     1020
TTTGTCTTTT TGAAAAGTGA GTTTATTTTC AGCAAGGCTT TATCTATGGG AATCTTGAGT     1080
GTCTGTTTAT GTCATATTCC CAGGGCTGTT GCTGCACACA AGCCCATTCT TATTTTAATT     1140
TCTTGGCTTT AGGGTTTCCA TACCTGAAGT GTAGCATAAA TACTGATAGG AGATTTCCCA     1200
GGCCAAGGCA AACACACTTC CTCCTCATCT CCTTGTGCTA GTGGGCAGAA TATTTGATTG     1260
ATGCCTTTTT CACTGAGAGT ATAAGCTTCC ATGTGTCCCA CCTTTATGGC AGGGGTGGAA     1320
GGAGGTACAT TTAATTCCCA CTGCCTGCCT TTGGCAAGCC CTGGGTTCTT TGCTCCCCAT     1380
ATAGATGTCT AAGCTAAAAG CCGTGGGTTA ATGAGACTGG CAAATTGTTC CAGGACAGCT     1440
ACAGCATCAG CTCACATATT CACCTCTCTG GTTTTTCATT CCCCTCATTT TTTTCTGAGA     1500
CAGAGTCTTG CTCTGTCACC CAGGCTGGAG TGCAGTGGCA TGATCTCAGC TCACTGAAAC     1560
CTCTGCCTCC TGGGTTCAAG CAATTCTCCT GCCTCAGCCT CCCGAGTAGC TGGGACTACA     1620
GGCGTGTGCC AACACGCCCG GCTAATTTTT TGTATTTTTA TTAGAGACGG AGTTTCACCG     1680
TGTTAGCCAG GATGGTCTCG ATCGCTTGAC CTCGTGATCC ACCCTCCTCG GCCTCCCAAA     1740
GTGCTGGGAT TACAGGTGTG AGCCACCGCG CCCGGCCTCA TTCCCCTCAT TTTTGACCGT     1800
AAGGATTTCC CCTTTCTTGT AAGTTCTGCT ATGTATTTAA AAGAATGTTT CTACATTTT     1860
ATCCAGCATT TCTCTGTGTT CTGTTGGAAG GGAAGGGCTT AGGTATCTAG TTTGATACAT     1920
AGGTAGAAGT GGAACATTTC TCTGTCCCCC AGCTGTCATC ATATAAGATA AACATCAGAT     1980
AAAAAGCCAC CTGAAAGTAA AACTACTGAC TCGTGTATTA GTGAGTATAA TCTCTTCTCC     2040
ATCCTTAGGA AAATGTTCAT CCCAGCTGCG GAGATTAACA AATGGGTGAT TGAGCTTTCT     2100
CCTCGTATTT GGACCTTGAA GGTTATATAA ATTTTTTTCT TATGAAGAGT TGGCATTTCT     2160
TTTTATTGCC AATGGCAGGC ACTCATTCAT ATTTGATCTC CTCACCTTCC CCTCCCCTAA     2220
AACCAATCTC CAGAACTTTT TGGACTATAA ATTTCTTGGT TTGACTTCTG GAGAACTGTT     2280
CAGAATATTA CTTTGCATTT CAAATTACAA ACTTACCTTG GTGTATCTTT TTCTTACAAG     2340
CTGCCTAAAT GAATATTTGG TATATATTGG TAGTTTTATT ACTATAGTAA ATCAAGGAAA     2400
TGCAGTAAAC TTAAAATGTC TTTAAGAAAG CCCTGAAATC TTCATGGGTG AAATTAGAAA     2460
TTATCAACTA GATAATAGTA TAGATAAATG AATTTGTAGC TAATTCTTGC TAGTTGTTGC     2520
ATCCAGAGAG CTTTGAATAA CATCATTAAT CTACTCTTTA GCCTTGCATG GTATGCTATG     2580
AGGCTCCTGT TCTGTTCAAG TATTCTAATC AATGGCTTTG AAAAGTTTAT CAAATTTACA     2640
```

-continued

```
TACAGATCAC AAGCCTAGGA GAAATAACTA ATTCACAGAT GACAGAATTA AGATTATAAA      2700

AGATTTTTTT TTGGTAATTT TAGTAGAGAC AGGGTTGCCA TTGTATTCCA GCCTTGGCGA      2760

CAGAGCAAGA CTCTGCCTCA AAAAAAAAAA AAAAAAGGTT TTGCCAAGCT GGAACTCTTT      2820

CTGCAAATGA CTAAGATAGA AAACTGCCAA GGACAAATGA GGAGTAGTTA GATTTTGAAA      2880

ATATTAATCA TAGAATAGTT GTTGTATGCT AAGTCACTGA CCCATATTAT GTACAGCATT      2940

TCTGATCTTT ACTTTGCAAG ATTAGTGATA CTATGCCAAT ACACTGCTGG AGAAATCAGA      3000

ATTTGGAGAA ATAAGTTGTC CAAGGCAAGA AGATAGTAAA TTATAAGTAC AAGTGTAATA      3060

TGGACAGTAT CTAACTTGAA AAGATTTCAG GCGAAAAGAA TCTGGGGTTT GCCAGTCAGT      3120

TGCTCAAAAG GTCAATGAAA ACCAAATAGT GAAGCTATCA GAGAAGCTAA TAAATTATAG      3180

ACTGCTTGAA CAGTTGTGTC CAGATTAAGG GAGATAATAG CTTTCCCACC CTACTTTGTG      3240

CAGGTCATAC CTCCCCAAAG TGTTTACCTA ATCAGTAGGT TCACAAACTC TTGGTCATTA      3300

TAGTATATGC CTAAAATGTA TGCACTTAGG AATGCTAAAA ATTTAAATAT GGTCTAAAGC      3360

AAATAAAAGC AAAGAGGAAA AACTTTGGAC ATCGTAAAGA CTAGAATAGT CTTTTAAAAA      3420

GAAAGCCAGT ATATTGGTTT GAAATATAGA GATGTGTCCC AATTTCAAGT ATTTTAATTG      3480

CACCTTAATG AAATTATCTA TTTTCTATAG ATTTTAGTAC TATTGAATGT ATTACTTTAC      3540

TGTTACCTGA ATTTATTATA AAGTGTTTTT GAATAAATAA TTCTAAAAGC AAAAAAAAAA      3600

AAAAAAA                                                                3607

(2) INFORMATION FOR SEQ ID NO:9:

(i) SEQUENCE CHARACTERISTICS:
        (A) LENGTH: 884 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (ix) FEATURE:
        (A) NAME/KEY: 5'UTR
        (B) LOCATION: 1..884

(xi) SEQUENCE DESCRIPTION: SEQ ID NO:9:

TCCTCCTTTT AAACGCCCTG AATTGAACCC TGCCTCCTGC GCATCCTCTT TTTGTGTCAC        60

CTTAGGGTTC AGATTTAACT ACGCGACTTG ACTAGTCATC TTTTGATCTC TCTCTCGTAT       120

TTAGTACTTT TAGTCAGCGA GCATTTATTG ATATTTCAAC TTCAGCCTCG CGGTTAAGAG       180

CTTGGGCTCT GGAATCATAC GGCTGGAATT GGAATTCTGT CAGTCGTGTG GCCGCTCTCT       240

ACTGTCTTGT GAAGATAAGT GAGATAATCT TGACCTGTGG TGAGCACTCG TGAGCGTTAG       300

CTGCTGTATT TACCAGGTAC AGATAAGACA ACTACAGTGG ATGATAATGT ATGTGGTGAT       360

AGGGAGTAC TCTGATGGTA GAGGAGTGAC TTTGGTTCTC TGCAAACTCA GCCTGAGACT        420

ATCAATTCAG TTTGTGGTGA GACCTCGCAG TGTTACCTTG GCAGATGGTA GAAGCCTTCC       480

AGATGGAAGG AAAAATGCGT GTAAAGGCAC AAAGTGTAGA AGGACCCTGA AGCTCCAGCG       540

TGAGGCCTGG CATTGAATGA AATATATTTT GTGGGTTTTC AGCTGCTGAA GTCATAGGAA       600

TGGATGAGAC CAAGAAAACA AAGCTGTTTT TGAGGTATGA GCGGAAGAAG AGATATCAGG       660

AGACTTTCGA AACAGTCATA ACGGAAGTTA ATATGATCAT TGCTAACATT TGCTGTGTTT       720

CAGGCACTGT AAGCATGTAT ATGGGTCCTT AAAGGGACTC ATAGAGAGGC ATACATCACA       780
```

```
ATTTGGAATT ATGCATTGGT TTATCAATTT ACTTGTTTAT TGTCACCCTG CTGCCCAGAT    840

ATGACTTCAT GAGGACAGTG ATGTGTGTTC TGAAATTGTG AACC                    884

(2) INFORMATION FOR SEQ ID NO:10:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

AGGTAGCTGC GTGGCTAACG GAGAAAAGAA GCCGTGGCCA CGGGAGGAGG CGAGAGGAGT     60

CGGGATCTGC GCTGCAGCCA CCGCCGCGGT TGATACTACT TTGACCTTCC GAGTGCAGTG    120

(2) INFORMATION FOR SEQ ID NO:11:

(i) SEQUENCE CHARACTERISTICS:
        (A) LENGTH: 198 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..88

(xi) SEQUENCE DESCRIPTION: SEQ ID NO:11:

AGGCATACAT CACAATTTGG AATTATGCAT TGGTTTATCA ATTTACTTGT TTATTGTCAC     60

CCTGCTGCCC AGATATGACT TCATGAGGGT AGGATTTGTA TCTGTTTAGT TCATTATTTG    120

TCTAGCTATA AGTAGTAAAT ATTGTTTGCA ACTATCAGTG AATGAGCATC TTCTGTTTAT    180

GTAGATAATA CTGAACTG                                                 198

(2) INFORMATION FOR SEQ ID NO:12:

(i) SEQUENCE CHARACTERISTICS:
        (A) LENGTH: 750 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TTACAGCATT ACTTGTATAG ATTTTAAGGA GATCTCATTT TAAATACGGA AATGTTAAGA     60

AAAATTATTG TGCCTTTGAC CAGAATGTGC CTCTAATTGT ACAGATAAAT CTAACTATAA    120

ATGCTGCAGT ATAAAATAAT TACATACACA TTTTTTCACA CCTCTTTCTC TCTATATATG    180

CATATATACA TACACATATA TATACCTATA TGTATTTTTT TTACAGACAG TGATGTGTGT    240

TCTGAAATTG TGAACCATGA GTCTAGTACT TAATGATCTG CTTATCTGCT GCCGTCAACT    300

AGAACATGAT AGAGCTACAG AACGAAAGGT AGTAAATTAC TTAAATTCAA TTTTTCCTTG    360

AAATGTGTGA TTAGTAACCC ATTATTATTT CCTTTTTATT TTCAGAAAGA AGTTGAGAAA    420

TTTAAGCGCC TGATTCGAGA TCCTGAAACA ATTAAACATC TAGATCGGCA TTCAGATTCC    480

AAACAAGGAA AATATTTGAA TTGGGATGCT GTTTTTAGGT ATTCTATTCA AATTTATTTT    540

ACTGTCTTTA TTTTTCTCTT TCATATTTAT TTCTGTTGTG ATATTACTTT TGTGTGTAAG    600
```

```
TCTTAACATT TATCTTTGAT TCCTATATAT CATTATGCCT TGCATATGAA TTTGGCATTT      660

AATATTTATC CAAAACATAA TTTTTAAAGG TTGTTCATAT AGAAACTTAA AAATTATAAA      720

TTATTTCTTC AATAAAATGT TTTAGACATA                                      750
```

(2) INFORMATION FOR SEQ ID NO:13:

(i) SEQUENCE CHARACTERISTICS:
        (A) LENGTH: 388 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
GCAGTAAAGC AATAGAAAGT CATAGAAGAT TAAGAGCTTT GCAGACCAGA TATTAAATTG       60

GTCTTGTAGG AGTTAGGCCT TGAAAGAGAG ATTTAATTGT TTTATTTGTT TTTTTCAGCT      120

GATGTAGTAA TCTAAGCAAG GTGGTTTAAA AGTTGCTCTT TGTGATGGCA TGAACAGCTT      180

TTGAAATTAT TATAATTTAA GTATTCAACG AGTTTCTGAA ATTGCATTTT GTTTTCTTGA      240

AGATTTTTAC AGAAATATAT TCAGAAAGAA ACAGAATGTC TGAGAATAGC AAAACCAAAT      300

GTATCAGCCT CAACACAAGC CTCCAGGCAG AAAAAGATGC AGGAAATCAG TAGTTTGGTC      360

AAATACTTCA TCAAATGTGC AAACAGAA                                        388
```

(2) INFORMATION FOR SEQ ID NO:14:

(i) SEQUENCE CHARACTERISTICS:
        (A) LENGTH: 349 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
GAGCACCTAG GCTAAAATGT CAAGAACTCT TAAATTATAT CATGGATACA GTGAAAGATT       60

CATCTAATGG TGCTATTTAC GGAGCTGATT GTAGCAACAT ACTACTCAAA GACATTCTTT      120

CTGTGAGAAA ATACTGGTGT GAAATATCTC AGCAACAGTG GTTAGGTATG TTTTGAAGGT      180

TGTTGTTTGT GAATTTTTCC TCATGAAATG AAACTTCACC AAAGAAAGCA CTCTGTCTGT      240

ATCTGTCTAT ATCCCCCAAG TGACCTGACA GGTTTAACAG TACTTTAGTA AAATTATATG      300

GTTATCGAAC TGACCCTTAA TTTTTATTTA TTATGTAGCT TTTGAATAA                 349
```

(2) INFORMATION FOR SEQ ID NO:15:

(i) SEQUENCE CHARACTERISTICS:
        (A) LENGTH: 388 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
AATTGTTCTC TGTGTACTTC AGGCTCTATC TGAAACCTTC ACAAGATGTT CATAGAGTTT       60

TAGTGGCTAG AATAATTCAT GCTGTTACCA AAGGATGCTG TTCTCAGACT GACGGATTAA      120

ATTCCAAATT TTTGGACTTT TTTTCCAAGG CTATTCAGTG TGCGAGGTAA TCTAATCTCT      180

TTTTCTTTGT TTTGTATTGA AATACTTTTG ATCTTGCAAG ACCATGTTTT AGACTCAGTA      240
```

```
ACTAAAAATT CTACCTTAAA ATAAAACATT GATCCATCAT AACAGAACTA GTGGATTCCT      300

AAAGAGACAA CCAAGTCCAA CACTTTCTGA ATATCCAATA TGCAGAACAC TACGTGAAGT      360

TTTCAAGGGG GAGATGTGTC TTGCTGAT                                        388
```

(2) INFORMATION FOR SEQ ID NO:16:

(i) SEQUENCE CHARACTERISTICS:
        (A) LENGTH: 611 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
ACAGAGTGGT CTCTTACACC AAATAAGAAC TAATTTTTTG TCAGTGTGAA GTAATGCTGT       60

GATTTTTTTT TTAATGAATA GTTTTGAAAT TAAGACTACT GTTTGAAAAT TAGGGTTTTG      120

TTTTTTTTTC TTTCAGCATA CCACTTCATA ACTGTTCAGT TTGTACAGTT TGTTCCCCCT      180

GTTATACCCA GTTGAGCTTG TTTGTTTCTT CACAGACAAG AAAAGAGCTC TTCAGGTCTA      240

AATCATATCT TAGCAGCTCT TACTATCTTC CTCAAGACTT TGGCTGTCAA CTTTCGAATT      300

CGAGTGTGTG AATTAGGAGA TGAAATTCTT CCCACTTTGC TTTATATTTG GACTCAACAT      360

AGGCTTAATG ATTCTTTAAA AGAAGTCATT ATTGAATTAT TTCAACTGCA AATTTATATC      420

CATCATCCGA AAGGAGCCAA AACCCAAGAA AAAGGTATAA AGGAAATGTT TACTGTTTTG      480

AATTTGCTTC TTCATTCAAA CATAGAAGTC TAAGTATAAA ATTAGTGTTC TTTAGGAGGA      540

TATGACTTTC CTCTGGATTT CTCTGGTTGA TAATGTTACT TAGCCATGAG AATGTTTTTC      600

ATAGAGTTTT T                                                          611
```

(2) INFORMATION FOR SEQ ID NO:17:

(i) SEQUENCE CHARACTERISTICS:
        (A) LENGTH: 448 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
GTGCTTATGA ATCAACAAAA TGGAGAAGTA TTTTATACAA CTTATATGAT CTGCTAGTGA       60

ATGAGATAAG TCATATAGGA AGTAGAGGAA AGTATTCTTC AGGATTTCGT AATATTGCCG      120

TCAAAGAAAA TTTGATTGAA TTGATGGCAG ATATCTGTCA CCAGGTACAG TAAGTAGGTC      180

ATGTCACATT TAGAAATTTC CTGTTAATTT TTTTTTTAAA CTGGGCATTT GGGCTTTTAA      240

AACCTGTGTT CTCACAAAAA GCCTATAAAA TGACTCTGTA CATGCAACTA TTCCTTTCAA      300

ACTATCAGAA ATATTTGGAA TTACCCTTTT AACTTAAAAG TTAATGCTTT TGCAGATATT      360

TGAAAACTAA CAATGAACTT TTTCATTCTT AAATGATTGT CTCTAGGAAA TAAGGTGACC      420

CTAACCCTAA TGATTCGATT CGACTCGA                                        448
```

(2) INFORMATION FOR SEQ ID NO:18:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
GGTTGTGGTT ATACGAGATC GTGCTGTTCC ACTCCAACCT GGGCAACAAC AGCGAAATCT        60
GGCTCAAAAA AAAAAAAAAA GAAAAAAGTG GATTTATTTT TATTTTACAG GTTTTTAATG       120
AAGATACCAG ATCCTTGGAG ATTTCTCAAT CTTACACTAC TACACAAAGA GAATCTAGTG       180
ATTACAGTGT CCCTTGCAAA AGGAAGAAAA TAGAACTAGG CTGGGAAGTA ATAAAAGATC       240
ACCTTCAGAA GTCACAGAAT GATTTTGATC TTGTGCCTTG GTAAAGTGTT ACCATTTTCT       300
CATTCAGTGT CATTTTAATC TCTTGTATGT TATTTTTCAG AAAACTTTCA GTGGAATCCT       360
TTCATCTCAA CCAGAACTAA GTCATTTGTC TACCCCCAAA CCTATTACTA GCAAAGGGAT       420
ATGTGATTGC CATGACAAAT GAGATCAATC ATTAATGGCT CATTTGCTTG GGCCAAGTGC       480
AGGGCCACCT ATTTTAATCA                                                    500
```

(2) INFORMATION FOR SEQ ID NO:19:

(i) SEQUENCE CHARACTERISTICS:
        (A) LENGTH: 748 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
AACTATTAAC AGCCAGTTTA TTTTTAGAGT ACTATGGAAA TGATGGTGAT TTCTAATTAG        60
GATATTGTAA GAGTACCATG TCTATATATT TCCTTTTAGT TTGTTAATGT GATGGAATAG       120
TTTTCAAATA TCCTTTTTTT TTTTTTTTTA GGCTACAGAT TGCAACCCAA TTAATATCAA       180
AGTATCCTGC AAGTTTACCT AACTGTGAGC TGTCTCCATT ACTGATGATA CTATCTCAGC       240
TTCTACCCCA ACAGCGACAT GGGGAACGTA CACCATATGT GTTACGATGC CTTACGGAAG       300
TTGCATTGTG TCAAGACAAG AGGTCAAACC TAGAAAGCTC ACAAAAGTCA GATTTATTAA       360
AACTCTGGAA TAAAATTTGG TGTATTACCT TTCGTGGTAT AAGTTCTGAG CAAATACAAG       420
CTGAAAACTT TGGCTTACTT GGAGCCATAA TTCAGGGTAG TTTAGTTGAG GTTGACAGAG       480
AATTCTGGAA GTTATTTACT GGGTCAGCCT GCAGACCTTC ATGGTAAGTT CAGCATGCAT       540
TATGTCTGAC TTCAGATAA ACACACACAG ACACACACAC ACTCACATAT CCCTGATCAT        600
TTCCATAGTT TGTTACTTCA GTTAAAGATG TCAAATTCTA TTTCAGATGC TTTTCTTGTT       660
TGGCCGAGAA GACTTAATAA ATGCATAAGT GAATTTAGTT TCAAATGTTG ACAAATTATT       720
AAAGACTAAT GTTAAGGAAT TTCTTTTT                                           748
```

(2) INFORMATION FOR SEQ ID NO:20:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
AGAATTATGA AGAGTTTAAA TTTCTTTTAT GTGCAATTTA TCATTATTTA TTAAATAGCC        60
ATGTTTAAAT TGTAGTACTA TGCACTGTTA ATAAACGAGC TATTTTTTAA TCAAGAATCT       120
```

```
TCCCAAATGT AATCAGACTT TTAACAGTTT TTATGTTCAT TTAGTCACCT TAACTAAATG      180

TATGTGCCAG GCACTGTCCT GATAGATAAA GTCTTTGCCC CTCCAATAGC TTGCTTTTCA      240

CAATTGTCCT TTGTTTTGTT ATAGTCCTGC AGTATGCTGT TTGACTTTGG CACTGACCAC      300

CAGTATAGTT CCAGGAACGG TAAAAATGGG AATAGAGCAA AATATGTGTG AAGTAAATAG      360

AAGCTTTTCT TTAAAGGAAT CAATAATGAA ATGGCTCTTA TTCTATCAGT TAGAGGGTGA      420

CTTAGAAAAT AGCACAGAAG TGCCTCCAAT TCTTCACAGG TAATTTAAGT TCATTAGCAT      480

GCTGCTGTTT TTTTTGTTTG TTTTATCAGG CTCTCTCCAC TTATTTGATG CCAGATGGCT      540

TTATTTTATA ATAATAATGC AGAATTTCCC AGATCTAACC TTAATTATTA AATATTATGT      600

TTGTTTTTAC AGTTATCTGT GTCTTTATGC CTGATTGCTT CTGAAATAAA GGGTTGTCTC      660

ACTGTGAGAA TATGGGGGAT GTGCATGAAA AATGCACAT                             699

(2) INFORMATION FOR SEQ ID NO:21:

(i) SEQUENCE CHARACTERISTICS:
        (A) LENGTH: 548 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

TGGATCCAAT TAAAGTACTT TTGCTTTAAT TTTACAACCT TTTATTTATT TCAGAAATAA       60

TGTTAAACAT GCTGTTTCTA AACAGTATTG GAAATGATAA TAACAATGGT TGTCCTCCTT      120

AAATTGTCCT TTTAGATATT AAGAAATTTA GTATAGATGA AAGCAATTTT AATCTAGGAT      180

CCAAATTTTA GAAGTCAAGA TTTATAGCTA AACATGGATG TTAAAGTTTA AAGTATTCTT      240

TACATGGCTT TTGGTCTTCT AAGTGAAGCT TTTTGTTTTT CTTTGTAGTA ATTTTCCTCA      300

TCTTGTACTG GAGAAAATTC TTGTGAGTCT CACTATGAAA AACTGTAAAG CTGCAATGAA      360

TTTTTTCCAA AGCGTGCCAG AATGGTATGT TATCTAATAA TGCTCTTTAT CATTTTAAGC      420

TATAGCTTTA ATTACAAAGA TGATAATTTT CGCTGGGTAG TAGCTGCATC TTAATAAGGT      480

CACCTAACTT GGTCCAAAAA AATTGCAACT GTTAGCCAGG GAAGAGGTTG TTTTAATTCA      540

GTGATTGT                                                              548

(2) INFORMATION FOR SEQ ID NO:22:

(i) SEQUENCE CHARACTERISTICS:
        (A) LENGTH: 637 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

TTTCTACTGA ATAATGACAT TTGATATAAG TAGGTCTCAA AGTCCGAAGA AGAGAAGGCA       60

TTTAAAAGAA TAATCTATTA ATTATATGAA GTAGTCTTTG AATGATGTAG ATACTAGGTT      120

AATGTTTTCC TTTGTAATAT ATTGCTAATA CATATAAGGC AAAGCATTAG GTACTTGGTT      180

TATATATTAA AGATCTTACT TTCTTGAAGT GAACACCACC AAAAAGATAA AGAAGAACTT      240

TCATTCTCAG AAGTAGAAGA ACTATTTCTT CAGACAACTT TTGACAAGAT GGACTTTTTA      300

ACCATTGTGA GAGAATGTGG TATAGAAAAG CACCAGTCCA GTATTGGCTT CTCTGTCCAC      360

CAGAATCTCA AGGAATCACT GGATCGCTGT CTTCTGGGAT TATCAGAACA GCTTCTGAAT      420
```

```
AATTACTCAT CTGAGGTGAG ATTTTTTAAA AAAAGAACTA AGCTTATATA TGATTCAACT      480

TTGGTAAACT GTTAGGAAGG AGAAATAGGG GCAGGAAAAA CAGCAAGGAT GGTGGGAGGC      540

TTCATTTTAA AAGCAAAGTG GCAGTAAAGG GCTCTAAATT GGACAACTTA GCATAATTAA      600

AGGAAAACTC AAGAATAATA ATTTGAGTAC TTCCTTT                               637

(2) INFORMATION FOR SEQ ID NO:23:

(i) SEQUENCE CHARACTERISTICS:
        (A) LENGTH: 568 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

CCATCAGGAG ATACTTAGGC TATTTTTCTT GAGAATCCTG GTTATAATTC TACAGTGATC       60

TCCTAGTTGT TTTTAGAGCT ATCCAGGATA TGCCACCTTT AACTCAGTTA ACTGAACTTT      120

TGTTTTTTAA TATGTATGTA GAATTTGTTC TTACAAAAGA TAGAGTATAC TAAATTATTT      180

ATGAAATATA TATATTTTTA TTTGTGGTTT ACTTTAAGAT TACAAATTCA GAAACTCTTG      240

TCCGGTGTTC ACGTCTTTTG GTGGGTGTCC TTGGCTGCTA CTGTTACATG GGTGTAATAG      300

CTGAAGAGGA AGCATATAAG TCAGAATTAT TCCAGAAAGC CAAGGTAGGA GAATTTATAC      360

TAATAAAGTT TCGGATAAAT TTGAATGAAA TGTATTCCTG TGAAAATTAT TACATTTGTT      420

TGGAAGACAT TAAATTGTAT GCAGGTTAAC CCTTTCTCTT TTATTTATGT AATGTGAGAA      480

GAAATTATAC TATGTATTTT TTAAATTGTT TTAATTGTTT AATTTTTAAT TATTATTATA      540

CTTTAAGTTC TGGGGTACAT GATGCAGA                                         568

(2) INFORMATION FOR SEQ ID NO:24:

(i) SEQUENCE CHARACTERISTICS:
        (A) LENGTH: 531 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

AAGATTTGCC ATTTTAAAAA ATTGTTAATG AGTTTTGCTT AAACTGTATG ACCACGTGGA       60

ACTTCTAAAA ACATTTCATT TTTTCTCTTA AGTGCACTTT ATTTTTTATT TTATAGTATG      120

TCCAAGATCA AAGTACACTG TAAAAAGCAA TACTAAACTA TAATTTTAAC TGGAATTTGC      180

ATTTTTCCTT CTATTCACAA TAGTCTCTAA TGCAATGTGC AGGAGAAAGT ATCACTCTGT      240

TTAAAAATAA GACAAATGAG GAATTCAGAA TTGGTTCCTT GAGAAATATG ATGCAGCTAT      300

GTACACGTTG CTTGAGCAAC TGTACCAAGG TAAGATTTTC TTCTTCTTGT TTTGTTTTTT      360

GAGATAGGAT CTTTCTCTGT CACCCAGGCT GGAGTGCAGT GGGATTGTCA CAACTCATTG      420

TAGCCTTGAC CTCCTGGTTT CCAGCAATTC TCCTGCCTCA GTCTCCCAAG TAATTGGGAC      480

TACAGGCATG TACCACCTAG CTAAAATTTT CTTTTTACTT GAAAGTGTAG C               531

(2) INFORMATION FOR SEQ ID NO:25:

(i) SEQUENCE CHARACTERISTICS:
        (A) LENGTH: 476 base pairs
        (B) TYPE: nucleic acid
```

```
            (C) STRANDEDNESS: single
            (D) TOPOLOGY: linear (ii) MOLECULE TYPE: DNA (genomic)

(xi) SEQUENCE DESCRIPTION: SEQ ID NO:25:

TGTTGTTAAA GCACAATGAA AGATGTACAG TATAGTTATT ATAACTCTAA GAAAAGATGT      60

GTTTTTGAAG CAGCATATAT ATTGGCCCTA ATAGTAAACT ATTTATCTAC ATTCCATTCA     120

AGATAGAGAA AACACTGTCT GCCAAGAATA ATTGTTTTTA TTTCTTTGTT GCTTGGTTCT     180

TTGTTTGTCT TAATTGCAGA AGAGTCCAAA TAAGATTGCA TCTGGCTTTT TCCTGCGATT     240

GTTAACATCA AAGCTAATGA ATGACATTGC AGATATTTGT AAAAGTTTAG TAAGTATGCT     300

TCCTGTTTTG CTATCATATT TTGATTCTAA TAGGCATAAT TTTTTTGTTG AAATATCTTT     360

GTAAATAAGG ATGCATCTCA CAACATATAG CTCTTAACAT TTTTACAAAT GTGGAAATTA     420

AGGCCAGGTG CGGTGGCTCA TGCCTGTAAC CCCAGCACTT TGGGAGGCCG AGGTGG         476

(2) INFORMATION FOR SEQ ID NO:26:

(i) SEQUENCE CHARACTERISTICS:
        (A) LENGTH: 634 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

TTACAGGTGC CCACCACCAC ACCCAGCTAA TTTTTGTATT TTAAATAGAG ACAAGGTTTC      60

ACCATGTTGG CCAGGCTGGT TTCGAACTCC CGACCTCAGG TGATCCACCT GGCTCAGCCT     120

CCCAAATTGC TGAGATTACA GATGTGAGCC ACTGTGCCCA GCCTGATTAG GTAAATTTTG     180

ACTACAGCAT GCTCCTGCAA GAAGCCATCT TGAACATCTT TGTTTCTCTT CCTTGAAGGC     240

ATCCTTCATC AAAAAGCCAT TTGACCGTGG AGAAGTAGAA TCAATGGAAG ATGATACTAA     300

TGGAAATCTA ATGGAGGTGG AGGATCAGTC ATCCATGAAT CTATTTAACG ATTACCCTGA     360

TAGTAGTGTT AGTGATGCAA ACGAACCTGG AGAGAGCCAA AGTACCATAG GTAAATACAT     420

ATTTACTACT TGGGATTTCT TTTACTTCTT TATATTGATT TGGCAGTATA AGAGGCCTCA     480

TTGATATCAA TTTTGTGCTT ATTTCATTTT CTCTTAGTAT AGCCTTTTAG GATTGTTCCT     540

TTCTTATATA CTTTATTTTT TTTTTATTTT TACTGGAATT TATTAGTTTC ATATTTTATC     600

CTCCATAGAA GGAACTTAAG ATAACTATTA AAGA                                 634

(2) INFORMATION FOR SEQ ID NO:27:

(i) SEQUENCE CHARACTERISTICS:
        (A) LENGTH: 593 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

TTTAAATTAT TTCTTGACAA CAGAATCTTG GATAATTTTT CAAAAAGACT TTTGAAGCTT      60

TCAGTATATA ATTAATTTCA CTATAATTTT GCTTTTCATA TACTTTTTTT TGTGAAGAGG     120

AGGAAATTTG AGTTAATATG ACTATATATG GCTGTTGTGC CCTTCTCTTA GTGTTAATGA     180

GTGCTTTTTA TTTTTAGGTG CCATTAATCC TTTAGCTGAA GAATATCTGT CAAAGCAAGA     240
```

```
TCTACTTTTC TTAGACATGC TCAAGTTCTT GTGTTTGTGT GTAACTACTG CTCAGACCAA      300

TACTGTGTCC TTTAGGGCAG CTGATATTCG GAGGAAATTG TTAATGTTAA TTGATTCTAG      360

CACGCTAGAA CCTACCAAAT CCCTCCACCT GCATATGGTG AGTTACGTTA AATGAAGAAG      420

CTCTTGGATT TTATCTGATG TTGCTGACTA AATGTAATGA GTTGACATGT AAGAATCACA      480

TGGTGTCTTT GAAGAATTGA AATTGCTTTC TTGAGAAATG AACCTGAGAC TAGTTGGAAA      540

ATAACACTTT TAACGTGCTG TGAGCAAATT TAAGTGGATG CTGAAATATT AAA             593

(2) INFORMATION FOR SEQ ID NO:28:

(i) SEQUENCE CHARACTERISTICS:
        (A) LENGTH: 769 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

AGGCGCCTGC CACCACCCCT GGCTAATTTT TGTGTTTTTA GTAGAGATGG AGTTTCACCA       60

TATTGGCCAG GCTGTTCTCA AACTCCTGAC CTTGTGATCT GCCTGCTTCA GCCTCCCAAA      120

GTGCTGGGAT TACAGGTTTG AGCCACTGCA CCCGGCCTAT GTTTATATAC TTTTTAAAGT      180

AAATGATTTG TGGATAAACC TGATTTTTTT CCCTCCTACC ATCTTAGTAT CTAATGCTTT      240

TAAAGGAGCT TCCTGGAGAA GAGTACCCCT TGCCAATGGA AGATGTTCTT GAACTTCTGA      300

AACCACTATC GTAAGAAATT AAAACCCTTA TGTTATGTTC ACTTTAAAGT TATAAAATAA      360

CTGATGTGTT CTTAAGCTTA ATAAAGTGGA ACTTTTTTTT TTTTTTTACC ACAGCAATGT      420

GTGTTCTTTG TATCGTCGTG ACCAAGATGT TTGTAAAACT ATTTTAAACC ATGTCCTTCA      480

TGTAGTGAAA AACCTAGGTC AAAGCAATAT GGACTCTGAG AACACAAGGG ATGCTCAAGG      540

ACAGTTTCTT ACAGTAATTG GAGCATTTTG GTAGGTACAG TCTATTTTGT GGTCCTATTT      600

TTCTTTTGCT ATCTGTGGAT ACGAATGCAA GTTTTGTATC CACATCAGTG ATTTCTTCTG      660

ATCTGCCTAC ATAGCTAATA CATCTGGAAA GAATAGCAGA ATGTTATTTG TGTTTCCCTC      720

AGTCGCTTGA AGAACTACAT TGCTTTTTGT TTAAGGCTTG GCTTTCTAA                  769

(2) INFORMATION FOR SEQ ID NO:29:

(i) SEQUENCE CHARACTERISTICS:
        (A) LENGTH: 712 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

ATTCCTTTTA CCACTAATTT CCTTTTAGCT TGAATTTTTG GCAAGGTGAG TATGTTGGCA       60

TATTCCACAT AATGACAAAT AAGTTTAGCA CAGAAAGACA TATTGGAAGT AACTTATAAT      120

AACCTTTCAG TGAGTTTTCT GAGTGCTTTT ATCAGAATGA TTATTTAACT TTGGAAAACT      180

TACTTGATTT CAGGCATCTA ACAAAGGAGA GGAAATATAT ATTCTCTGTA AGAATGGCCC      240

TAGTAAATTG CCTTAAAACT TTGCTTGAGG TGAGTTTTTG CATTTTTTTA GTAAGATCTC      300

CATTGAAAAT TTTAAAGCAG TCTTTGTTTG TTAATGAGTA ATTTTTCTCT ATTTCATATT      360

TAACCACAGT TCTTTTCCCG TAGGCTGATC CTTATTCAAA ATGGGCCATT CTTAATGTAA      420

TGGGAAAAGA CTTTCCTGTA AATGAAGTAT TTACACAATT TCTTGCTGAC AATCATCACC      480
```

```
AAGTTCGCAT GTTGGCTGCA GAGTCAATCA ATAGGTAATG GGTCAAATAT TCATGAAGTA      540

TTTGGAATGC TGCAGATGGC AGTAGAATGT CTTACATAGT AACAGCTCAC AGTTGCAATA      600

TTAAAAATAG CTAACACTTG TTGAGTATAT ACGGTGTGCC TGGCATTTAT GTTTATTCTT      660

AATTCTTATA CTTCTGTCAC TTAGATTCTA TTATTTCCTT CAATTTATAA AT             712

(2) INFORMATION FOR SEQ ID NO:30:

(i) SEQUENCE CHARACTERISTICS:
        (A) LENGTH: 508 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CTAAGCTGCT GGTCTGAACC TCTTTAAATA AACTCAGGTT TTGTTAGTCT TTAAGAAAGA       60

GCTAGTATGT TATTATGTCT CACAGAGTGA TTTATTTTTG TTCTGGAATA TGCTTTGGAA      120

AGTAGGGTTT GAAATTAGAA AATTATTTCA CTTTTTGTTT GTTTGTTTGC TTGCTTGTTT      180

TAAGATTGTT CCAGGACACG AAGGGAGATT CTTCCAGGTT ACTGAAAGCA CTTCCTTTGA      240

AGCTTCAGCA AACAGCTTTT GAAAATGCAT ACTTGAAAGC TCAGGAAGGA ATGAGAGAAA      300

TGGTAATTTT AAGTAACATG TATTTGCTGT TATCATATGC TTGCTATGAA TATCCCATAA      360

ATTACTTCAC CAAGTTTGGT ATAAGAGAGT TTATAATCCA GTAGTTTACA GTATAAAGCT      420

GCTCTTCCCC AACTGTATGA ATTGATTGAA ACTGCATTCT TTCTGGGTCA CAATGGGTCA      480

AATCATAGCA ATTTCTTTTG GTTTAGCA                                         508

(2) INFORMATION FOR SEQ ID NO:31:

(i) SEQUENCE CHARACTERISTICS:
        (A) LENGTH: 435 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

AAAATTGGTA TGTAAACAAT TACAATTTAC ATTACAATTT TTTTTTAAAT TTCTTTTTAA       60

GTCCCATAGT GCTGAGAACC CTGAAACTTT GGATGAAATT TATAATAGAA AATCTGTTTT      120

ACTGACGTTG ATAGCTGTGG TTTTATCCTG TAGCCCTATC TGCGAAAAAC AGGCTTTGTT      180

TGCCCTGTGT AAATCTGTGA AAGAGAATGG ATTAGAACCT CACCTTGTGA AAAAGGTATA      240

TATGGATGAG TATTTTATTA GAAGCTTCCT TAGGTCACTG TGAAATAATT TAAAAAGTTA      300

AAGCTAGATT TTCTGAGTGG CACTTATTTA AGACTAGGAA ACAATTTTAT TTTTTAGGTT      360

GGGAATATTG GAAAGCAGTT ATACAAAAAC TATTCAAATG GTATATTTAT GGTATGCACT      420

GTTTCTTACA TTCCA                                                       435

(2) INFORMATION FOR SEQ ID NO:32:

(i) SEQUENCE CHARACTERISTICS:
        (A) LENGTH: 548 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:32:

```
TGCTATGTGT CAGATACTGT GCCAGTTGAG TACATTTTCT TAATTATTAT TCCCATCTCA      60

TAGATGAGGA AATCAAGAAA AGTTGAATGA ATGTTGTTTC TAGGTCCTAC TCTAAATAAT     120

ATTAACAAGC ATTAAATGA TTTATTTTTT TCATTTTTCT TAACACATTG ACTTTTTGGT     180

TCGTGCAGGT TTTAGAGAAA GTTTCTGAAA CTTTTGGATA TAGACGTTTA GAAGACTTTA    240

TGGCATCTCA TTTAGATTAT CTGGTTTTGG AATGGCTAAA TCTTCAAGAT ACTGAATACA    300

ACTTATCTTC TTTTCCTTTT ATTTTATTAA ACTACACAAA TATTGAGGAT TTCTATAGGT    360

AAGTTTATAC ATGACATATG TGAAATTTGT TTAATTTAAA ATTAGTTAAC AATACTTAGC    420

AAGTCCCCTC ACCAGCAACA CACATACCAT ACCCATACAC ATGTGTGTGT GGGAGCCTAC    480

ATAGTATGAG AAGCAGGACA GCTTCTTTTA ATAAGAATGT ATTGAAGGGA GTCACTGGAC    540

TTCAGATC                                                             548
```

(2) INFORMATION FOR SEQ ID NO:33:

(i) SEQUENCE CHARACTERISTICS:
        (A) LENGTH: 631 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

```
ATTTTTTTAA TGTGACTATT TAGAATTTAC TTAATTTTTC CATTTATAAA ATTAAAGAAT     60

GTTTAATAAT CTGGATAAAG TATGATACTT TAATGCTGAT GGTATTAAAA CAGTTTTTAA    120

GAACTATTTT ATAAAATTTT ACTTGGAAAA GTTATATATA ACCTGTATTT TAAATTTTTC    180

TATTTTTAGA TCTTGTTATA AGGTTTTGAT TCCACATCTG GTGATTAGAA GTCATTTTGA    240

TGAGGTGAAG TCCATTGCTA ATCAGATTCA AGAGGACTGG AAAAGTCTTC TAACAGACTG    300

CTTTCCAAAG ATTCTTGTAA ATATTCTTCC TTATTTTGCC TATGAGGGTA CCAGAGACAG    360

TGGGATGGCA CAGCAAAGAG AGACTGCTAC CAAGGTCTAT GATATGCTTA AAAGTGAAAA    420

CTTATTGGGA AAACAGGTAT GGCTTCAATT TTTATGTACT TTTCATTCCC TGAATGATAT    480

GAGATATAAC CTTTAAGTTT TAAGGCTATT TATTCGATTT ATTCGTATTT ATATATTGAA    540

ACTTAGCTTG TGGTAATCAT TATCTAGCAT AGCCAACCCA TGAATTTTTT TGGTTATGTC    600

GTGTTGTCTC CCTCTGATTG GCTTTTAACT A                                   631
```

(2) INFORMATION FOR SEQ ID NO:34:

(i) SEQUENCE CHARACTERISTICS:
        (A) LENGTH: 499 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

```
GGGGGCCTTG TTTGGCTGAT TTTCATACTT TTTCCTCTCA GTCTACAGGT TGGCTGCATA     60

GAAGAAAAAG GTAGAGTTAT TTATAATCTT GTAAATCTTG ACTTTGAGT CATCTATTTT    120

CTTTTACAGT CATCGAATAC TTTTGGAAAT AAGGTAAATAT ATGCCTTTTG AGCTGTCTTG    180

ACGTTCACAG ATATAAAATA TTAAATATAT TTTAATTTTG TGCCCTTGCA GATTGATCAC    240
```

```
TTATTCATTA GTAATTTACC AGAGATTGTG GTGGAGTTAT TGATGACGTT ACATGAGCCA      300

GCAAATTCTA GTGCCAGTCA GAGCACTGAC CTCTGTGACT TTTCAGGGTA TGTACATTTT      360

AAACTTAGAG AACTAGCTCT AACTTCACAA GTTTTTAAAG AAGTTTATTG GTTGACACCT      420

TCAATGTCTA TTTCAATTTA TAGACATCAC TCTTTTTAAA AATTTTCTT CAAAAATAGC       480

CACCTTTGAA TTGAGGTAA                                                   499
```

(2) INFORMATION FOR SEQ ID NO:35:

(i) SEQUENCE CHARACTERISTICS:
        (A) LENGTH: 1215 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

```
TAATCTGATT TATATATCTG GACTGTGATA TGTCATTTGT GATTTTATTG AAAGTATAGT       60

TTTTCAGTAG AAAAATGGTT TTTGAATTTG GGGGTTATTA AAATCTAAAT TTTCATTTTG      120

GAAGTTCACT GGCTATGAAC AAAACTTTTT AAAACGATGA CTGTATTTTT TCCCTTAACT      180

CTGTTAGGGA TTTGGATCCT GCTCCTAATC CACCTCATTT TCCATCGCAT GTGATTAAAG      240

CAACATTTGC CTATATCAGC AATTGTCATA AAACCAAGTT AAAAAGCATT TTAGAAATTC      300

TTTCCAAAAG CCCTGTAAGT ATACATGATG AGTTTAATAA TAGAACATTC CTTCTTTTTT      360

AGCTAAAAAA ACTTTGTAAA TACATCTTAA AGAGGAAAAG TAAACAAATG AAAAATTTAT      420

CTCATAATTA AAAAGGAAAA CATTCATTTA CAAGTTTAAA TGGTATTTTA CTTGTCAGCA      480

TTAATTGAAA TATGTTACAT ATGAGAACAG AATCTTGTGA CACTTTAGTG ATATATTAGC      540

TCAGGGAATA TATCTACTTT TTCATAGGAA TATACTATTT AATTGTAGTT TACTTTCTGA      600

AAATTAAATA AATTGGCAAT AGTTTAAGAT AGTAATTTTC TTAATGTAAC ATTTTGTACT      660

TGATATCAAA CCCAAATCTA AATTCTGTTA TTTAGTTATT TTAAATATAA AATGTGTAGG      720

TATTCAAATA TTTGAAGAAA AAATATAAAG TGTATTTATT GTAGCCGAGT ATCTAATTAA      780

ACAAGTTTTT ACTAAATCTG TTTATTTTCT TAGGATTCCT ATCAGAAAAT TCTTCTTGCC      840

ATATGTGAGC AAGCAGCTGA AACAAATAAT GTTTATAAGA AGCACAGAAT TCTTAAAATA      900

TATCACCTGT TTGTTAGTTT ATTACTGAAA GATATAAAAA GTGGCTTAGG AGGAGCTTGG      960

GCCTTTGTTC TTCGAGACGT TATTTATACT TTGATTCACT ATATCAACCA AAGGTAAATA     1020

ACATATTTAG ACCAATATAT AAGCAGTCTT TCTATCCTGT TCTTCCTGTT TTTTTGCTTT     1080

GTTTTGTTTT GTTTTGAGAC AAAGACTCAC TCTGTCCGCC CAGGCTGGGT GCAGTCACGG     1140

CTCACTGCAT CCTCAACCTC CTGGGTTCAG ATTATCCTTC CTCCTCACCC TGCCGGGTAG     1200

CTGGGGCTAC AGGAG                                                     1215
```

(2) INFORMATION FOR SEQ ID NO:36:

(i) SEQUENCE CHARACTERISTICS:
        (A) LENGTH: 1235 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

```
ATGTTTCTAT TAAAGGATGG AAGCTTAGAG CTGCCTATTC TGCATTTTGC TGATGTGACT       60
```

```
TCTCTTTTTG GCTTATAAGC CATTAAAATA TTTTGTCAAG GCATATAAGA ATTAGAGATG    120

CTGAACCAAA GGACTTCTGA ATGAATTTAT TTCAGAGTAA TTTTCCAGAA CTTACTGGTT    180

GTTGTTGTTT TTTTTTCTCC CTATATTAGG CCTTCTTGTA TCATGGATGT GTCATTACGT    240

AGCTTCTCCC TTTGTTGTGA CTTATTAAGT CAGGTTTGCC AGACAGCCGT GACTTACTGT    300

AAGGATGCTC TAGAAAACCA TCTTCATGTT ATTGTTGGTA CACTTATACC CCTTGTGTAT    360

GAGCAGGTGG AGGTTCAGAA ACAGGTAATT TTCTGACTCA TCTTCAAAAA TGGTATTTAA    420

AATATATAAA GTATTGTTAG AAGGATTTGA GTGTTTTATG TTTATTTGGT ATAATTGGTG    480

ATTTTATTGA GAATATTTTT TGTAAAATGA TTGGAAAAAT ATTCTTAATG AATTAACCTT    540

TGTAATCAAT TACAGAGCAC TTGGTACTTT TGATAGTTTT ATCTACTGTG CTGAAGTGGA    600

GAGGTAGTCA AAACTAGGGA TAGCAGTTCG CAACGTTATG GTGGTATTTG AGTTACTACT    660

TATATAAACT GTTTCATTAA TATTGGCATT TTTTTTAACC TCAGTACCCA TCTTGTAGTA    720

GTACCTTACA TAGTTATTGA ATTATTTGAA AACACAGAAA CTAAAAGCTG GTATCTTAG     780

ACGTAATAAG AACATTTAAT CTGATCTAGG TTAATAGATT TTATCATTTA TTACAGTAAG    840

TTTTGTTGGC TTACTTTAAA ATTATTTCTC TCCTTATAAT TTTTTCTTTT TAAATTATAT    900

TTAGGTATTG GACTTGTTGA ATACTTAGT GATAGATAAC AAGGATAATG AAAACCTCTA     960

TATCACGATT AAGCTTTTAG ATCCTTTTCC TGACCATGTT GTTTTTAAGG ATTTGCGTAT   1020

TACTCAGCAA AAAATCAAAT ACAGTAGAGG ACCCTTTTCA CTCTTGGAGG TAATAAAAAT   1080

TTCATCATCT ACTATTTTTT ATTAGAGAAC ATAGTAGTAC TTTTCAAAAA TCTGTAATGC   1140

TCTAGCAGTA AAAAATGGAA TCTTTTCTTT AATTGTGATT AAAAATATAT ACGTAGGCCA   1200

GGCACATTGG CTCATGCCTA TAATCTCAGC ACTTT                              1235

(2) INFORMATION FOR SEQ ID NO:37:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

GACTCTGTCT AAAAAAGAGT ATTAAAACAT TGTAGGGTTT GCAGTGGAAG AAATCATTTA     60

TTTCTTCCTT GATTAGTAGT AATAGAGACA TGAGTCAGTG TCTATAAATG GCACTTAACT    120

AATTTTTTTC TTTTATTAAG TTTTATTTCA CAGGCTTAAC CAATACGTGT TAAAAGCAAG    180

TTACATTTTC TCTTTTAGGA AATTAACCAT TTTCTCTCAG TAAGTGTTTA TGATGCACTT    240

CCATTGACAA GACTTGAAGG ACTAAAGGAT CTTCGAAGAC AACTGGAACT ACATAAAGAT    300

CAGATGGTGG ACATTATGAG AGCTTCTCAG GGTGCTAATT TTAAATGACA TGGGCTATTT    360

CTACCTGTTT CTTTTTGGAA AGAATATTTT GCAAAGTCTT GCTCTTGGTT TCATTGTCAC    420

AGACTTAGTT CAGACTCTCA TCATTTAGTT CAGACCCTCA TTTCTCATCT AACTGTAAAA    480

CTGGTCCTAA CTGGTCTTCT CACCCTGAAC TCTTCCTGTT TTATTCATCC TCTGCCAGAT    540

G                                                                    541

(2) INFORMATION FOR SEQ ID NO:38:

(i) SEQUENCE CHARACTERISTICS:
        (A) LENGTH: 537 base pairs
```

(B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:38:

ACCTCTGTCT CCCAAAGTGC TGGGATTACA GTCGTGAGCC ACCGCACTCG GCCTTAAGGT      60

TAATTCTTGA AGTACAGAAA AACAGCATTA TAGTTTGGAA ATTAGAAAAT ATCAGTTTTA     120

TGTATGATCT CTTACCTATG ACTCTACTGA AATAGAATTT CTATATGTAG AGGCTGTTGG     180

AAGCTGCTTG GGAGAAGTGG GTCCTATAGA TTTCTCTACC ATAGCTATAC AACATAGTAA     240

AGATGCATCT TATACCAAGG CCCTTAAGTT ATTTGAAGAT AAAGAACTTC AGTGGACCTT     300

CATAATGCTG ACCTACCTGA ATAACACACT GGTAGAAGAT TGGTGAGTAT TTATTGATAC     360

CTTATATGTA ATCTCAATAT GACATTCATG GAGAATGATA CTTCACACAA ATAGATATTC     420

TCAGTAACTA AAGCTTTGTC CTTTTTTAAA TCTCAGTGTC TTTATGAAAA TTCTTATATT     480

TTTATTAATT CACATAATTA TTTACCCTAC TATGTGCCAG ACACTTGATA TAATGGT       537

(2) INFORMATION FOR SEQ ID NO:39:

(i) SEQUENCE CHARACTERISTICS:
            (A) LENGTH: 531 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:39:

GTTGCAGTGA TTAGTAATTC AAGTTTACTG AATGACTAGT GAAAGTCCTT TGATACTTTT      60

ATTTGATATT GGAGAATTTT GTAAATGTAA AGTTTCCTAA AACCAATTTT AAATTTTAGT     120

TTTGAAATTT TTTCAGTGGA GGTTAACATT CATCAAGATT AATAACTGGT GTACTTGATA     180

GGCATTTGAA TTGTTTTTTT CAGTGTCAAA GTTCGATCAG CAGCTGTTAC CTGTTTGAAA     240

AACATTTTAG CCACAAAGAC TGGACATAGT TTCTGGGAGA TTTATAAGAT GACAACAGAT     300

CCAATGCTGG CCTATCTACA GCCTTTTAGA ACATCAAGAA AAAAGGTCTC TTAAGTAATA     360

AATGTTTATT GAATACCCAG CATATCTAAA ACAGTTCTGT TTGCTGTGGG TCATGACTGT     420

TAAATTGCTT GAAATAGTAT TGTACTAACT ATTAACCTTT CCTATAAGTA ATTTAAGCCA     480

TATTTCATAA ATCCAGGGAA TGTGTTATTT TTAATTTATT ATGGCAGTGT G             531

(2) INFORMATION FOR SEQ ID NO:40:

(i) SEQUENCE CHARACTERISTICS:
            (A) LENGTH: 527 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:40:

AAACATAAAT GTTTTCATCT TAAAAGGTAA ACATTGCCTC CAGATTTAGT TTTAACTGTA      60

TTTAGCTTTA TTCAGAAAGA TTTGTTATAC TCATTTGTG TAGGAAAGGT ACAATGATTT     120

CCACTTCTCT TATTTACATT TTCTAATCCC TTTCTTTCTA GTTTTTAGAA GTACCCAGAT     180

TTGACAAAGA AAACCCTTTT GAAGGCCTGG ATGATATAAA TCTGTGGATT CCTCTAAGTG     240

AAAATCATGA CATTTGGATA AAGACACTGA CTTGTGCTTT TTTGGACAGT GGAGGCACAA     300

```
AATGTGAAAT TCTTCAATTA TTAAAGCCAA TGTGTGAAGT AAGAAGATTA ATTAGTCTGA      360

TATAATTCCT TGTTTATGAC CTGTTTATCT AAAGAGTGCT GTGATACTGC ACATCATCTT      420

CACATAATAT CACCCCCACT CAAACTGTTG TAAATTTATT AAAGTGAGCA TCCGTATTTA      480

GTCATAACTT TATGCATTAG GTTTCAGCTT CGGGATAGCA ACATACT                    527

(2) INFORMATION FOR SEQ ID NO:41:

(i) SEQUENCE CHARACTERISTICS:
        (A) LENGTH: 567 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

CCTAGTGTGG TTTTTTAAAC ACCACCTAAT ACATGTTTTT TGTTTGTTTT TTTAGCAGTA       60

TGTTGAGTTT ATGGCAGATT AATCTATCAT CTTTTAGAAA TTTAATATGT CAACGGGGCA      120

TGAAAATTTT AAGTAAAATG TATTAATTTT ACTCATTTTT ACTCAAACTA TTGGGTGGAT      180

TTGTTTGTAT ATTCTAGGTG AAAACTGACT TTTGTCAGAC TGTACTTCCA TACTTGATTC      240

ATGATATTTT ACTCCAAGAT ACAAATGAAT CATGGAGAAA TCTGCTTTCT ACACATGTTC      300

AGGGATTTTT CACCAGCTGT CTTCGACACT TCTCGCAAAC GAGCCGATCC ACAACCCCTG      360

CAAACTTGGA TTCAGGTATT CTATTAAATT TTTAACATTA ATACTGTAAA CTCAGTTCTA      420

GAGAAAGATG GATTTAAGAT GGAATCCCAC TAAAAGCACT TTACAGGATT AAATCTATAA      480

CCTCTAAATT TGTTTCTTCA TCTATGGAAT GGAGATAAAA GTTGCCAACA GTTGCAACAA      540

GTTTTCAATG AAATAATGTG TGTAAAG                                         567

(2) INFORMATION FOR SEQ ID NO:42:

(i) SEQUENCE CHARACTERISTICS:
        (A) LENGTH: 475 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

TAAGTTCTCA CTTTTTTTAA GATAACAGTT TCTTTTAAAA GCAAAGAAA TCCTATTAAA        60

TTCCTTCAGA ACCAATTTTG TGTTAGGTAC TGCCCACCAG AACCTTATAG CATAGTGGGA     120

GACAGACACA TAAACAAGAA GGAAGAAGGT GTGTAAGCAA GAATGCCTGG GACTGAGGGG     180

AGATATTTTT GTTTGTCAGA GTCAGAGCAC TTTTTCCGAT GCTGTTTGGA TAAAAAATCA     240

CAAAGAACAA TGCTTGCTGT TGTGGACTAC ATGAGAAGAC AAAAGAGGTA ATGTAATGAG     300

TGTTGCTTCT TACGTTTAGG ATCTAGAGTG TAACTTGTTA ACTATCGGCT GAATTTTAAC     360

ATGATTATTT TAGGTGAAGG TGTTGCAAAG TGTTATATTT AATTTGTGTG ATATTTATAT     420

CTCCTTGCAG TAATCCATAT TCAGGATAGC AGTTTGGTTA AATCAGTGTC AAGAA          475

(2) INFORMATION FOR SEQ ID NO:43:

(i) SEQUENCE CHARACTERISTICS:
        (A) LENGTH: 528 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:43:

| TTAATTAAAT | AGGACTCTTC | AGCCATGTTA | TCTTATAATG | TTTATAGGTA | TATATTGGGG | 60 |
| AAATGTGGTT | TTTGGGAATT | TGTAATTTTC | TGTTAAGCAG | TCACTACCAT | TGTATTCTAT | 120 |
| ATCAACATGC | TTTTATTTTG | ATATTGAAGT | TTAAAAAAGT | GAATGACATT | ATATCTCATT | 180 |
| TTTCTTTAGA | CCTTCTTCAG | GAACAATTTT | TAATGATGCT | TTCTGGCTGG | ATTTAAATTA | 240 |
| TCTAGAAGTT | GCCAAGGTAG | CTCAGTCTTG | TGCTGCTCAC | TTTACAGCTT | TACTCTATGC | 300 |
| AGAAATCTAT | GCAGATAAGA | AAAGTATGGA | TGATCAAGAG | AAAAGGTAAT | GGAATTTAGA | 360 |
| ATTTTTGGTT | TTTAAAATTA | ATGTTGGCAT | TGTCTCAATA | AGGGTATATA | GTAAAGATTT | 420 |
| ATTTTGCCTC | CTGTTCCCCA | TTTAAAAGAT | ATTTTAGATA | GAAATTTTGT | TTTAAAGTGA | 480 |
| AATTATAATA | AATTTTTAAA | AAGGAATATG | TAATTCCTGT | TCTGAAAT   |            | 528 |

(2) INFORMATION FOR SEQ ID NO:44:

(i) SEQUENCE CHARACTERISTICS:
            (A) LENGTH: 444 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:44:

| CTTTTCCATC | CTAGGTATAA | ATGGTATTAT | GTTTTAAAGT | ATAAGTGATT | TATTCTGTTT | 60 |
| TGTTTGCCAC | CTTCATTAGT | TTTTTTCTGT | CAAAGTCTAT | AGTATATGTA | TTCAGGAGCT | 120 |
| TCCAAATAGT | ATGTTCTCAT | TAAAAGAGGT | GTTCTTGTGA | CAAACAGAAG | TCTTGCATTT | 180 |
| GAAGAAGGAA | GCCAGAGTAC | AACTATTTCT | AGCTTGAGTG | AAAAAAGTAA | AGAAGAAACT | 240 |
| GGAATAAGTT | TACAGGTAAA | TATTAGAGGC | TCTATTATTT | ATGACAGTAT | TTATCTCATA | 300 |
| CTTTGGGTTA | TTTTGTTATA | GACACTGTAC | AGATGCCATG | TGATTTTTAA | ACTGAATTTA | 360 |
| CTTACTGGAC | TAAGCATCAT | ATATATAAAA | TTATGGTCTG | AAGCTTAAGC | CTTAGAGTAG | 420 |
| ACAGACTTGA | GTTCTAATAC | TGAC       |            |            |            | 444 |

(2) INFORMATION FOR SEQ ID NO:45:

(i) SEQUENCE CHARACTERISTICS:
            (A) LENGTH: 688 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:45:

| TTGTCCTGCA | CAGTTCAAAC | TCGTGTTGTT | TGAACTGTAT | TTCAGAACTG | TATTTCAGAA | 60 |
| TCATTACATT | TTATTTCTAT | AACATAACAT | TTAGAGTTGG | GAGTTACATA | TTGGTAATGA | 120 |
| TACAATTTAA | AATTTGCTAA | ATTTATAGAC | CGATTTTTTT | TCCTTCTTCA | ATTTTTGTTG | 180 |
| TTTCCATGTT | TTCAGGATCT | TCTCTTAGAA | ATCTACAGAA | GTATAGGGGA | GCCAGATAGT | 240 |
| TTGTATGGCT | GTGGTGGAGG | GAAGATGTTA | CAACCCATTA | CTAGGTAAAT | TGCATTTTTC | 300 |
| TAAACAACGG | TATAGTAATT | CTGTTTATGA | AGGAGTTATG | TGTGTGTTAA | ACCCAAAGCT | 360 |
| ATTTTCACAA | TCTTTTCTTA | TAGACTACGA | ACATATGAAC | ACGAAGCAAT | GTGGGGCAAA | 420 |

```
GCCCTAGTAA CATATGACCT CGAAACAGCA ATCCCCTCAT CAACACGCCA GGCAGGAATC        480

ATTCAGGTAC ATTTTTTCCC AGATTTGGTA AAGCCATCAC TAGTGTAGTG CTGAGGTTAT        540

TTCAGTATGT TGGTGGATAT TTACACAGCC AGATAAACTC TAGAGATAAG ACTAGAACTT        600

ATCTGTTTTT CAGAGGATTA GGCTAAACAT TCAGGGATAC TCCTGAAGCA GAGGGATGCA        660

AAAAAAGAG AAAAAATTCA GGGAGACA                                            688

(2) INFORMATION FOR SEQ ID NO:46:

(i) SEQUENCE CHARACTERISTICS:
          (A) LENGTH: 418 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:46:

CCTCCTGCCT CAGCCTCCCA AAGTGCTGAG ATTACAGGCA TGAGCCACCA CACCCAGCTG         60

ATATTTTGGG ATTTTAAATG ATATTGTGAA CTAAAATTTG TCTAAGTTAA TTTGTATCTT        120

TGCTGTTTTT TTCTCTGGTT TTCTGTTGAT ATCTTTGATT ACTTAACTTA AAAACAAAAT        180

AACTCCTGTT TAGGCCTTGC AGAATTTGGG ACTCTGCCAT ATTCTTTCCG TCTATTTAAA        240

AGGATTGGAT TATGAAAATA AAGACTGGTG TCCTGAACTA GAAGAACTTC ATTACCAAGC        300

AGCATGGAGG AATATGCAGT GGGACCATTG CACTTCCGTC AGGTAAGAAA TTTGACTTGA        360

TTTTTTTTTT TTTGCCTCTC TCCTCATTCT AAACAACAAC TGTTTTTCTC TTCTATGA         418

(2) INFORMATION FOR SEQ ID NO:47:

(i) SEQUENCE CHARACTERISTICS:
          (A) LENGTH: 513 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:47:

TTTTTCTGCT TAAAGAATTT AAATGACTCA TAAAATTTGT ATTTCTTACC AAAAATTCTA         60

GAAATGCATT TTTTAGAATG GAGAAATGTT AATTTAAAAA TTTTGTCCTT TGGTGAAGCT        120

ATTTATACAT GTATATCTTA GGGTTCTGTT TTTAAGTATA TTTTTTTCTT TGACTTATCT        180

CACAGCAAAG AAGTAGAAGG AACCAGTTAC CATGAATCAT TGTACAATGC TCTACAATCT        240

CTAAGAGACA GAGAATTCTC TACATTTTAT GAAAGTCTCA AATATGCCAG GTATTATGAA        300

AAGACAAAGT TACTGTATTT TAACATTTAA TGTCATGGCT TCTTTTCTGA AAACTTGAGA        360

AACAATTTTA ATGTAAGGAT TTGCATTGAT GAAGAGATAA AGACTTGGTG GCTGTGATCA        420

GATGTTTCCT TGTAATTCTC TGCCCTCCTT CAAAACAAAT TGTTTCTGGG ATTCCAGGTT        480

CATTCTTTAC CCTGACCCTT CAAGAAAGTT TTG                                     513

(2) INFORMATION FOR SEQ ID NO:48:

(i) SEQUENCE CHARACTERISTICS:
          (A) LENGTH: 513 base pairs
          (B) TYPE: nucleic acid
          (C) STRANDEDNESS: single
          (D) TOPOLOGY: linear (ii) MOLECULE TYPE: DNA (genomic)
```

(xi) SEQUENCE DESCRIPTION: SEQ ID NO:48:

```
AGTGTAAGTG GACCATGCAT TTAAATTTGT GTTGTTCAAG GGTCAGTTGT ATTCTGTTTC      60
CACTGCTATT TTGTACTCAC TGCTGCTTGT TAGTATTATT AGATCAGTAG CATAGCCTAT     120
GATGAGAACT CTTTAACAAC AAATTTAAAC ATTTATTTCC CTGCAAACCT CTTCTTTATT     180
TTCAGAGTGT CTTTTCTTTT TTGCTACTAG AGTAAAAGAA GTGGAAGAGA TGTGTAAGCG     240
CAGCCTTGAG TCTGTGTATT CGCTCTATCC CACACTTAGC AGGTTGCAGG CCATTGGAGA     300
GCTGGAAAGC ATTGGGGAGC TTTTCTCAAG GTATGTAATT CGTATGACTT TGTTATCCTA     360
AAGTGCAGCT TTTCTGTTAC CAATAGTGAC TTTAAAAAAT AAAAACTATA GGCCGGGCAC     420
GGTGGCTCAT GCCTGTAATC CTAGCACTTT AGAAGGCTGA AGTGGGTGGA TCACTTGAGG     480
TCAGGAGTTC AAGACCAGCC TGGCCAACAT GGT                                  513
```

(2) INFORMATION FOR SEQ ID NO:49:

(i) SEQUENCE CHARACTERISTICS:
        (A) LENGTH: 1254 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

```
TGTATTATTA TAATATTATA TCGTAAGTTC CAGGACTTAC ATAGTTTTTT TTTTTTTTTT      60
TTCATTTCTC TTGCTTACAT GAACTCTATG TCGTGGCATT CAGATCAGTC ACACATAGAC     120
AACTCTCTGA AGTATATATT AAGTGGCAGA AACACTCCCA GCTTCTCAAG GACAGTGATT     180
TTAGTTTTCA GGAGCCTATC ATGGCTCTAC GCACAGTCAT TTTGGAGATC CTGATGGAAA     240
AGGAAATGGA CAACTCACAA AGAGAATGTA TTAAGGACAT TCTCACCAAA CACCTTGTAG     300
AACTCTCTAT ACTGGCCAGA ACTTTCAAGA ACACTCAGGT AAATACAATT TAAAACTATG     360
TCATCTTACC TCTTGACTTT CCTTTTATTA TTTAAAAAAC TGAAAGCCTG AGGGAAAAAG     420
AAATGTCATT AAGAGATAGA GATCTCTATT AATATATAGT AAAAATAATT GTTTAAGAGT     480
TCCCATTTTG GAATTAGATC TGACTTTTAA GCCTTGGGCA AGGGTACTTA ATCTTTTCTC     540
AACCTCAATT TCCTGGTTAT AAAATGAGAA GATACCTAAC TTACTATATT GATAACAATT     600
CAGTGATTTT ATATACTGTG TGTATGTACA CACAGATACA CATACATACA TATAGAGAGA     660
GACAGACAGA CAGACAGATA GGCAGACGTG GGGTGGGGAG ATTGTCAATG CAGACAGAGA     720
GGGTCCTTAA AGATAGTCCC TGACAAGTAG TTAAAGTCCT CAAATGAATG GTAGTTGCTG     780
CTTTCATTAT TATTATTATT CAAGGTAGTA GTATCAAGTA GTAAAGTAT TTATTCCCAT     840
ATGTCATTTT CATTTCAGCT CCCTGAAAGG GCAATATTTC AAATTAAACA GTACAATTCA     900
GTTAGCTGTG GAGTCTCTGA GTGGCAGCTG GAAGAAGCAC AAGTATTCTG GGCAAAAAAG     960
GAGCAGAGTC TTGCCCTGAG TATTCTCAAG CAAATGATCA AGAAGTTGGA TGCCAGCTGT    1020
GCAGCGGTTT GTTTTTTTTA TTGGCTGGAT TAGTGTTTTA CTGTTATTTA AAAAAACACA    1080
AATGTACTTT AAAATATTTT TAATAACAAT TTTATTAGAG CCTTGAAATT AGTAATTTAT    1140
TAACAAGATA TTGTAAAACT AGTCTTGAAA ATTAATTTGT AAATGAAGTT TAGAAACTTT    1200
TTCCTATATA TCACAATTCT ATCAGTCCAT CATGTGGTCG ATTCATTTAA TATA          1254
```

(2) INFORMATION FOR SEQ ID NO:50:

(i) SEQUENCE CHARACTERISTICS:

(A) LENGTH: 537 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

TAATAATAAT AAACAGAGGA TGATCATTTC CTACATGGGA TTATTAAAAT AGTTGTATGG    60

CAAAAGCAGA TGAGGAAAAA CTTTTTTTTT CCCACCCACC AAGGAAAAAC ATTTTTAACC   120

TGCTTTTTTC CCCCGTACAT GAAGGGCAGT TGGGTACAGT CATGGTAATG CATTATATTT   180

TAAGATTTTG CCTTTCTTAT ACAGAACAAT CCCAGCCTAA AACTTACATA CACAGAATGT   240

CTGAGGGTTT GTGGCAACTG GTTAGCAGAA ACGTGCTTAG AAAATCCTGC GGTCATCATG   300

CAGACCTATC TAGAAAAGGT AAGATTTTTG GAGCAACCCT TAAGATAGTT ACTTAGCATG   360

AATATGCTTC ATCTTTTCAT CAAGATCAAT ATATTTCCAA AGCAAATAAA AGTATGGTTT   420

TATTTTTCTA TATATTATTA CTGTTGTAGC TCTGTATAGT CTCTAGGGTG GAGTGAAACA   480

TTGTTACAAA ACAAAGCAGC CAATTTGAAA AGTAAGCCCA AGTATAGTAT CTCTTCT     537

(2) INFORMATION FOR SEQ ID NO:51:

(i) SEQUENCE CHARACTERISTICS:
        (A) LENGTH: 679 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

TTTAAGAAAA TGTACGAATT TGTGTTGGGC CACATTCAAA GCCGTCCTGG GCCACATGCG    60

GCCCATGGGC CGTGGGTTGG ACAAGTTTGC AATAGTTCAT ATAATTTAGC TAGCTTTTAT   120

ATGTATATAA GTTAAATTTT AGTGTATTAC CTTAATTTGA GTGATTCTTT AGATGTATTT   180

AGTATTTGTA AATATAATTT AAATTGGTTG TGTTTTCTTG AAGGCAGTAG AAGTTGCTGG   240

AAATTATGAT GGAGAAAGTA GTGATGAGCT AAGAAATGGA AAAATGAAGG CATTTCTCTC   300

ATTAGCCCGG TTTTCAGATA CTCAATACCA AAGAATTGAA AACTACATGA AATCATCGGA   360

ATTTGAAAAC AAGCAAGCTC TCCTGAAAAG AGCCAAAGAG GAAGTAGGTC TCCTTAGGGA   420

ACATAAAATT CAGACAAACA GGTAACTAGG TTTCTACAAG TGACAATTTT ATGTTCACCA   480

GTTAACTGAG TGAGTGTTTT TGCATAGAAA GAGTGACTTG GTCTTTTTAT CTGATATAGT   540

TTTGAGCTCT AAAGGTCGGC TTAACTATAT ATAGATTATC TTGGTCTTTT GGGTTCTTTT   600

CGGTTTTTGT TTTTTGTGTT TTTTTTTGAG ACAAGGTCTC ACTCTGTCAC CCAGGCTGGA   660

GTACAGTGGC GTGATCACT                                               679

(2) INFORMATION FOR SEQ ID NO:52:

(i) SEQUENCE CHARACTERISTICS:
        (A) LENGTH: 610 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

TCCCCTTTGT CCTTTGATGC TTAGGAAGGT GTGTGAATTG CACAGTTAAG ACAAAAGTAA    60

| | |
|---|---|
| GTTTATTCCC TTTATAATCC TTAGAAGTTT GCTTTTTTCC CTGGGATAAA AACCCAACTT | 120 |
| TTTTCATTAA ATGTTGTATA TCATGTGTGA TTTTGTAGTT CTGTTAAAGT TCATGGCTTT | 180 |
| TGTGTTTTAC CTTAATTATT CTATGCAAGA TACACAGTAA AGGTTCAGCG AGAGCTGGAG | 240 |
| TTGGATGAAT TAGCCCTGCG TGCACTGAAA GAGGATCGTA AACGCTTCTT ATGTAAAGCA | 300 |
| GTTGAAAATT ATATCAACTG CTTATTAAGT GGAGAAGAAC ATGATATGTG GGTATTCCGG | 360 |
| CTTTGTTCCC TCTGGCTTGA AAATTCTGGA GTTTCTGAAG TCAATGGCAT GATGAAGGCA | 420 |
| AGTGTTACTC AGCCCAATAT TCTACCCTGT GCTTGAAAAA CTTAGACATA AGCCCCTTGA | 480 |
| TGTCAGGAAT CGTGTATACC TCTTTGTATT CCTAGCACTT GGTCCAGTGC TCTACACATA | 540 |
| AGTAGCATTT TGTAGTTTTC TAAACTTTGA TCCATATTTA GGATTATTTA CAAGTTCTAG | 600 |
| TCTTGTTTCT | 610 |

(2) INFORMATION FOR SEQ ID NO:53:

(i) SEQUENCE CHARACTERISTICS:
        (A) LENGTH: 988 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

| | |
|---|---|
| AATCCAGTTT AATTTAGGAC CCAATATTTT GATTTACCAA TGCATTAATC TAGAGTACCC | 60 |
| ATTAGAAAGA CCTTCAGATA AGAAAAGAAA TGAAGGAAAA CAATATAGTT AGTGAAGTTT | 120 |
| TGTTAACCAC TTGTGCTAAT AGAGGAGCAC TGTCTTAAAA TAACTTACTT GCTTAGATGT | 180 |
| GAGAATATTT GAAATACCTT GTTTCTTAAT TTTGTGTCTT TTTTTTAATG GTAGAGAGAC | 240 |
| GGAATGAAGA TTCCAACATA TAAATTTTTG CCTCTTATGT ACCAATTGGC TGCTAGAATG | 300 |
| GGGACCAAGA TGATGGGAGG CCTAGGATTT CATGAAGTCC TCAATAATGT AAGTAAACCT | 360 |
| GAAAATCAAA CCACAATAAT TATTTTTATT CTATTATTAC TATATATTAT ATAAAGTATA | 420 |
| TATACCATTC CCTCTAAGAA ATGGAAATAC AAAATTTTGT ATTTTTTGTC TTCTCACATC | 480 |
| ACATAAGTTA CTCATTTTCT CTCTCTAATT CCTCATAGGC CTCTGCCTTT TTCTCACACA | 540 |
| TGCAGGCATA CACGCTCTAC CCACTGCAGT ATCTAGACAG TAATACACAT TTTAATGTTA | 600 |
| AGCAAAATGA AAAATATGGA TTATATTTTT TTGTTTATTT GCATAAATCT AATAGTTCTT | 660 |
| TTCTTACAGC TAATCTCTAG AATTTCAATG GATCACCCCC ATCACACTTT GTTTATTATA | 720 |
| CTGGCCTTAG CAAATGCAAA CAGAGATGAA TTTCTGACTA AACCAGAGGT AGCCAGAAGA | 780 |
| AGCAGAATAA CTAAAAATGT GCCTAAACAA AGCTCTCAGC TTGATGAGGT ATTGGGATTA | 840 |
| ACCATACGTA CCTTTTAGAA GTGTGATATT CAGTCTTTCC TAGAATATTT CTTTTTAAAA | 900 |
| TCTTGTGTTA TTAAGATGCC ATCTAAAATC GGTTCAAGGC TGGCACGGTG GCTCACGCCT | 960 |
| GTAATCCCAG CACTTTGGGA GGCTGAGG | 988 |

(2) INFORMATION FOR SEQ ID NO:54:

(i) SEQUENCE CHARACTERISTICS:
        (A) LENGTH: 537 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

```
GAAAGGCACC TAAGTCATTG ACGAGAGTAT GTATCTTTGA TGTATTTCAT TTATGACTGT      60

TTTGTTTGTA TCTGAGGAAT TATAATCATT CCATAGTCTA GATTTGTGCA TAAATTCTGT     120

TTTTCTCTTT GTTTTTCTAA CTCTGAGAAG TTTAAATGTT GGGTAGTTCC TTATGTAATG     180

TTTTTTGTTT TTTATTAATA GGATCGAACA GAGGCTGCAA ATAGAATAAT ATGTACTATC     240

AGAAGTAGGA GACCTCAGAT GGTCAGAAGT GTTGAGGCAC TTTGTGATGC TTATATTATA     300

TTAGCAAACT TAGATGCCAC TCAGTGGAAG ACTCAGAGAA GTATGTTTTT TTTAAAGAAG     360

AAACGTTACT TTCTTGCTGT GTTACTCTCT GTAGAGATAT ATTAGTTATA GAGCCTAATA     420

AGTAAATCTG CTTAAAATCA CAAACGTAAT CCAAAAGCTT AATTTATATC TGATGGCTTC     480

AACATTCCCT GGTTACTTTT TCACTTAATA TCTCTTAATA GAACTGGTAA TAGGTGA       537

(2) INFORMATION FOR SEQ ID NO:55:

(i) SEQUENCE CHARACTERISTICS:
         (A) LENGTH: 421 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:55:

CTGTTGAGCT TTGACTCTGA GCTGCATAGT GGCCAAAGCC CAGAGTCTTC ATTTCTCAAT      60

CAGAGCCTGA ACCACAGATT AGCAACAAGT TGGGGCCAGT GGTATCTGCT GACTATTCCT     120

GCTTGACCTT CAATGCTGTT CCTCAGTTTG TCACTAAAAT CTCTTCATTT TTAAATACAG     180

AAGGCATAAA TATTCCAGCA GACCAGCCAA TTACTAAACT TAAGAATTTA GAAGATGTTG     240

TTGTCCCTAC TATGGAAATT AAGGTAATTT GCAATTAACT CTTGATTTTT TTTAAACTAA     300

ATTTTTTTTA TTAGATTGAA CCATTTGAAA TAGTATTTTT ATGTAGGTCA AAATTGGTTA     360

AATATTGGCA AATTTCATAT GTTTCAACCT ATAATTTCTC AGTATTATAT TTCCTTTGCC     420

C                                                                   421

(2) INFORMATION FOR SEQ ID NO:56:

(i) SEQUENCE CHARACTERISTICS:
         (A) LENGTH: 449 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:56:

ATATTAGTGA ATCTTTGATG AAACAGTAGT TAAAGTTACG AGCGTGAGCC ACCACACCCG      60

GCCTAAAGTT GTAGTTCTTA ACCACTATCA CATCGTCATT TGTTTCTCTG TTTAATATTA     120

AAATTGCCAT TTATAATGTA TTGTGCTTTA AGTGCAAATA GTGTATCCGA CCTATTAGCA     180

ATCATGTTTA TACTTTTATT AGGTGGACCA CACAGGAGAA TATGGAAATC TGGTGACTAT     240

ACAGTCATTT AAAGCAGAAT TTCGCTTAGC AGGAGGTGTA AATTTACCAA AATAATAGA     300

TTGTGTAGGT TCCGATGGCA AGGAGAGGAG ACAGCTTGTT AAGGTGAGCC TTCCCTTCTC     360

TGGCTTAGCC CTTAGAGTTT TAGTGATGAA AATTTTTAGT TCATATTTCT TTCTGCTTTA     420

TTGGGGATTT GGGTCTTTAT TTGGGAATA                                     449

(2) INFORMATION FOR SEQ ID NO:57:
```

(i) SEQUENCE CHARACTERISTICS:
            (A) LENGTH: 520 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:57:

| | | |
|---|---|---|
| GGGAAACTTT CTAAATCAGT GTAAATGTTG TAGCTTATTC TAAATGAAAG AATGGCAGTA | 60 |
| GGTATTTAAT TATTTGGGAG ACTGTCAAGA GGTGCACAGA TGCTCAGATT GGTTTGAGTG | 120 |
| CCCTTTGCTA TTCTCAGATG ACTCTGTGTT TTTATAATAA AATAAACTGT ACTTGTTTAT | 180 |
| TCATGCTTAA TTATTCTGAA GGGCCGTGAT GACCTGAGAC AAGATGCTGT CATGCAACAG | 240 |
| GTCTTCCAGA TGTGTAATAC ATTACTGCAG AGAAACACGG AAACTAGGAA GAGGAAATTA | 300 |
| ACTATCTGTA CTTATAAGGT AACTATTTGT ACTTCTGTTA GTTCACCAAA AACATATAAA | 360 |
| AGATGCCATT TGGTTGGGTG AAGTGGCTCA TGCCCATATT CATAATGCTT TGGGAGGCCA | 420 |
| AGGTGGGAGG ATTGCTTGAG GCCAGGAGTT CGAGACCAGC CTCAGCAACA TAGTGAGACC | 480 |
| CCATCTTGAC AAAAAGTTAA AAAAAAAAAA AAAACCAGAG | 520 |

(2) INFORMATION FOR SEQ ID NO:58:

(i) SEQUENCE CHARACTERISTICS:
            (A) LENGTH: 519 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:58:

| | |
|---|---|
| TTCTTTGAGC TTAAGTTTAT TTCCGATTGG TTTCCTCCAA GGAGCTTTGT CTTCTATGGA | 60 |
| CAGAGAAATA TTAATACAAC TTGAAAAAAA ATGCTTTGCA CTGACTCTGA TAGCTGAATG | 120 |
| ATCATCAAAT GCTCTTTAAT GGCCTTTTAA AAGTAAAAGG TATTTAATCT GTAACTCCAG | 180 |
| GTGGTTCCCC TCTCTCAGCG AAGTGGTGTT CTTGAATGGT GCACAGGAAC TGTCCCCATT | 240 |
| GGTGAATTTC TTGTTAACAA TGAAGATGGT GCTCATAAAA GATACAGGCC AAATGATTTC | 300 |
| AGTGCCTTTC AGTGCCAAAA GAAAATGATG GTGAGTGACA CCCAAAATTA AAGGTTATTG | 360 |
| TAAGATTATT TAATGGCTTA TTAAAGCTGA CAGCTGTCAG ATATTATAGA ATACAAAAAA | 420 |
| ACTTTAATTT CATCAGGTAA TTGTCAAAGA TACTAAGTAA AAGAAAAACT CATCAGAATG | 480 |
| AAAGTGTGTG AGTGAAAAAG GAAGGATTTT AAACTACAT | 519 |

(2) INFORMATION FOR SEQ ID NO:59:

(i) SEQUENCE CHARACTERISTICS:
            (A) LENGTH: 550 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:59:

| | |
|---|---|
| ATCACTTGTA ATTAATTGCT TCCCTGTCCA GACTGTTAGC TTCTTGTAGG TAATGTATCC | 60 |
| TGTTCATCTT TATTGCCCCT ATATCTGTCA TATTTTTATA TAAAAATGTG TATATTAGTT | 120 |
| TAATTGAACA CAATATTGAA AAATAATTAT ATATATTCTC TATTTAAAGG AGGTGCAAAA | 180 |

-continued

```
AAAGTCTTTT GAAGAGAAAT ATGAAGTCTT CATGGATGTT TGCCAAAATT TTCAACCAGT      240

TTTCCGTTAC TTCTGCATGG AAAAATTCTT GGATCCAGCT ATTTGGTTTG AGAAGCGATT      300

GGCTTATACG CGCAGTGTAG CTACTTCTTC TATTGGTAAT CTTCTTGTAC ATATAGTAGA      360

TTGAGCACTT TGTTGTTTGG CAGGTTTTAT TTTTGTTTGA TTCAGCACTT TTTCTACATT      420

CTGAGTTGCA GGGGGATGAT AGTGATGATG TGGTTAGTAA CCATCCCATC TTCATTATTA      480

AATCATATGT TTCTTGTTCA TCCTGATTCT TAGTGTCTAC CTTTTTATAA CTTATGCAGA      540

AGAGAATTCT                                                             550
```

(2) INFORMATION FOR SEQ ID NO:60:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

```
AATCATCTAG GATTTGTAAA ATGCAATATG CATTAAAATA GCTGGCAAGA TTTGAGTTAA       60

ACTCAACATG GCCGGTTATG CACATCATTT AAGTAGGCTA AAAATCCTAA ACTACTTAAA      120

GATTATACCA AGTCAGTGGT CTTAATTGAA ATTATGGCTA TATATTAGAA AGAGATGGAA      180

TCAGTGATTT CAGATTGTTT GTTTCTTTTT TCTCCAGTTG GTTACATACT TGGACTTGGT      240

GATAGACATG TACAGAATAT CTTGATAAAT GAGCAGTCAG CAGAACTTGT ACATATAGAT      300

CTAGGTAAGT AATAAAATCT ATGTATCTAT TCTTTTTAGT AAATATTTGG TCATCATGGA      360

ATGTTGTTTG CCTACCAAGA TATTACAAAT ATAAGAGACA GATAAATCGA AGCAGTAAAT      420

ATTGGGTTTT TTTGTTTTCA GCATAAACAG TTGTCCTAGA AGAAACAGTT AACT            474
```

(2) INFORMATION FOR SEQ ID NO:61:

(i) SEQUENCE CHARACTERISTICS:
        (A) LENGTH: 483 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

```
GATTTGAGGT GGATCTCACA GACAGTGACA AAGATGAGGA AGGCAGCCAG AGCAGAAGTA       60

AACTACTGTA CATACTAGTG TTCATAGAAC GTAGGTAACA TGTGGTTTCT TGCCTTTGTA      120

AAGTTCACAT TCTAACTGGA AAGAAAGTAA ATTAGCTGTC AAACCTCCTA ACTTCACTGT      180

ATTCTTTACT TTAGGTGTTG CTTTTGAACA GGGCAAAATC CTTCCTACTC CTGAGACAGT      240

TCCTTTTAGA CTCACCAGAG ATATTGTGGA TGGCATGGGC ATTACGGGTG TTGAAGGTGT      300

CTTCAGAAGG TAAGTGATAT GAAGTAAAGG AGGGAAATAA TTTTTGATGT CAAAATTACA      360

TGGGCTGGGC ATGGTTCTTT GCACCTGTAA TCCCAGCTAC TCAAGAGGCT GAAGTGGGAG      420

GATTGTTTGA GCCAGGAGT TTGAGTCCAG CCTAGGCAAT ACAGCAAGAC CCTGTATCTA       480

AAA                                                                    483
```

(2) INFORMATION FOR SEQ ID NO:62:

(i) SEQUENCE CHARACTERISTICS:
        (A) LENGTH: 318 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:62:

TTCTTGTAAA TGCCAAGCTT GTGAAATAGT CAAATACATA TTTGTATTCA TTTCAAACGT      60

CTAATGAAAG CCCACTCTGC CAAGTATTAT GCTATTTTGA GATACAGATA TGTAGATTAT     120

TAAGCATAGG CTCAGCATAC TACACATGAG AGTATACAGA TAAAGATATG TTGACAACAT     180

TGGTGTGTAA CAAAATCCGT ATTTATAATG TGTTTGACTC TAGATGCTGT GAGAAAACCA     240

TGGAAGTGAT GAGAAACTCT CAGGAAACTC TGTTAACCAT TGTAGAGGTA AAGTATTTTA     300

TAAGGAAGAC TTTATTTT                                                   318

(2) INFORMATION FOR SEQ ID NO:63:

(i) SEQUENCE CHARACTERISTICS:
            (A) LENGTH: 453 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:63:

AAGAACAGAT GTTCTCTCTG TTTAGGTCCT TCTATATGAT CCACTCTTTG ACTGGACCAT      60

GAATCCTTTG AAAGCTTTGT ATTTACAGCA GAGGCCGGAA GATGAAACTG AGCTTCACCC     120

TACTCTGAAT GCAGATGACC AAGAATGCAA ACGAAATCTC AGGTGAGCAG TATTTTAAGA     180

AGGTCCTGTT GTCAGTATTT CAGATTTTCT TATTCCCAAG GCCTTTAAAC TGGTCACCTG     240

GACTGGAACC TTTGTGTTTT TGTCCTTAGT GATATTGACC AGAGTTTCGA CAAAGTAGCT     300

GAACGTGTCT TAATGAGACT ACAAGAGAAA CTGAAAGGAG TGGAAGAAGG CACTGTGCTC     360

AGTGTTGGTG GACAGGTGAA TTTGCTCATA CAGCAGGCCA TAGACCCCAA AAATCTCAGC     420

CGACTTTTCC CAGGATGGAA AGCTTGGGTG TGA                                  453

(2) INFORMATION FOR SEQ ID NO:64:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:64:

GTGCAGTGAG GCATACATCA C                                                21

(2) INFORMATION FOR SEQ ID NO:65:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:65:

-continued

```
AAGGCTGAAT GAAAGGGTAA TTC                                            23

(2) INFORMATION FOR SEQ ID NO:66:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO:66:

CACCCTGCTG CCCAGATATG                                                20

(2) INFORMATION FOR SEQ ID NO:67:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (xi) SEQUENCE DESCRIPTION: SEQ ID NO:67:

CTTATACCAC GAAAGGTAAT ACAC                                           24

(2) INFORMATION FOR SEQ ID NO:68:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (xi) SEQUENCE DESCRIPTION: SEQ ID NO:68:

GAGGTCAAAC CTAGAAAGCT CAC                                            23

(2) INFORMATION FOR SEQ ID NO:69:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO:69:

CCTCTCCTTT GTTAGATGCC                                                20

(2) INFORMATION FOR SEQ ID NO:70:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (xi) SEQUENCE DESCRIPTION: SEQ ID NO:70:

CTAGGTCAAA GCAATATGGA CTC                                            23

(2) INFORMATION FOR SEQ ID NO:71:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (xi) SEQUENCE DESCRIPTION: SEQ ID NO:71:

CATGCGATGG AAAATGAGGT G                                              21
```

(2) INFORMATION FOR SEQ ID NO:72:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:72:

CAGAGATTGT GGTGGAGTTA TTG    23

(2) INFORMATION FOR SEQ ID NO:73:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:73:

GCATTATGAA GGTCCACTGA AG    22

(2) INFORMATION FOR SEQ ID NO:74:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:74:

CTTCAGTGGA CCTTCATAAT GC    22

(2) INFORMATION FOR SEQ ID NO:75:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:75:

CCATACAAAC TATCTGGCTC C    21

(2) INFORMATION FOR SEQ ID NO:76:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:76:

CTGGAATAAG TTTACAGGAT CTTC    24

(2) INFORMATION FOR SEQ ID NO:77:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:77:

GATGATTTCA TGTAGTTTTC AATTC    25

(2) INFORMATION FOR SEQ ID NO:78:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (xi) SEQUENCE DESCRIPTION: SEQ ID NO:78:

GATGGAGAAA GTAGTGATGA GC                                           22

(2) INFORMATION FOR SEQ ID NO:79:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (xi) SEQUENCE DESCRIPTION: SEQ ID NO:79:

AGTCACCAGA TTTCCATATT CTC                                          23

(2) INFORMATION FOR SEQ ID NO:80:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (xi) SEQUENCE DESCRIPTION: SEQ ID NO:80:

AAGATGTTGT TGTCCCTACT ATG                                          23

(2) INFORMATION FOR SEQ ID NO:81:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (xi) SEQUENCE DESCRIPTION: SEQ ID NO:81:

AAGGCTGAAT GAAAGGGTAA TTC                                          23

(2) INFORMATION FOR SEQ ID NO:82:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "5' primer for exon 4-5"

(xi) SEQUENCE DESCRIPTION: SEQ ID NO:82:

CACACCTCTT TCTCTCTATA TATG                                         24

(2) INFORMATION FOR SEQ ID NO:83:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "3' primer for exon 4-5"

(xi) SEQUENCE DESCRIPTION: SEQ ID NO:83:

CACACAAAAG TAATATCACA ACAG            24

(2) INFORMATION FOR SEQ ID NO:84:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "5' primer for exon 17"

(xi) SEQUENCE DESCRIPTION: SEQ ID NO:84:

GTATGTCCAA GATCAAAGTA CAC             23

(2) INFORMATION FOR SEQ ID NO:85:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "3' primer for exon 17"

(xi) SEQUENCE DESCRIPTION: SEQ ID NO:85:

GGTGACAGAG AAAGATCCTA TCTC            24

(2) INFORMATION FOR SEQ ID NO:86:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "5' primer for exon 25"

(xi) SEQUENCE DESCRIPTION: SEQ ID NO:86:

CTGGAATATG CTTTGGAAAG TAGG            24

(2) INFORMATION FOR SEQ ID NO:87:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "3' primer for exon 25"

(xi) SEQUENCE DESCRIPTION: SEQ ID NO:87:

CCAAACTTGG TGAAGTAATT TATGG           25

(2) INFORMATION FOR SEQ ID NO:88:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid -continued (A) DESCRIPTION: /desc = "5' primer for exon 34"

(xi) SEQUENCE DESCRIPTION: SEQ ID NO:88:

CACAGGCTTA ACCAATACGT G                                          21

(2) INFORMATION FOR SEQ ID NO:89:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "3' primer for exon 34"

(xi) SEQUENCE DESCRIPTION: SEQ ID NO:89:

CAGGTAGAAA TAGCCCATGT C                                          21

(2) INFORMATION FOR SEQ ID NO:90:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "5' primer for exon 46"

(xi) SEQUENCE DESCRIPTION: SEQ ID NO:90:

GTCCTTTGGT GAAGCTATTT ATAC                                       24

(2) INFORMATION FOR SEQ ID NO:91:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "3' primer for exon 46"

(xi) SEQUENCE DESCRIPTION: SEQ ID NO:91:

CCAAGTCTTT ATCTCTTCAT CAATGC                                     26

ATAXIA-TELANGIECTASIA GENE AND ITS GENOMIC ORGANIZATION

This application is the National Stage of PCT Application No. PCT/US96/07025, filed May 16, 1996 under 37 CFR 271 which is a continuation in part of U.S. application Ser. No. 08/629, 001, filed Apr. 8, 1996, now U.S. Pat. No. 5,858,661, which is a continuation in part of U.S. application Ser. No. 08/441,822, filed May 16, 1995, now U.S. Pat. No. 5,756,288.

TECHNICAL FIELD

The present invention relates to the determination of the gene sequence, mutations of which cause ataxia-telangiectasia (A-T), designated ATM, and the use of the gene and gene products in detection of carriers of the A-T gene, and preparing native and transgenic organisms in which the gene products encoded by the ATM gene or its homolog in other species are artificially produced, or the expression of the native ATM gene is modified.

BACKGROUND OF THE INVENTION

Ataxia-telangiectasia (A-T) is a progressive genetic disorder affecting the central nervous and immune systems, and involving chromosomal instability, cancer predisposition, radiation sensitivity, and cell cycle abnormalities. Studies of the cellular phenotype of A-T have pointed to a defect in a putative system that processes a specific type of DNA damage and initiates a signal transduction pathway controlling cell cycle progression and repair. For a general review of Ataxia-telangiectasia, reference is hereby made to the review *Ataxia-Telangiectasis: Closer to Unraveling the Mystery*, Eur. J. Hum. Genet. (Shiloh, 1995) which, along with its cited references, is hereby incorporated by reference as well as to the reviews by Harnden (1994) and Taylor et al (1994).

Despite extensive investigation over the last two decades, A-T has remained a clinical and molecular enigma. A-T is a multi-system disease inherited in an autosomal recessive manner, with an average worldwide frequency of 1:40,000–1:100,000 live births and an estimated carrier frequency of 1% in the American population. Notable concentrations of A-T patients outside the United States are in Turkey, Italy and Israel. Israeli A-T patients are Moroccan Jews, Palestinian Arabs, Bedouins and Druzes.

Cerebellar ataxia that gradually develops into general motor dysfunction is the first clinical hallmark and results from progressive loss of Purkinje cells in the cerebellum. Oculocutaneous telangiectasia (dilation of blood vessels) develops in the bulbar conjunctiva and facial skin, and is later accompanied by graying of the hair and atrophic changes in the skin. The co-occurrence of cerebellar ataxia and telangiectases in the conjunctivae and occasionally on the facial skin—the second early hallmark of the disease—usually establishes the differential diagnosis of A-T from other cerebellar ataxias. Somatic growth is retarded in most patients, and ovarian dysgenesis is typical for female patients. Among occasional endocrine abnormalities, insulin-resistant diabetes is predominant, and serum levels of alpha-fetoprotein and carcinoembryonic antigen are elevated. The thymus is either absent or vestigial, and other immunological defects include reduced levels of serum IgA, IgE or IgG2, peripheral lymphopenia, and reduced responses to viral antigens and allogeneic cells, that cause many patients to suffer from recurrent sinopulmonary infections.

Cancer predisposition in A-T is striking: 38% of patients develop malignancies, mainly lymphoreticular neoplasms and leukemias. But, A-T patients manifest acute radiosensitivity and must be treated with reduced radiation doses, and not with radiomimetic chemotherapy. The most common cause of death in A-T, typically during the second or third decade of life, is sinopulmonary infections with or without malignancy.

The complexity of the disease is reflected also in the cellular phenotype. Chromosomal instability is expressed as increased chromosomal breakage and the appearance in lymphocytes of clonal translocations specifically involving the loci of the immune system genes. Such clones may later become predominant when a lymphoreticular malignancy appears. Primary fibroblast lines from A-T patients show accelerated senescence, increased demand for certain growth factors, and defective cytoskeletal structure. Most notable is the abnormal response of A-T cells to ionizing radiation and certain radiomimetic chemicals. While hypersensitive to the cytotoxic and clastogenic effects of these agents, DNA synthesis is inhibited by these agents to a lesser extent than in normal cells. The concomitant lack of radiation-induced cell cycle delay and reduction of radiation-induced elevation of p53 protein are evidence of defective checkpoints at the G1, S and G2 phases of the cell cycle. The G1 and G2 checkpoint defects are evident as reduced delay in cell cycle progression following treatment with ionizing radiation or radiomimetic chemicals, while the rise in the p53 protein level usually associated in normal cells with radiation-induced GI arrest is delayed in A-T cells. The defective checkpoint at the S phase is readily observed as radioresistant DNA synthesis (RDS). Increased intrachromosomal recombination in A-T cells was also noted recently. Cellular sensitivity to DNA damaging agents and RDS are usually considered an integral part of the A-T phenotype. Although these clinical and cellular features are considered common to all "classical" A-T patients, variations have been noted. Milder forms of the disease with later onset, slower clinical progression, reduced radiosensitivity and occasional absence of RDS have been described in several ethnic groups (Fiorilli, 1985; Taylor et al., 1987; Ziv et al., 1989; Chessa et al., 1992). Additional phenotypic variability possibly related to A-T is suggested by several disorders that show "partial A-T phenotype" with varying combinations of ataxia, immunodeficiency and chromosomal instability without telangiectases (12–16) (Ying & Decoteau, 1983; Byrne et al., 1984; Aicardi et al., 1988; Maserati et a;., 1988; Friedman & Weitberg, 1993). Still, other disorders display the A-T phenotype and additional features; most notable is the Nijmegen breakage syndrome that combines A-T features with microcephaly, sometimes with mental retardation, but without telangiectases (Weemaes et al., 1994).

Prenatal diagnoses of A-T using cytogenetic analysis or measurements of DNA synthesis have been reported, but these tests are laborious and subject to background fluctuations and, therefore, not widely used.

A-T homozygotes have two defective copies of the A-T gene and are affected with the disease. A-T heterozygotes (carriers) have one normal copy of the gene and one defective copy of the gene and are generally healthy. When two carriers have children, there is a 25% risk in every pregnancy of giving birth to an A-T affected child.

A-T heterozygotes show a significant excess of various is malignancies, with a 3- to 4-fold increased risk for all cancers between the ages of 20 and 80, and a 5-fold increased risk of breast cancer in women. These observations turn A-T into a public health problem and add an important dimension to A-T research, particularly to heterozygote identification. Cultured cells from A-T heterozygotes indeed show an intermediate degree of X-ray sensitivity, but the difference from normal cells is not always large enough to warrant using this criterion as a laboratory assay for carrier detection. The main reason for the unreliability of this assay is the various degrees of overlap between A-T heterozygotes and non-heterozygotes with respect to radiosensitivity. Cytogenetic assays for carriers have the same problems as for prenatal diagnosis, they are labor intensive and not always consistent.

The nature of the protein missing in A-T is unknown.

Cell fusion studies have established four complementation groups in A-T, designated A, C, D and E, suggesting the probable involvement of at least four genes or four types of mutations in one gene, with inter-allelic complementation. These four groups are clinically indistinguishable and were found to account for 55%, 28%, 14% and 3% of some 80 patients typed to date. In Israel, several Moroccan Jewish patients were assigned to group C, while Palestinian Arab patients were assigned to group A.

The general chromosomal localization of the putative A-T gene(s) has been determined, but not the sequence. An A-T locus containing the A-T(A) mutations was localized by Gatti et al. (1988) to chromosome 11, region q22–23, using linkage analysis. The A-T(C) locus was localized by applicant to the same region of chromosome 11, region q22–23, by linkage analysis of an extended Jewish Moroccan A-T family (Ziv et al., 1991). Further studies, conducted by an international consortium in which applicant participated (McConville et al., 1990; Foroud et al., 1991; Ziv et al., 1992), reconfirmed this localization in a series of studies and gradually narrowed the A-T locus to an interval estimated at 4 centimorgan, which probably contains also the A-T(E) mutations.

A proposed gene for complementation group D is disclosed in U.S. Pat. No. 5,395,767 to Murnane et al., issued Mar. 7, 1995. This sequence was found not to be mutated in any complementation group of A-T. Further, the gene sequence was mapped physically distant from the presumptive A-T locus.

Therefore, in order to better understand the nature and effects of A-T, as well as to more accurately and consistently determine those individuals who may carry the defective gene for A-T, it would be advantageous to isolate and determine the gene sequence, mutations of which are responsible for causing A-T, and utilize this sequence as a basis for detecting carriers of A-T and thereby be able to more beneficially manage the underlying conditions and predispositions of those carriers of the defective gene.

SUMMARY OF THE INVENTION AND ADVANTAGES

According to the present invention, a gene, designated ATM, mutations of which cause ataxia-telangiectasia (A-T) has been purified, isolated and sequenced, as well as mutations of the gene and the genomic organization of the gene has been determined.

The present invention further includes the method for identifying carriers of the defective A-T gene in a population and defective A-T gene products.

The role of the ATM gene in cancer predisposition makes this gene an important target for screening. The detection of A-T mutation carriers is particularly significant in light of their radiation-sensitivity so that carrier exposure to radiation can be properly monitored and avoided.

BRIEF DESCRIPTION OF THE DRAWINGS

Other advantages of the present invention will be readily appreciated as the same becomes better understood by reference to the following detailed description when considered in connection with the accompanying drawings wherein:

FIGS. 1A–E illustrate the positional cloning steps to identify the A-T gene(s) wherein FIG. 1A is a high-density marker map of the A-T region on chromosome 11q22–23 (vanagaite et al., 1995), constructed by generating microsatellite markers within genomic contigs spanning the region and by physical mapping of available markers using the same contigs, the prefix "D11" has been omitted from the marker designations, FDX: the adrenal ferredoxin gene, ACAT: the acetoacetyl-coenzyme A thiolase gene, the stippled box denotes the A-T interval, defined recently by individual recombinants between the markers S1818 and S1819 in a consortium linkage study (Lange et al., 1995), the solid box indicates the two-lod confidence interval for A-T obtained in that study, between S1294 and S384;

FIG. 1B illustrates a part of a YAC contig constructed across this region (Rotman et al., 1994c);

FIG. 1C illustrates part of a cosmid contig spanning the S384–S1818 interval, generated by screening a chromosome-11 specific cosmid library with YAC clones Y16 and Y67, and subsequent contig assembly of the cosmid clones by physical mapping (Shiloh, 1995);

FIG. 1D illustrates products of gene hunting experiments wherein solid boxes denote cDNA fragments obtained by using cosmid and YAC clones for hybrid selection of cDNAs (Lovett et al. 1991; Tagle et al., 1993) from a variety of tissues, open boxes denote putative exons isolated from these cosmids by exon trapping (Church et al., 1993), these sequences hybridized back to specific cosmids (broken lines), which allowed their physical localization to specific subregions of the contig (dotted frames); and FIG. 1E illustrates a 5.9 kb cDNA clone, designated 7-9 (SEQ ID No:1), identified in a fibroblast cDNA library using the cDNA fragments and exons in iD as a probe wherein the open box denotes an open reading frame of 5124 nucleotides, solid lines denote untranslated regions, striped arrowheads denote two Alu elements at the 3' end, and wherein dotted lines drawn between cDNA fragments and exons the cDNA indicate colinearity of sequences;

DETAILED DESCRIPTION OF THE PREFERRED EMBODIMENT

The present invention consists of a purified, isolated and cloned nucleic acid sequence (SEQ ID Nos:2, 8–10, 11–63) encoding a gene, designated ATM, mutations in which cause ataxia-telangiectasia and genetic polymorphisms thereof. The nucleic acid can be genomic DNA, cDNA or mRNA.

The complete coding sequence of the ATM gene is set forth in SEQ ID No:2 and was submitted to the GenBank database under accession number U33841. There is extensive alternate splicing at the 5' untranslated region (5'UTR) of the ATM transcript giving rise to twelve different 5' UTRs. The sequence of the longest 5'UTR is set forth in SEQ ID No:9. The first exon in this sequence is designated 1b. There is an alternative leader exon, designated 1a (SEQ ID No:10). The sequence of the complete 3'UTR is set forth in SEQ ID No:8. Together these sequences contain the complete sequence of the ATM transcript. The genomic sequence for each exon and flanking intronic sequences are set forth in Tables 1 and 5, and SEQ ID Nos:11–63.

As shown in Example 4, using long-distance PCR, the genomic organization, i.e. structure, of this gene was determined and the exon-intron boundaries identified. The ATM gene spans approximately 150 kb of genomic DNA and consists of 66 (64 plus two alternative exon 1) exons. The initiation codon falls within the fifth exon. The last exon is 3.6 kb long and contains the stop codon and a 3' untranslated region of about 3800 nucleotides.

Figure 3:
FIG. 3 is a schematic representation of the exon-intron organization of the ATM gene with vertical-lines denoting the position of the ATM exons, the 3' exon and all introns are drawn to scale.

The ATM gene is composed of 66 exons (FIG. 3 and Tables 1 and 5). The first two exons are alternatively spliced, and are designated 1a (SEQ ID No:10) and 1b (SEQ ID No:9). With the exception of the 3' exon, ATM exons (SEQ ID Nos:11–63) range in size from 64 to 372 bp, with an average of 149 bp. The introns vary considerably in size, from 100 bp to about 11 kb, with the majority in the range of 1–3 kb. The consensus dinucleotides GT and AG were found at the donor and acceptor splice sites of all introns, except for a variant donor site with a GC dinucleotide (reviewed in Jackson, 1991) present in the intron 3' to exon 52. The first methionine of the open reading frame is located in exon 4, whereas the stop codon is located in the 3' and largest exon of 3.6 kb (Exon 65; SEQ ID No:63). This exon includes a 3' untranslated region (UTR) (SEQ ID No:8) of about 3800 nucleotides.

Polymorphisms are variants in the sequence generally found between different ethnic and geographic locations which, while having a different sequence, produce functionally equivalent gene products.

Current mutation data (as shown in Tables 2 and 3) indicate that A-T is a disease characterized by considerable allelic heterogeneity. Mutations imparting defects into the A-T gene can be point mutations, deletions or insertions. The mutations can be present within the nucleotide sequence of either/or both alleles of the ATM gene such that the resulting amino acid sequence of the ATM protein product is altered in one or both copies of the gene product; when present in both copies imparting ataxia-telangiectasia. Alternatively, a mutation event selected from the group consisting of point mutations, deletions, insertions and rearrangements could have occurred within the flanking sequences and/or regulatory sequences of ATM such that regulation of ATM is altered imparting ataxia-telangiectasia.

Table 2 illustrates ten mutations in the ATM gene found in A-T patients. Mutations in the ATM gene were found in all of the complementation groups suggesting that ATM is the sole gene responsible for all A-T cases.

Figure 4:
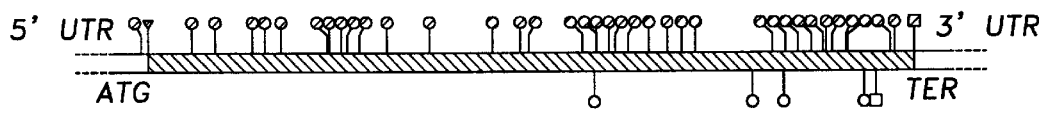
FIG. 4 is a schematic representation of 44 A-T mutations along the open reading frame (diagonal lines) of the ATM transcript, wherein for large deletions the symbols mark the locations of the 5' breakpoints, symbols above the line designate mutations expected to inactivate the ATM protein and symbols below the line designate mutations which a priori may have a milder phenotype, symbols are as follows ● truncations and exon skipping deletions (37), ▼ initiation codon abolished (1), ■ termination codon abolished (1), ○ in-frame genomic deleteions and insertions of ≦9 bp (4), and □ missense mutations (1).

Table 3 and FIG. 4 illustrate 54 mutations identified to date in applicant's patient cohort and include 44 new ones and 10 previously listed in Table 2. These mutations were found amongst 55 A-T families: many are unique to a single family, while others are shared by several families, most notably the 4 nt deletion, 7517del4, which is common to 6 A-T families from South-Central Italy. The nature and location of A-T mutations, as set forth in Table 3, provide insight into the function of the ATM protein and the molecular basis of this pleiotropic disease.

This series of 54 A-T mutations is dominated by deletions and insertions. The smaller ones, of less than 12 nt, reflect identical sequence alterations in genomic DNA. Deletions spanning larger segments of the ATM transcript were found to reflect exon skipping, not corresponding genomic deletions. Of the 54 A-T mutations identified, 45 (83.3%) are expected to inactivate the ATM protein by truncating it, by abolishing correct initiation or termination of translation, or by deleting large segments. Additional mutations are four smaller in-frame deletions and insertions, and one substitution of a highly conserved amino acid at the PI 3-kinase domain. The emerging profile of mutations causing. A-T is thus dominated by those expected to completely inactivate the ATM protein. ATM mutations with milder effects appear to result in phenotypes related, but not identical, to A-T. In view of the pleiotropic nature of the ATM gene, the range of phenotypes associated with various ATM genotypes may be even broader, and include mild progressive conditions not always defined as clear clinical entities as discussed herein below in Example 3. Screening for mutations in this gene in such cases will reveal wider boundaries for the molecular pathology associated with the ATM gene. The present invention therefore allows the identification of these mutations in subjects with related phenotypes to A-T.

The ATM gene leaves a great deal of room for mutations: it encodes a large transcript. The variety of mutations identified in this study indeed indicates a rich mutation repertoire. Despite this wealth of mutations, their structural characteristics point to a definite bias towards those that inactivate or eliminate the ATM protein. The nature or distribution of the genomic deletions among these. mutations do not suggest a special preponderance of the ATM gene for such mutations, such as that of the dystrophin (Anderson and Kunkel, 1992) or steroid sulfatase (Ballabio et al., 1989) genes which are particularly prone to such deletions. Thus, one would have expected also a strong representation of missense mutations, which usually constitute a significant portion of the molecular lesions in many disease genes (Cooper and Krawczak, 1993; Sommer, 1995). However, only two such mutations were identified in the present study. Other point mutations reflected in this series are those that probably underlie the exon skipping deletions observed in many patients, again, exerting a severe structural effect on the ATM protein.

In cloning the gene for A-T (see Example 2), the strategy used was a standard strategy in identifying a disease gene with an -unknown protein product known as positional cloning, as is well known in the art. In positional cloning, the target gene is localized to a specific chromosomal region by establishing linkage between the disease and random genetic markers defined by. DNA polymorphisms. Definition of the smallest search interval for the gene by genetic analysis is followed by long-range genomic cloning and identification of transcribed sequences within the interval. The disease gene is then identified among these sequences, mainly by searching for mutations in patients.

Several important and long sought disease genes were isolated recently in this way (Collins, 1992; Attree et al., 1992; Berger et al., 1992; Chelly et al., 1993; Vetrie et al., 1993; Trofatter et al., 1993; The Huntington's Disease Collaborative Research Group, 1993; The European Polycystic Kidney Disease Consortium, 1994; Miki et al., 1994).

Two complementary methods were used for the identification of transcribed sequences (gene hunting): hybrid selection based on direct hybridization of genomic DNA with cDNAs from various sources (Parimoo et al., 1991; Lovett et al., 1991); and exon trapping (also called exon amplification), which identifies putative exons in genomic DNA by virtue of their splicing capacity (Church et al., 1993). In hybrid selection experiments, cosmid and YAC clones served to capture cross-hybridizing sequences in cDNA collections from placenta, thymus and fetal brain, using the magnetic bead capture protocol (Morgan et al., 1992; Tagle et al., 1993). In parallel experiments, YAC clones were bound to a solid matrix and used to select cDNA fragments from a heterogeneous cDNA collection representing several human tissues (Parimoo et al., 1993). The cosmids were also used for exon trapping with the pSPL3 vector (Church et al., 1994). The captured cDNA fragments and trapped exons were mapped back to the A-T region by hybridization to several radiation hybrids containing various portions of the 11q22–23 region (Richard et al., 1993; James et al., 1994), and to high-density grids containing all the YACs and cosmids spanning this interval. An extensive transcriptional map of the A-T region was thus constructed (Shiloh et al., 1994a).

Pools of adjacent cDNA fragments and exons, expected to converge into the same transcriptional units, were used to screen cDNA libraries. A cluster of 5 cDNA fragments and 3 exons mapped in close proximity to the marker D11S535, where the location score for A-T had peaked (Lange et al., 1995). All these sequences hybridized to the same 5.9 kb of the cDNA clone, 7-9, (SEQ ID No:1) obtained from a fibroblast cDNA library.

Hybridization of the 7-9 cDNA clone to the radiation hybrid panel indicated that the entire transcript was derived from the chromosome 11 locus. The full sequence of this clone (SEQ ID No:1) was obtained using a shotgun strategy, and found to contain 5921 bp which includes an open reading frame (ORF) of 5124 nucleotides, a 538 bp 3' untranslated region (3' UTR), and a 259 bp 5' non-coding sequence containing stop codons in all reading frames. (Genbank Accession No. U26455). Two Alu repetitive elements were observed at the 3' end of this clone and in nine smaller clones representing this gene from the same cDNA library. Since no polyadenylation signal was identified in these cDNA clones, their poly(A) tracts were assumed to be associated with the Alu element rather than being authentic poly(A) tails of these transcripts. This assumption was later supported when applicants identified a cDNA clone derived from the same gene in a leukocyte cDNA library, with an alternative 3' UTR containing a typical polyadenylation signal. Alignment of the cDNA with the genomic physical map showed that the corresponding gene is transcribed from centromere to telomere.

Hybridization of a probe containing the entire ORF of clone 7-9 to northern blots from various tissues and cell lines revealed a major transcript of 12 kb, later shown to be 13 kb, in all tissues and cell types examined, and minor species of various sizes in several tissues, possibly representing alternatively spliced transcripts of the corresponding gene or other homologous sequences. Genomic sequencing later identified the 5' non-coding region of clone 7-9 as sequences of the unspliced adjacent intron. Two other cDNA clones from a leukocyte cDNA library were found to contain this intronic sequence in their 5' ends. These clones may represent splicing intermediates.

Figure 2:
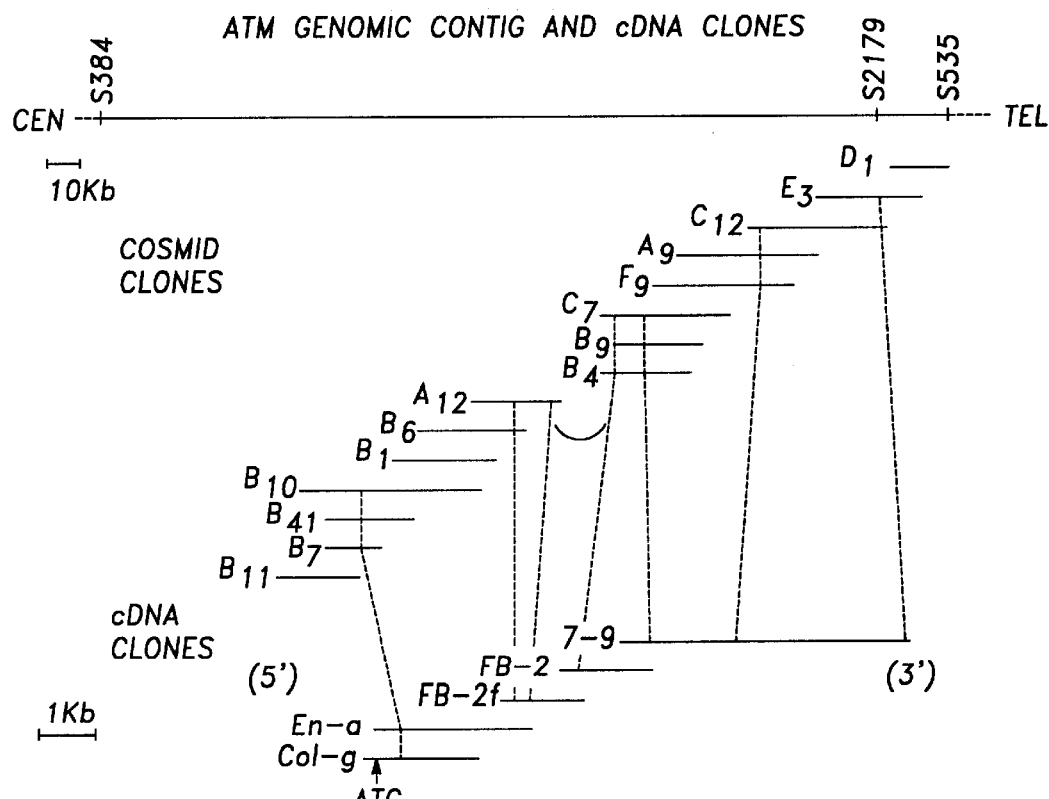
FIG. 2 is a diagram of the physical map of the ATM region and relationship to the cDNA wherein the top line represents a linear map of the region containing known genetic markers (the prefix D11 has been omitted from marker designations) and shown below the linear map is a portion of a cosmid contig spanning the region with the arch between ends of cosmids A12 and B4 represents a genomic PCR product, a contig of cDNA clones which span the ATM ORF is shown at the bottom of the figure, broken lines denote the position of specific cDNA sequences with the cosmid contig.

The 7-9 cDNA clone represents only part of the ATM gene transcript. Successive screening of randomly-primed cDNA libraries identified a series of partly overlapping cDNA clones and enabled the construction of a cDNA contig of about 10 Kb (FIG. 2). The gene coding for this transcript spans about 150 Kb of genomic DNA.

The composite cDNA of 9860 bp (GenBank Accession No. U33841; SEQ ID No:2) includes an open reading frame of 9168 nucleotides, a 538 bp 3' untranslated region (UTR), and a 164 bp 5' UTR containing stop codons in all reading frames. The sequence surrounding the first in-frame initiation codon (ACC<u>ATG</u>A) resembles the consensus sequence proposed by Kozak et al (1987) for optimal initiation of translation, (A/G)CC<u>ATG</u>G. No polyadenylation signal was found at the 3' UTR. The same poly(A) tail was found in all cDNA clones and 3' RACE products isolated to date in applicant's laboratory, however, this poly(A) tail most likely belongs to the Alu element contained in the 3' UTR.

Sequencing and PCR analysis of 32 partial ATM cDNA clones, obtained from 11 cDNA libraries representing 8 different tissues, have been colinear over the coding region, except when they contained unspliced intronic sequences. Thus, alternative splicing within the ATM coding region may not occur, or may take place at a very low frequency, or be restricted to a cell type not yet explored.

The invention further provides a purified protein (SEQ ID No:3) as encoded by the ATM gene and analogs and mutations thereof (SEQ ID No:2). The present invention further provides for mutations in SEQ ID No:3 which cause ataxia-telangiectasia, for example, as set forth in Tables 2 and 3.

Th2 ATM Open Reading Frame (SEQ ID No:2) product is a large protein of 3056 amino acids, with an expected molecular weight-of 350.6 kDa. The ATM gene product (SEQ ID No:3) contains a PI-3 kinase signature at codons 2855–2875, and a potential leucine zipper at codons 1217–1238. The presence of this leucine zipper may suggest possible dimerization of the ATM protein or interaction with additional proteins. No nuclear localization signal, transmembrane domains or other motifs were observed in this protein sequence.

The ATM gene product is a member of a family of large proteins that share a highly conserved carboxy-terminal region of about 300 amino acids showing high sequence homology to the catalytic domain of PI-3 kinases. Among these proteins are Tel1p and Mec1p in budding yeast, rad3p in fission yeast, the TOR proteins in yeast and their mammalian counterpart, FRAP (RAFT1), MEI-41 in *Drosophila melanogaster*, and the catalytic subunit of DNA-dependent protein kinase (DNA-PKcs) in mammals. All of these proteins are implicated in cell cycle control and some of them, like Mec1p, rad3p and DNA-PKcs are involved in response to DNA damage (Table 4). The central core of the PI-3 kinase-like domain contains two subdomains with highly conserved residues present in nearly all kinases, including protein and PI-3 kinases. The residues Asp and Asn (at positions 2870 and 2875 in ATM), and the triplet Asp-Phe-Gly (at positions 2889–2891), which represents the most highly conserved short stretch in the protein kinase catalytic domain, have been implicated in the binding of ATP and phosphotransferase activity. Mutations in the genes encoding these proteins result in a variety of phenotypes that share features with A-T, such as radiosensitivity, chromosomal instability, telomere shortening., and defective cell cycle checkpoints (reviewed by Savitsky et al., 1995a and b; Zakian, 1995).

A possible working model for the ATM protein's function is DNA-PK, a serine/threonine protein kinase that is activated in vitro by DNA double-strand breaks and responds by phosphorylating several regulator proteins (Gottlieb and Jackson, 1994). The ATM protein may be responsible for conveying a signal evoked by a specific DNA damage to various checkpoint systems, possibly via lipid or protein phosphorylation.

The present invention further includes a recombinant protein encoded by SEQ ID No:2 or SEQ ID No:3 or analogs thereof. This recombinant protein is isolated and purified by techniques known to those skilled in the art.

An analog will be generally at least 70% homologous over any portion that is functionally relevant. In more preferred embodiments, the homology will be at least 80% and can approach 95% homology to the ATM protein. The amino acid sequence of an analog may differ from that of the ATM protein when at least one residue is deleted, inserted or substituted but the protein remains functional and does not cause A-T. Differences in glycosylation can provide analogs.

The present invention provides an antibody, either polyclonal or monoclonal, which specifically binds to epitopes on the polypeptide/protein encoded by the ATM gene, or mutant epitopes. In preparing the antibody, the protein (with and without mutations) encoded by the ATM gene and polymorphisms thereof is used as a source of the immunogen. Peptide amino acid sequences isolated from the amino acid sequence as set forth in SEQ ID No:3 or mutant peptide sequences can also be used as an immunogen.

The present invention also provides antibodies against the following peptides:
HEPANSSASQSTDLC (SEQ ID No:4),
CKRNLSDIDQSFDKV (SEQ ID No:5),
PEDETELHPTLNADDQEC (SEQ ID No:6), and
CKSLASFIKKPFDRGEVESMEDDTNG (SEQ ID No:7).

The antibodies may be either monoclonal or polyclonal. Conveniently, the antibodies may be prepared against a synthetic peptide based on the sequence, or prepared recombinantly by cloning techniques or the natural gene product and/or portions thereof may be isolated and used as the immunogen. Such proteins or peptides can be used to produce antibodies by standard antibody production technology well known to those skilled in the art as described generally in Harlow and Lane, *Antibodies: A Laboratory Manual*, Cold Spring Harbor Laboratory Press, Cold Spring Harbor, N.Y., 1988.

For producing polyclonal antibodies a host, such as a rabbit or goat, is immunized with the protein or peptide, generally with an adjuvant and, if necessary, coupled to a carrier; antibodies to the protein are collected from the sera.

For producing monoclonal antibodies, the technique involves hyperimmunization of an appropriate donor, generally a mouse, with the protein or peptide fragment and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

The antibody can be bound to a solid support substrate or conjugated with a detectable moiety or be both bound and conjugated as is well known in the art. (For a general discussion of conjugation of fluorescent or enzymatic moieties see Johnstone and Thorpe, *Immunochemistry in Practice*, Blackwell Scientific Publications, Oxford, 1982.) The binding of antibodies to a solid support substrate is also well known in the art. (see for a general discussion Harlow and Lane *Antibodies: A Laboratory Manual*, Cold Spring Harbor Laboratory Publications, New York, 1988) The detectable moieties contemplated with the present invention can include, but are not limited to, fluorescent, metallic, enzymatic and radioactive markers such as biotin, gold,. ferritin, alkaline phosphatase, β-galactosidase, peroxidase, urease, fluorescein, rhodamine, tritium, $^{14}$C and iodination.

The present invention provides vectors comprising an expression control sequence operatively linked to the nucleic acid sequence of the ATM gene, SEQ ID No:2 and portions thereof as well as mutant sequences which lead to the expression of A-T. The present invention further provides-host cells, selected from suitable eucaryotic and procaryotic cells, which are transformed with these vectors.

Using the present invention, it is possible to transform host cells, including *E. coli*, using the appropriate vectors so that they carry recombinant DNA sequences derived from the ATM transcript or containing the entire ATM transcript in its normal form or a mutated sequence containing point mutations, deletions, insertions, or rearrangements of DNA. Such transformed cells allow the study of the function and the regulation of the A-T gene. Use of recombinantly transformed host cells allows for the study of the mechanisms of A-T and, in particular it will allow for the study of gene function interrupted by the mutations in the A-T gene region.

Vectors are known or can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids and-other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1992), in Ausubel et al., *Current Protocols in Molecular Biology*, John Wiley and Sons, Baltimore, Maryland (1989), Chang et al., *Somatic Gene Therapy*, CRC Press, Ann Arbor, Mich. (1995), Vega et al., *Gene Targeting*, CRC Press, Ann Arbor, Mich. (1995) and Gilboa et al (1986) and include, for example, stable or transient transfection, lipofection, electroporation and infection with recombinant viral vectors. Introduction of nucleic acids by infection offers several advantages over the other listed methods. Higher efficiency can be obtained due to their infectious nature. See also U.S. Pat. Nos. 5,487,992 and 5,464,764. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

Recombinant methods known in the art can also be used to achieve the sense, antisense or triplex inhibition of a target nucleic acid. For example, vectors containing antisense nucleic acids can be employed to express protein or antisense message to reduce the expression of the target nucleic acid and therefore its activity.

A specific example of DNA viral vector for introducing and expressing antisense nucleic acids is the adenovirus derived vector Adenop53TK. This vector expresses a herpes virus thymidine kinase (TK) gene for either positive or. negative selection and an expression cassette for desired recombinant sequences such as antisense sequences. This vector can be used to infect cells that have an adenovirus receptor which includes most cancers of epithelial origin as well as others. This vector as well as others that exhibit similar desired functions can be used to treat a mixed population of cells include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the anti-viral gancyclovir. Negative selection is therefore a means by which infection can be controlled because it provides inducible suicide through the addition of antibiotic. Such protection ensures that if, for example, mutations arise that produce altered forms of the viral vector or sequence, cellular transformation will not occur. Features that limit expression to particular cell types can also be included. Such features include, for example, promoter and regulatory elements that are specific for the desired cell type.

Recombinant viral vectors are another example of vectors useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted. For example, if breast cancer is to be treated, then a vector specific for such epithelial cells should be used. Likewise, if diseases or pathological conditions of the hematopoietic system are to be treated, then a viral vector that is specific for blood cells and their precursors, preferably for the specific type of hematopoietic cell, should be used.

Retroviral vectors can be constructed to function either as infectious particles or to undergo only a single initial round of infection in the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

If viral vectors are used, for example, the procedure can take advantage of their target specificity and consequently, do not have to be administered locally at the diseased site. However, local administration may provide a quicker and more effective treatment, administration can also be performed by, for example, intravenous or subcutaneous injection into the subject. Injection of the viral vectors into a spinal fluid can also be used as a mode of administration, especially in the case of neurodegenerative diseases. Following injection, the viral vectors will circulate until they recognize host cells with the appropriate target specificity for infection.

Transfection vehicles such as liposomes can also be used to introduce the non-viral vectors described above into recipient cells within the inoculated area. Such transfection vehicles are known by one skilled within the art.

The present invention includes the construction of transgenic and knockout organisms that exhibit the phenotypic manifestations of A-T. The present invention provides for transgenic ATM gene and mutant ATM gene animal and cellular (cell lines) models as well as for knockout ATM models. The transgenic model can include those carrying the sequence set forth SEQ ID Nos:2,8,9 (or 10). These models are constructed using standard methods known in the art and as set forth in U.S. Pat. Nos. 5,487,992, 5,464,764, 5,387,742, 5,360,735, 5,347,075, 5,298,422, 5,288,846, 5,221,778, 5,175,385, 5,175,384,5,175,383, 4,736,866 as well as Burke and Olson, (1991), Capecchi, (1989), Davies et al., (1992), Dickinson et al., (1993), Huxley et al., (1991), Jakobovits et al., (1993), Lamb et al., (1993), Rothstein, (1991), Schedl et al., (1993), Strauss et al., (1993). Further, patent applications WO 94/23049, WO 93/14200, WO 94/06908, WO 94/28123 also provide information. See also in general Hogan et al "Manipulating the Mouse Embryo" Cold Spring Harbor Laboratory Press, 2nd Edition (1994).

According to the present invention, there is provided a method for diagnosing and detecting carriers of the defective gene responsible for causing A-T (see Example 4).

The present invention further provides methods for detecting normal copies of the ATM gene and its gene product. Carrier detection is especially important since A-T mutations underlie certain cases of cancer predisposition in the general population. Identifying the carriers-either by their defective gene or by their missing or defective protein (s) encoded thereby, leads to earlier and more consistent diagnosis of A-T gene carriers. Thus, since carriers of the disease are more likely to be cancer-prone and/or sensitive to therapeutic applications of radiation, better surveillance and treatment protocols can be initiated for them. Conversely, exclusion of A-T heterozygotes from patients undergoing radiotherapy can allow for establishing routinely higher dose schedules for other cancer patients thereby improving the efficacy of their treatment.

Briefly, the methods comprise the steps of obtaining a sample from a test subject, isolating the appropriate test material from the sample and assaying for the target nucleic acid sequence or gene product. The sample can be tissue or bodily fluids from which genetic material and/or proteins are isolated using methods standard in the art. For example, DNA can be isolated from lymphocytes, cells in amniotic fluid and chorionic villi (Llerena et al., 1989).

More specifically, the method of carrier detection is carried out by first obtaining a sample of either cells or bodily fluid from a subject. Convenient methods for obtaining a cellular sample can include collection of either mouth wash fluids or hair roots. A cell sample could be amniotic or placental cells or tissue in the case of a prenatal diagnosis. A crude DNA could be made from the cells (or alternatively proteins isolated) by techniques well known in the art. This isolated target DNA is then used for PCR analysis (or alternatively, Western blot analysis for proteins from a cell line established from the subject) with appropriate primers derived from the gene sequence by techniques well known in the art. The PCR product would then be tested for the presence of appropriate sequence variations in order to assess genotypic A-T status of the subject.

The specimen can be assayed for polypeptides/proteins by immunohistochemical and immunocytochemical staining (see generally Stites and Terr, *Basic and Clinical Immunology*, Appleton and Lange, 1994), ELISA, RIA, immunoblots, Western blotting, immunoprecipitation, functional assays and protein truncation test. In preferred embodiments, Western blotting, functional assays and protein truncation test (Hogervorst et al., 1995) will be used. mRNA complementary to the target nucleic acid sequence can be assayed by in situ hybridization, Northern blotting and reverse transcriptase-polymerase chain reaction. Nucleic acid sequences can be identified by in situ hybridization, Southern blotting, single strand conformational polymorphism, PCR amplification and DNA-chip analysis using specific primers. (Kawasaki, 1990; Sambrook, 1992; Lichter et al, 1990; Orita et al, 1989; Fodor et al., 1993; Pease et al., 1994)

ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, 1992.

Current mutation data (as shown in Tables 2 and 3) indicate that A-T is a disease characterized by considerable allelic heterogenicity. It is not surprising that there are hundreds (or even thousands) of ATM mutations (as is the case for cystic fibrosis and BRCA1) as shown in Table 3. Thus, it will be important for a successful mutation screen to be able to detect all possible nucleotide alterations in the ATM gene, rather than being focused on a limited subset (see Example 4). Methods including direct sequencing of PCR amplified DNA or RNA or DNA chip hybridization (Fodor et al., 1993; Pease et al., 1994) can be applied along with other suitable methods known to those skilled in the art.

In order to use the method of the present invention for diagnostic applications, it is advantageous to include a mechanism for identifying the presence or absence of target polynucleotide sequence (or alternatively proteins). In many hybridization based diagnostic or experimental procedures, a label or tag is used to detect or visualize for the presence or absence of a particular polynucleotide sequence. Typically, oligomer probes are labelled with radioisotopes such as $^{32}P$ or $^{35}S$ (Sambrook, 1992) which can be detected by methods well known in the art such as autoradiography. Oligomer probes can also be labelled by non-radioactive methods such as chemiluminescent materials which can be detected by autoradiography (Sambrook, 1992). Also, enzyme-substrate based labelling and detection methods can be used. Labelling can be accomplished by mechanisms well known in the art such as end labelling (Sambrook, 1992), chemical labelling, or by hybridization with another labelled oligonucleotide. These methods of labelling and detection are provided merely as examples and are not meant to provide a complete and exhaustive list of all the methods known in the art.

The introduction of a label for detection purposes can be accomplished by attaching the label to the probe prior to hybridization.

An alternative method for practicing the method of the present invention includes the step of binding the target DNA to a solid support prior to the application of the probe. The solid support can be any material capable of binding the target DNA, such as beads or a membranous material such as nitrocellulose or nylon. After the target DNA is bound to the solid support, the probe oligomers is applied.

Functional assays can be used for detection of A-T carriers-or affected individuals. For example, if the ATM protein product is shown to have PI 3-kinase or a protein kinase biochemical activity which can be assayed in an accessible biological material, such as serum, peripheral leukocytes, etc., then homozygous normal individuals would have approximately normal biological activity and serve as the positive control. A-T carriers would have substantially less than normal biological activity, and affected (i.e. homozygous) individuals would have even less biological activity and serve as a negative control. Such a biochemical assay currently serves as the basis for Tay-Sachs carrier detection.

The present invention provides a method for a rapid and efficient method to identify any mutations in small amounts of RNA, such as those that are obtained from as little as 100 µl of peripheral blood. RNA is extracted from the sample, using the Tri-Reagent system (Molecular Research Center, Cincinnati Ohio) or other equivalent method and it is subjected to reverse transcription as described by Gilad et al (1996). A selected open reading frame is then amplified using RT-PCR as described herein below, and the resulting products are further amplified using nested PCR primers. The products of these reactions are then subjected to restriction endonuclease fingerprinting (REF) as described hereinbelow.

This method uses the cDNA obtained from the RNA for only one PCR, the products of which later serve for further analysis. Therefore, only minimal amounts of RNA need be extracted, reducing costs.

Using this method RNA isextracted from a sample and subjected to-reverse transcription (Gilad et al., 1996). The entire ATM open reading frame (SEQ ID No:2) is then amplified using RT-PCR as described herein below, and the resulting products are further amplified using nested PCR primers (SEQ ID Nos:82–91; see herein below). The products of these reactions are then subjected to restriction endonuclease fingerprinting (REF) as described hereinbelow.

However, when only genomic DNA (as for example old tumor specimens) is available the preferred embodiment to undertake mutation analysis requires individual amplification of exons or groups of exons. To undertake this analysis primer pairs have been developed based on the information set forth in Table 1 and in Table 5 which is a further amplification of Table 1. Primers are selected from the flanking sequences using standard computer algorithms as are known in the art. Shown below are five examples of primer pairs which can be used for the analysis.

Primers Exons 4 and 5
   5' primer: 5'-cacacctctttctctctatatatg-3' (SEQ ID No:82)
   3' primer: 5'-cacacaaaagtaatatcacaacag-3' (SEQ ID No:83)

Primers Exon 17
   5' primer: 5'-gtatgtccaagatcaaagtacac-3' (SEQ ID No:84)
   3' primer: 5'-ggtgacagagaaagatcctatctc-3' (SEQ ID No:85)

Primers Exon 25
   5' primer: 5'-ctggaatatgctttggaaagtagg-3' (SEQ ID No:86)
   3' primer: 5'-ccaaacttggtgaagtaatttatgg-3' (SEQ ID No:87)

Primers Exon 34
   5' primer: 5'-cacaggcttaaccaatacgtg-3' (SEQ ID No:88)
   3' primer: 5'-caggtagaaatagcccatgtc-3' (SEQ ID No:89)

Primers Exon 46
   5' primer: 5'-gtcctttggtgaagctatttatac-3' (SEQ ID No:90)
   3' primer: 5'-ccaagtctttatctcttcatcaatgc-3' (SEQ ID No:91)

The present invention also provides a kit for diagnosis and detection of the defective A-T gene in a population. In general the population will be one that has been characterized for ATM mutations. For example Moroccan Jews in which only one mutation is known, or a population such as the Amish in which also one mutation is known. Each kit would be customized to the population being screened. The kit includes a molecular probe(s) complementary to genetic sequences of the defective gene which causes ataxia-telangiectasia (A-T) in that population and suitable labels for detecting hybridization of the molecular probe and the defective gene thereby indicating the presence of the defective gene. The molecular probe has a DNA sequence complementary to mutant sequences. Alternatively, the kit can contain reagents and antibodies for detection of mutant proteins.

The above discussion provides a factual basis for the use and identification of the ataxia-telangiectasia gene and gene products and identification of carriers as well as construction of transgenic organisms. The methods used in the present invention can be shown by the following non-limiting example and accompanying figures.

EXAMPLES

Materials and Methods

General methods in molecular biology: Standard molecular biology techniques known in the art and not specifically described were generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Protein analysis techniques are as generally described in Coligan et al., *Current Protocols in Immunology*, John Wiley and Sons, Baltimore, Md. (1992, 1994).

RT-PCR

Following reverse transcription (Gilad et al., 1996), RT-PCR is performed in 25 μl reaction mix. One tenth (1 μl) of the reverse transcription products are added to the reaction mix. The reaction mix contains 2U of Expand Long Template PCR System (Boehringer Mannheim, Mannheim, Germany), in an appropriate buffer containing 1.75 mM MgCl$_2$, 1.5 μg of Antitaq mAb (Chimerx), 0.2 mM dNTPs (Pharmacia) and 1 mM of each of the following primers:

a. 5'-gtgcagtgaggcatacatcac-3' (SEQ ID No:64)
b. 5'-aaggctgaatgaaagggtaattc-3' (SEQ ID No:65)

PCR Conditions

After denaturation for 3 minutes at 94° C., 5 cycles of amplification are performed as follows: 20 seconds at 93° C., 1 minute at 64° C. and 8 minutes at 68° C., followed by 30 cycles of 20 seconds at 93° C., 1 minute at 60° C. and 7.5 minutes at 68° C. Final extension is then performed for 10 minutes at 68° C.

Restriction Endonuclease Fingerprinting (REF)

The open reading frame of the ATM transcript was divided into eight partly overlapping PCR fragments. Each fragment spans 1.0–1.6 kb and is defined by two PCR primers as follows.

REF1.
a. 5'-caccctgctgcccagatatg-3' (SEQ ID No:66)
b. 5'-cttataccacgaaaggtaatacac-3' (SEQ ID No:67)

REF2.
a. 5'-gaggtcaaacctagaaagctcac-3' (SEQ ID No:68)
b. 5'-cctctcctttgttagatgcc-3' (SEQ ID No:69)

REF3.
a. 5'-ctaggtcaaagcaatatggactc-3' (SEQ ID No:70)
b. 5'-catgcgatggaaaatgaggtg-3' (SEQ ID No:71)

REF4.
a. 5'-cagagattgtggtggagttattg-3' (SEQ ID No:72)
b. 5'-gcattatgaaggtccactgaag-3' (SEQ ID No:73)

REF5.
a. 5'-cttcagtggaccttcataatgc-3' (SEQ ID No:74)
b. 5'-ccatacaaactatctggctcc-3' (SEQ ID No:75)

REF6.
a. 5'-ctggaataagtttacaggatcttc-3' (SEQ ID No:76)
b. 5'-gatgatttcatgtagtttcaattc-3' (SEQ ID N6:77)

REF7.
a. 5'-gatggagaaagtagtgatgagc-3' (SEQ ID No:78)
b. 5'-agtcaccagatttccatattctc-3' (SEQ ID No:79)

REF8.
a. 5 '-aagatgttgttgtccctactatg-3' (SEQ ID No:80)
b. 5'-aaggctgaatgaaagggtaattc-3' (SEQ ID No:81)

Patient and family resources: A cell line repository was established containing 230 patient cell lines and 143 cell lines from healthy members of Moroccan Jewish, Palestinian Arab and Druze families. Some of these pedigrees are highly inbred and unusually large (Ziv et al., 1991; Ziv, 1992). In view of the large number of meiotic events required for high-resolution linkage analysis, applicants collaborated with Dr. Carmel McConville (University of Birmingham, UK) and Dr. Richard Gatti (UCLA, Los Angeles, Calif.), who have also established extensive repositories of A-T families. Linkage analysis was conducted on a pool of 176 families.

Example 1

Definition of the A-T interval by genetic analysis: Studies based only on analysis of Israeli A-T families enabled localization of the A-T(C) gene at 11q22–23 (Ziv, 1991), and confirmed the localization of A-T(A) mutation in Palestinians to the same region (Ziv et al., 1992). Studies with the Birmingham group further narrowed the major A-T interval to 4 centimorgans, between D11S611 and D11S1897 (McConville et al., 1993), and subsequently to 3 centimorgans, between GRIA4 and D11S1897 (Ambrose et al., 1994a; McConville et al., 1994) (see also Shiloh, 1995, and FIG. 1).

All these studies were conducted with biallelic markers, whose power is limited by their low polymorphic information content (PIC). The recently discovered microsatellite markers based on variable numbers of tandem simple repeats (Litt-and Luty, 1989; Weber and May, 1989) are much more powerful due to their high degree of polymorphism. Microsatellite markers were used to saturate the A-T region using two approaches. The first, was based on physical mapping of microsatellite markers generated by others which were loosely linked to chromosome 11q.

Mapping experiments were conducted using YAC and cosmid contigs which allowed precise, high-resolution localization of DNA sequences in this region of chromosome 11. These experiments led to the localization of 12 microsatellites at the A-T region (Vanagaite et al., 1994a; Vanagaite et al., 1995).

The second approach was based on generating new microsatellites within the YAC contig. A rapid method for the identification of polymorphic CA-repeats in YAC clones was set up (Rotman, 1995) resulting in the generation of twelve new markers within the A-T locus (Vanagaite et al., 1995; Rotman et al., 1995; Rotman et al., 1994b). Hence, the high-density microsatellite map constructed in this manner contained a total of 24 new microsatellite markers and spans the A-T locus and flanking sequences, over a total of six megabases (Vanagaite et al., 1995).

Figure 1:
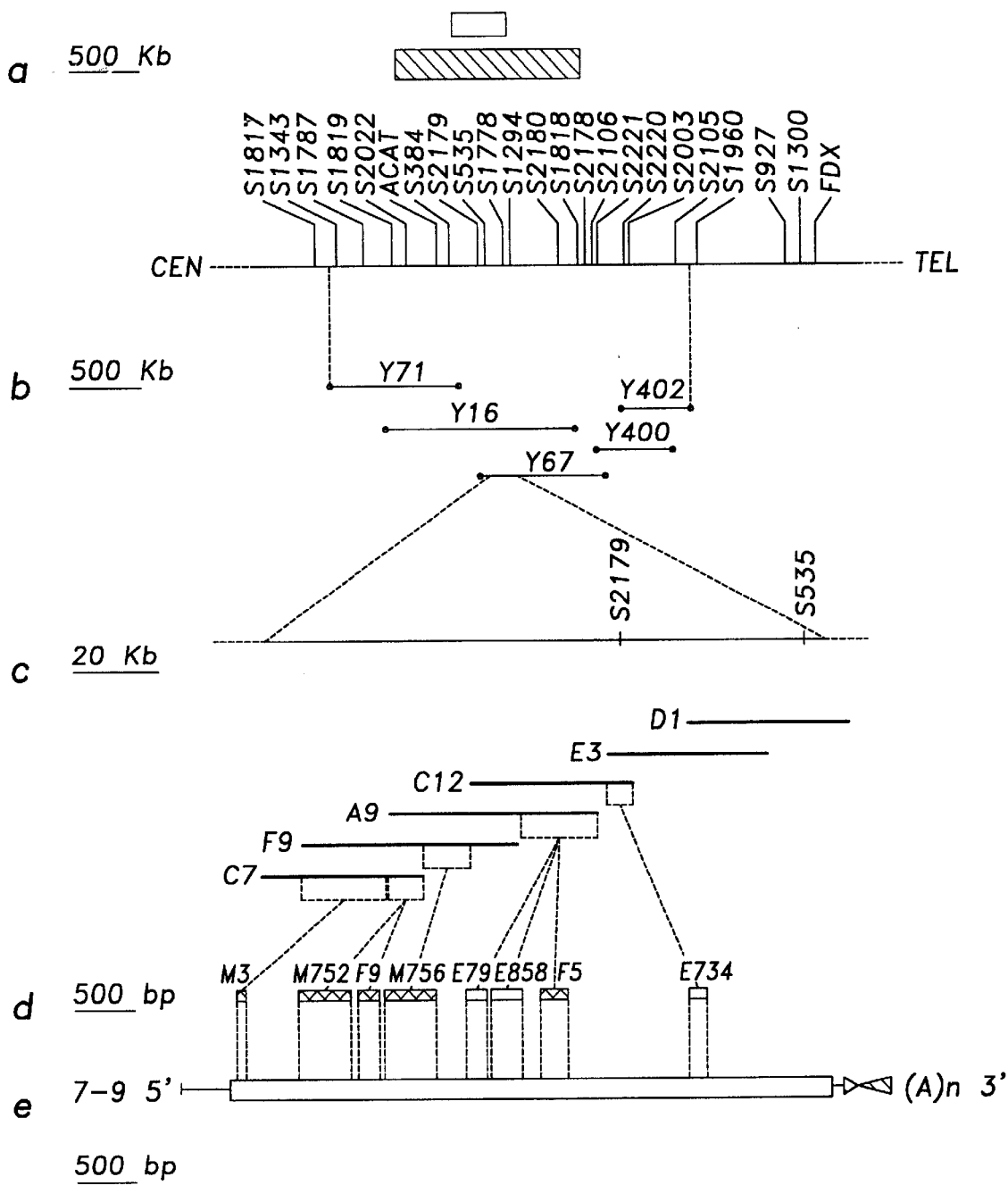

Repeated linkage analysis on the entire cohort of A-T families indicated that the A-T(A) locus was definitely located within a 1.5 megabase region between D1S1819 and D11S1818 (Gatti et al., 1994) as shown in FIG. 1 and in Shiloh (1995), with a clear peak of the cumulative lod score under D11S535 (Lange et al., 1994).

Concomitant with these studies, linkage disequilibrium (LD) analysis of Moroccan-Jewish A-T patients was conducted. LD refers to the non-random association between alleles at two or more polymorphic loci (Chakravarti et al., 1984). LD between disease loci and linked markers is a useful tool for the fine localization of disease genes (Chakravarti et al., 1984; Kerem et al. 1989; Ozelius et al., 1992; Sirgo et al.:, 1992;. Hastbacka et al., 1992; Mitchison et al., 1993). LD is particularly powerful in isolated ethnic groups, where the number of different mutations at a disease locus is likely to be low (Hastbacka et al., 1992; Lehesjoki et al., 1993; Aksentijevitch et al., 1993). Early on, applicants observed very significant LD (p<0.02–p<0.001) between A-T and markers along the D11S1817–D11S927 region in the patients of the sixteen Moroccan-Jewish A-T families identified in Israel (Oskato et al., 1993). Further analysis with the new markers narrowed the peak of linkage disequilibrium to the D11S384–D11S1818 region as shown in FIG. 1.

Haplotype analysis indicated that all of the mutant chromosomes carry the same D11S384–D11S1818 haplotype, suggesting a founder effect for A-T in this community, with one mutation predominating.

Example 2

Sequencing the ATM Gene

Cloning the disease locus in a contig (set of overlapping clones) was essential in isolating the A-T disease gene. The entire A-T locus and flanking region in a contig of yeast artificial chromosomes (YACs) was cloned by methods well known in the art (Rotman et al. 1994c; Rotman et al., 1994d). This contig was instrumental in the construction of the microsatellite map of the region (Vanagaite et al., 1995) and subsequently enabled construction of cosmid contigs extending over most of the interval D11S384–D11S1818. Cosmids corresponding to the YAC clones were identified in a chromosome 11-specific cosmid library supplied by Dr. L. Deaven (Los Alamos National Laboratory) and were ordered into contigs by identifying overlaps as shown in FIG. 1.

Isolation of the A-T gene: Transcribed sequences were systematically identified based on two complementary methods:

1. Use of an improved direct selection method based on magnetic bead capture (MBC) of cDNAs corresponding to genomic clones (Morgan et al., 1992; Tagle et al., 1993). In several, large-scale experiments YAC or cosmid DNA was biotinylated and hybridized to PCR-amplified cDNA from thymus, brain and placenta. Genomic DNA-cDNA complexes were captured using streptavidin-coated magnetic beads which was followed with subsequent elution, amplification, and cloning of captured cDNAs. The cDNA inserts were excised from a gel, self-ligated to form concatamers and sonicated to obtain random fragments. These fragments were size fractionated by gel electrophoresis, and the 1.0–1.5 Kb fraction-was extracted from the gel and subcloned in a plasmid vector. The end portions of individual clones were sequenced using vector-specific primers, in an automated sequencer (Model 373A, Applied Biosystems), and the sequences were aligned using the AutoAssembler program (Applied Biosystems Division, Perkin-Elmer Corporation). In the final sequence each nucleotide position represents at least 3 independent overlapping readings.

YACs were also used and were no less efficient than cosmids as starting material for MBC, with more than 50% of the products mapping back to the genomic clones. However, when a small panel of radiation hybrids spanning the A-T region was used to test the cDNA fragments, it was found that some clones that hybridized back to the YACs and cosmids were not derived from this region. This pitfall probably stems from limited homology between certain portions of different genes, and points up the necessity to use radiation hybrid mapping when testing the authenticity of the captured sequences, and not to rely solely on cloned DNA for this purpose.

Homology searches in sequence databases showed that only one of the first 105 cDNA fragments mapped to the A-T region was homologous to a sequence previously deposited in one of the databases, as an expressed sequence tag (EST).

2. Exon amplification, also termed "exon trapping" (Duyk et al., 1990; Buckler et al., 1991), is based on cloning genomic fragments into a vector in which exon splice sites are flagged by splicing to their counterpart sites in the vector. This method of gene identification was expected to complement the MBC strategy, since it does not depend on the constitution of cDNA libraries or on the relative abundance of transcripts, and is not affected by the presence of repetitive sequences in the genomic clones. An improved version of this system (Church et al., 1993) that eliminated problems identified in an earlier version, including a high percentage of false positives and the effect of cryptic splice sites was utilized. Each experiment ran a pool of three to five cosmids with an average of two to five exons identified per cosmid. A total of forty five exons were identified.

Sequence analysis and physical mapping indicated that MBC and exon amplification were complementary in identifying transcribed sequences.

The availability of a deep cosmid contig enabled rapid and precise physical localization of the cDNA fragments and captured exons, leading to a detailed transcriptional map of the A-T region.

Both MBC and exon amplification yielded short (100–1000 bp) transcribed sequences. Those sequences were used as anchor points in isolating full-length clones from twenty eight cDNA libraries currently at applicants disposal and which represented a variety of tissues and cell lines.

Initial screening of the cDNA libraries by polymerase chain reaction (PCR) using primer sets derived from individual cDNA fragments or exons aided in the identification of the libraries most likely to yield corresponding cDNA clones.

Large scale screening experiments were carried out in which most of the cDNA fragments and exons were used in large pools. In addition to the mass screening by hybridization, PCR-based screening methods and RACE (rapid amplification of cDNA ends) (Frohman et al., 1988; Frohman et al., 1994) was employed to identify full-length cDNAs.

The above experiments resulted in the initial, identification and isolation of a cDNA clone designated 7-9 (Savitsky et al, 1995a), the complete sequence of which is set forth in SEQ ID No:1 and which is derived from a gene located under the peak of cumulative location score obtained by linkage analysis as shown in FIG. 1. The gene extends over some 300 kilobases (kb) of genomic DNA and codes for two major mRNA species of 12 kb and 10.5 kb in length. The 7-9 clone is 5.9 kb in length and, therefore, is not a full length clone.

An open reading frame of 5124 bp within this cDNA encodes a protein with signature motifs typical of a group of signal transduction proteins known as phosphatidylinositol 3-kinases (PI 3-kinases). PI 3-kinases take part in the complex system responsible for transmitting signals from the outer environment of a cell into the cell. It is not clear yet whether the protein product of the corresponding gene encodes a lipid kinase or a protein kinase.

The gene encoding the 7-9 cDNA clone was considered a strong A-T candidate and mutations were sought in patients. Southern blotting analysis revealed a homozygous deletion in this gene in affected members of Family N., an extended Palestinian Arab A-T family which has not been assigned to a specific complementation group. All the patients in this family are expected to be homozygous by descent for a single A-T mutation. The deletion includes almost the entire genomic region spanned by transcript 7-9, and was found to segregate in the family together with the disease. This finding led to a systematic search for mutations in the 7-9 transcript in additional patients, especially those previously assigned to specific complementation groups.

The restriction endonuclease fingerprinting (REF) method (Liu and Sommer 1995) was applied to reverse-transcribed and PCR-amplified RNA (RT-PCR) from A-T cell lines. Observation of abnormal REF patterns was followed by direct sequencing of the relevant portion of the transcript and repeated analysis of another independent RT product. In compound heterozygotes, the two alleles were separated by subcloning of RT-PCR products and individually sequenced. Genomic sequencing was conducted in some cases to confirm the sequence alteration at the genomic level. Additional family members were studied when available.

Initially, ten sequence alterations (Table 2) were identified in the 7-9 transcript in 13 A-T patients including two sibling pairs. Most of these sequence changes are expected to lead to premature truncation of the protein product, while the rest are expected to create in-frame deletions of 1–3 amino acid residues in this protein. While the consequences of the in-frame deletions remain to be investigated, it is reasonable to assume that they result in impairment of protein function. In one patient, AT3NG, the loss of a serine residue at position 1512 occurs within the PI3-kinase signature sequence. This well conserved domain is distantly related to the catalytic site of protein kinases, hence this mutation is likely to functionally affect the 7-9 protein.

In view of the strong evidence that mutations in this gene are responsible for A-T, it was designated ATM (A-T, Mutated). Since these patients represent all complementation groups of the disease and considerable ethnic variability, these results indicate that the ATM gene alone is responsible for all A-T cases.

In order to complete the cloning of the entire ATM open reading frame, fetal brain and colon random-primed libraries obtained from Stratagene (San Diego, Calif.) and an endothelial cell random-primed library (a gift of Dr. David Ginsburg, University of Michigan) were screened. A total of $1\times10^6$ pfu were screened at a density of 40,000 pfu per 140 mm plate, and replicas were made on Qiabrane filters (Qiagen), as recommended by the manufacturer. Filters were prehybridized in a solution containing 6×SSC, 5×Denhardt's, 1% N-laurylsarcosyl, 10% dextran sulfate and 100 µg/ml salmon sperm DNA for 2 hours at 65° C. Hybridization was performed for 16 hrs under the same conditions with $1\times10^6$ cpm/ml of $^{32}$P-labelled probe, followed by final washes of 30 minutes in 0.25×SSC, 0.1% SDS at 60° C. Positive clones were plaque-purified using standard techniques and sequenced. DNA sequencing was performed using an automated DNA sequencer (Applied Biosystems, model 373A), and the sequence was assembled using the AutoAssembler program (Applied Biosystems Division, Perkin-Elmer Corporation). In the final sequence, each nucleotide represents at least four independent readings in both directions.

Database searches for sequence similarities were performed using the BLAST network service. Alignment of protein sequences and pairwise comparisons were done using the MACAW program, and the PILEUP and BESTFIT programs in the sequence analysis software package developed by the Genetics Computer Group at the University of Wisconsin.

Example 3

Detection of Mutations

Determination of mutations: The recently discovered ATM gene is probably involved in a novel signal transduction system that links DNA damage surveillance to cell cycle control. A-T mutations affect a variety of tissues and lead to cancer predisposition. This striking phenotype together with the existence of "partial A-T phenotypes" endow the study of ATM mutations with special significance.

Materials and Methods

RT-PCR: Total RNA was extracted from cultured fibroblast or lymphoblast cells using the Tri-Reagent system (Molecular research Center, Cincinnati, Ohio). Reverse transcription was performed on 2.5 ug of total RNA in a final volume of 10 ul, using the Superscript II Reverse Transcriptase (Gibco BRL, Gaithersburg, Md.) in the buffer recommended by the supplier, and in the presence of 125 U/ml of RNAsin. (Promega) and 1 mM dNTPs (Pharmacia). Primers were either oligo(dT) (Pharmacia) or a specifically designed primer. The reaction products were used as templates for PCR performed with specific primers. These reactions were carried out in 50 µl containing 2 units of Taq DNA Polymerase (Boehringer Mannheim, Mannheim, Germany), 200 µm dNTPs, 0.5 µM of each primer, and one tenth of the RT-PCR products. The products were purified using the QIA-quick spin system (Qiagen, Hilden, Germany).

Restriction endonuclease fingerprinting: The protocol of Liu and Sommer (1995) was followed with slight modifications. RT-PCR was performed as described above, using primers defining PCR products of 1.0–1.6 kb. One hundred ng of amplified DNA was digested separately with 5 or 6 restriction endonucleases in the presence of 0.2 units of shrimp alkaline phosphatase (United States Biochemicals, Cleveland, Ohio). Following heat inactivation at 65° C. for 10 minutes, the digestion products corresponding to the same PCR product were pooled, denatured at 96° C. for 5 minutes and immediately chilled on ice. Ten ng of this fragment mixture was labeled in the presence of 6 $\mu$Ci of [$\gamma$-$^{33}$P]ATP and 1 unit of T4 polynucleotide kinase (New England Biolabs, Beverly, Mass.) at 37° C. for 45 minutes. Twenty $\mu$l of stop solution containing 95% formamide, 20 mM EDTA, 0.05% bromophenol blue, 0.05% xylene cyanol, and 10 mM NaOH were added, and the samples were boiled for 3 minutes and quick-chilled on ice. Electrophoresis was performed in 5.6% polyacrylamide gels in 50 mM Tris-borate, pH 8.3, 1 mM EDTA at constant power of 12 W for 3 hours at room temperature, with a fan directed to the glass plates, keeping them at 22–24° C. The gels were dried and subjected to autoradiography.

Direct sequencing of PCR products: Five hundred ng of PCR products was dried under vacuum, resuspended in reaction buffer containing the sequencing primer, and the mixture was boiled and snap-frozen in liquid nitrogen. The Sequenase II system (Unites States Biochemicals) was used to carry out the sequencing reaction in the presence of 0.5 $\mu$g of single-strand binding protein (T4 gene 3.2 protein, United States Biochemicals). The reaction products were treated with 0.1 $\mu$g of proteinase K at 65° C. for 15 minutes, separated on a 6% polyacrylamide gel, and visualized by autoradiography.

Using the methods described herein above the ATM transcript was scanned for mutations in fibroblast and lymphoblast cell lines derived from an extended series of A-T patients from 13 countries, all of whom were characterized by the classical A-T phenotype. The analysis was based on RT-PCR followed by restriction endonuclease fingerprinting (REF). REF is a modification of the single-strand conformation polymoprphism (SSCP) method, and enables efficient detection of sequence alterations in DNA fragments up to 2 kb in length (Liu and Sommer, 1995).

Briefly, after PCR amplification of the target region, multiple restriction endonuclease digestions are performed prior to SSCP analysis, in order to increase the sensitivity of the method and enable precise localization of a sequence alteration within the analyzed fragment. The coding sequence of the ATM transcript, which spans 9168 nucleotides (SEQ ID No:2) (Savitsky et al., 1995b), was thus divided into 8 partly overlapping portions of 1.0–1.6 Kb, and each one was analyzed separately (see Example 4 also). Sequence alterations causing abnormal REF patterns were located and disclosed by direct sequencing. Mutations identified in this way were reconfirmed by repeating the RT-PCR and sequencing, or by testing the presence of the same mutations in genomic DNA.

In compound heterozygotes, the two alleles were separated by subcloning and individually sequenced. In some cases, agarose gel electrophoresis showed large deletions in the ATM transcript manifested as RT-PCR products of reduced sizes. The breakpoints of such deletions were delineated by direct sequencing of these products.

The 54 mutations identified to date in our patient cohort (Table 3, FIG. 4) include 44 new ones and 10 previously identified ones (Table 2). (Mutations in Table 3 are presehted according to the nomenclature proposed by Beaudet & Tsui (1993); nucleotide numbers refer to their positions in the sequence of the ATM transcript (accession number U33841); the first nucleotide of the open reading frame was designated +1.) These mutations were found amongst 65 A-T families: many are unique to a single family, while others are shared by several families, most notably the 4 nt deletion, 7517del4, which is common to 6 A-T families from South-Central Italy (Table 3). According to this sample, there is a considerable heterogeneity of mutations in A-T, and most of them are "private". The proportion of homozygotes in this sample is relatively high due to a high degree of consanguinity the populations studied. It should be noted, however, that apparently homozygous patients from non-consanguineous families may in fact be compound heterozygotes with one allele not expressed.

This series of 54 A-T mutations is dominated by deletions and insertions. The smaller ones, of less than 12 nt, reflect identical sequence alterations in genomic DNA. Deletions spanning larger segments of the ATM transcript were found to reflect exon skipping, not corresponding genomic deletions. This phenomenon usually results from sequence alterations at splice junctions or within introns, or mutations within the skipped exons, mainly of the nonsense type (Cooper and Krawczak, 1993; Sommer, 1995; Steingrimsdottir et al., 1992; Gibson et al., 1993; Dietz and Kendzior, 1994). One large deletion spans about 7.5 Kb of the transcript and represents a genomic deletion of about 85 Kb within the ATM gene. Of these deletions and insertions, 25 are expected to result in frameshifts. Together with the 5 nonsense mutations, truncation mutations account for 83% of the total number of mutations in this sample. Nine in-frame deletions span long segments (30–124 aa) of the protein, and similarly to the truncation mutations, are expected to have a severe effect on the protein's structure. It should be noted that two base substitutions abolish the translation initiation and termination codons. The latter is expected to result in an extension of the ATM protein by an additional 29 amino acids. This mutation may affect the conformation of the nearby PI 3-kinase-like domain.

While the effect of the 5 small (1–3 aa) in-frame deletions and insertions on the ATM protein remains to be studied, it should be noted that one such deletion (8578del3) leads to a loss of a serine residue at position 2860. This amino acid is part of a conserved motif within the PI 3-kinase-like domain typical of the protein family to which ATM is related, and is present in 7 of 9 members of this family. The single missense mutation identified in this study, which leads to a Glu2904Gly substitution, results in a nonconservative alteration of another extremely conserved residue within this domain, which is shared by all of these proteins. The patient homozygous for this mutation, AT41RM, shows the typical clinical A-T phenotype. Measurement of radioresistant DNA synthesis in the patient's cell line revealed a typical A-T response, demonstrating that this patient has the classical A-T cellular phenotype.

As discussed herein above, the ATM gene of the present invention is probably involved in a novel signal transduction system that links DNA damage surveillance to cell cycle control. A-T mutations affect a variety of tissues and lead to cancer predisposition. This striking phenotype together with the existence of "partial A-T phenotypes" endow the study of ATM mutations with special significance.

The ATM gene leaves a:great deal of room for mutations: it encodes a large transcript. The variety of mutations identified in this study indeed indicates a rich mutation repertoire. Despite this wealth of mutations, their structural characteristics point to a definite bias towards those that inactivate or eliminate the ATM protein The nature or distribution of the genomic deletions among these mutations do not suggest a special preponderance of the ATM gene for such mutations, such as that of the dystrophin (Anderson and Kunkel, 1992) or steroid sulfatase (Ballabio et al., 1989) genes which are particularly prone to such deletions. Thus, one would have expected also a strong representation of missense mutations, which usually constitute a significant portion of the molecular lesions in many disease genes (Cooper and Krawczak, 1993; Sommer, 1995). However, only two such mutations were identified in the present study. Other point mutations reflected in this series are those that probably underlie the exon skipping deletions observed in many patients, again, exerting a severe structural effect on the ATM protein.

A technical explanation for this bias towards deletions and insertions could be a greater ability of the REF method to detect such lesions versus its ability to detect base substitution. Liu and Sommer (1995) have shown, however, that the detection rate of this method in a sample of 42 point mutations in the factor IX gene ranged between 88t and 100%, depending on the electrophoresis conditions. The 10 base substitutions detected directly by the REF method in the present study (Tables 2 and 3), indicate that such sequence alterations are detected in our hands as well.

Since the expected result of most of these mutations is complete inactivation of the protein, this skewed mutation profile might represent a functional bias related to the studied phenotype, rather than a structural feature of the ATM gene that lends itself to a particular mutation mechanism. The classical A-T phenotype appears to be caused by homozygosity or compound heterozygosity for null alleles, and hence is probably the most severe expression of defects in the ATM gene. The plethora of missense mutations expected in the large coding region of this gene is probably rarely represented in patients with classical A-T, unless such a mutation results in complete functional inactivation of the protein. By inference, one missense identified in this study, Glu2940Gly, which substitutes a conserved amino acid at the PI 3-kinase domain and clearly gives rise to a classical A-T phenotype, points to the importance of this domain for the biological activity of the ATM protein. Mutations in this domain abolish the telomere-preserving function of the TEL1 protein in *S. cerevisiae* (Greenwell et al., 1995), a protein which shows a particularly high sequence similarity to ATM (Savitsky et al., 1995b; Zakian, 1995). Another member of the family of PI 3-kinase-related proteins that includes ATM is the mammalian FRAP. Mutations in the PI 3-kinase domain abolish its autophosphorylation ability and biological activity (Brown et al., 1995). These observations, together with the mutation shown here, suggest that this domain in ATM is also likely to include the catalytic site, which may function as a protein kinase.

Genotype-phenotype relationships associated with the ATM gene appear therefore to extend beyond classical A-T. There are several examples of genes in which different mutations lead to related but clinically different phenotypes. For example, different combinations of defective alleles of the ERCC2 gene may result in xeroderma pigmentosum (group D), Cockayne's syndrome or trichothiodystrophy—three diseases with different clinical features involving UV sensitivity (Broughton et al., 1994, 1995).

Different mutations in the CFTR gene may lead to full-fledged cystic fibrosis, or only to congenital bilateral absence of the vas deferens which is one feature of this disease (Chillon et al., 1995; Jarvi et al., 1995). A particularly interesting example is the X-linked WASP gene responsible for Wiskott Aldrich syndrome (WAS), characterized by immunodeficiency, eczema and thrombocytopenia. Most of the mutations responsible for this phenotype cause protein truncations; however, certain missense mutations may result in X-linked thrombocytopenia, which represents a partial WAS phenotype, while compound heterozygosity for a severe and mild mutation results in females in an intermediate phenotype (Kolluri et al., 1995; Derry et al., 1995).

In a similar manner, genotypic combinations of mutations with different severities create a continuous spectrum-of phenotypic variation in many metabolic diseases.

Which phenotypes are most likely to be associated with milder ATM mutations! Since cerebellar damage is the early and severe manifestation of A-T, it is reasonable to assume that the cerebellum might also be affected to some extent in phenotypes associated with milder ATM mutations. Such phenotypes may include cerebellar ataxia, either isolated (Harding, 1993) or coupled with various degrees of immunodeficiency. The latter combination has indeed been described, sometimes with chromosomal instability, and is often designated "ataxia without telangiectasia" (Ying and Decoteau, 1983; Byrne et al., 1984; Aicardi et al., 1988; Maserati, 1988; Friedman and Weitberg, 1993). Friedman and Weitberg (1993) recently suggested a new clinical category of "ataxia with immune deficiency" that would include A-T as well as other cases of cerebellar degeneration with immune deficits. Evaluation of patients with cerebellar disorders with the present invention may reveal a higher frequency of such cases than previously estimated. However, in view of the pleiotropic nature of the ATM gene, the range of phenotypes associated with various ATM genotypes may be even broader, and include mild progressive conditions not always defined as clear clinical entities. Screening for mutations in this gene in such cases may reveal wider boundaries for the molecular pathology associated with the ATM gene.

Example 4

Determination of Genomic Organization

The exon/intron boundaries and the intron sizes were determined using long-distance PCR (Barnes, 1994; Cheng et al., 1994; Foord and Rose, 1994). Primers were designed based on the ATM cDNA sequence (Savitsky et al., 1995a,b) at 200–300 bp intervals. Templates for these reactions were cosmid and YAC clones, and human genomic DNA. PCR products were obtained in all cases, including those that span the largest intron, of 11 kb. In the large majority of cases, PCR products of the same size were obtained with all templates, and those obtained from genomic DNA were used for sequencing of the exon-intron junctions. Following initial reactions, new primers were designed as needed, based on the evolving knowledge of the gene structure. Exon-intron boundaries were determined at the sites where genomic and cDNA sequences diverged. Typical splice acceptor and donor sequences were found around these sites in all cases. During the search for the A-T gene, six exons were isolated by exon trapping (Shiloh et al., 1994b) using the vectors pSPL3 (Church et al., 1994) and éGET (Nehls et al., 1994a,b). Their boundaries coincided with those obtained by long-distance PCR.

The ATM gene is composed of 66 exons (FIG. 3 and Tables 1 and 5). The first two exons are alternatively spliced, and are designated 1 a (SEQ ID No:10) and 1b (SEQ ID No:9). With the exception of the 3' exon, ATM exons (SEQ ID Nos:11–63) range in size from 64 to 372 bp, with an average of 149 bp. The introns vary considerably in size, from 100 bp to about 11 kb, with the majority in the range of 1–3 kb. The consensus dinucleotides GT and AG were found at the donor and acceptor splice sites of all introns, except for a variant donor site with a GC dinucleotide (reviewed in Jackson, 1991) present in the intron 3' to exon 51. The first methionine of the open reading frame is located in exon 3, whereas the stop codon is located in the 3' and largest exon of 3.6 kb. This exon includes a 3' untranslated region (UTR)(SEQ ID No:8) of about 3800 nucleotides.

The ATM gene contains one of the largest number of exons reported to date for a human gene. However, these exons are spread over a relatively compact genomic region of about 150 kb. The dystrophin gene, for example, consists of 79 exons spanning 2.4 Mb of genomic DNA (Roberts et al., 1993), while the Huntington's disease gene consists of 67 exons spread over 180 Kb (Ambrose et al., 1994b).

Throughout this application various publications and patents are referenced by citation or number. Full citations for the publications referenced are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

EXON-INTRON ORGANIZATION OF THE ATM GENE

| Exon No. | 5' intronic sequence | Exon First Base* | Exon length (bp) | Exon Last Base* | 3' intronic sequence | Size of 3' intron (kb) |
|---|---|---|---|---|---|---|
| 1a§ |  | -554 AGGTAG | 120 | GCAGTG -435 | gtagggcgcggaggcaacgcagcggcttc | 0.16 |
| 1b§ | ttttctattactgtgttttgtttcctcag | -434 TCCTCC | 316 | TACCAG -199 | gtacagataagacaactacagtgatgata | 1.10 |
| 2 | tatatatacctatatgtattttttttacag | -118 AGGCAT | 88 | ATGAGG -31 | gtaggatttgtatctgttagttcattatt | 2.70 |
| 3 | aaccattattattttcctttttatttcag | -30 ACAGTG | 102 | CGAAAG 72 | gtagtaaattactaaaattcaattttcct | 0.08 |
| 4 | gagttctgaattgcatttgtttctcttgaag | 73 AAAGAA | 113 | TTTTAG 185 | gtattctattcaaattatttactgtctt | 1.30 |
| 5 | atgttttcttatttgtttattttgaaatag | 186 ATTTTT | 146 | ACAGAA 331 | gtaagtgtgttataattataaataatggc | 6.30 |
| 6 | catgactaataatttttttttttttaag | 332 GACCAC | 165 | GGTTAG 496 | gtatgtttgaaggtgtgtttgaatttt | 8.10 |
| 7 | cccagttgagcttgtttgttctcacag | 497 AATTGT | 166 | TGCGAG 662 | gtaatctaatctcttttcttttgtttgtattg | 0.67 |
| 8 | aaaaattacatttttaattttttggattacag | 663 ACAAGA | 329 | AAAAAG 901 | gtataaaggaaatgttactgttttgaattt | 1.90 |
| 9 | gaaaaagtggattatttttatttacag | 902 GTGCTT | 164 | CACCAG 1065 | gtacagtaagtaggtcatgtcacattaga | 1.70 |
| 10 | ttccaaataaccctttttttttttttag | 1066 GTTTTT | 170 | GCCTTG 1235 | gtaaagtgttaccattttctcattcagtgt | 1.70 |
| 11 | ttttcacaattgtccttgttttgtttatag | 1236 GCTACA | 372 | TTCATG 1607 | gtaagttcagcatgcattatgtctgactt | 0.80 |
| 12 | ctaagtgagcttttgtttttcttgtag | 1608 TCCTGC | 195 | TCACAG 1802 | gtaattaagttcatcattagcatgctgctgtt | 0.90 |
| 13 | ttatatattaaagatctttactttcttgaag | 1803 TAATTT | 96 | AGAATG 1898 | gtatgttatctaataatgctctttatcatt | 0.90 |
| 14 | tatatttttattgtgtttactttag | 1899 TGAACA | 226 | TCTGAG 2134 | gtgagattttttaaaaagaactaagctt | 2.20 |
| 15 | gatttgcattttccttcattcacaatag | 2125 ATTACA | 126 | GCCAAC 2250 | gtaggagaattatactaataaagtttcgg | 1.20 |
| 16 | ttgcttggttcctttgttgtcttaattgcag | 2251 TCTCTA | 126 | ACCAAG 2376 | gtaagatttctctcttgttttgtctatcatat | 1.30 |
| 17 | cttgaacatcttgttctcttcctgaag | 2377 AAGAGT | 90 | AGTTTA 2466 | gtaagtatgctcctgttttgctatcatat | 8.50 |
| 18 | ttagtgttaatgagtgcttttattttag | 2467 GCATCC | 172 | CCATAG 2638 | gtaaatacatattactacttggatttct | 1.10 |
| 19 | cctgattttttcctctaccatcttag | 2639 GTGCCA | 200 | CATATG 2838 | gtagttacgttaaatgaagaagctcttgg | 2.60 |
| 20 | aagttgaactttttttttttccacag | 2839 TATCTA | 83 | ACTATC 2921 | gtaagaaattaaaacctatgttatgttca | 0.10 |
| 21 | tttaacttggaaaacttactgatttcag | 2922 CAATGT | 156 | ATTTTG 3077 | gtaggtacagtctatgtgtggtcctattt | 1.20 |
| 22 |  | 3078 GCATCT | 76 | CTTGAG 3153 | gtgagttttgcatttttagtaagatct | 0.10 |

TABLE 1-continued

EXON-INTRON ORGANIZATION OF THE ATM GENE

| Exon No. | 5' intronic sequence | Exon First Base* | | Exon length (bp) | Exon Last Base* | | 3' intronic sequence | size of 3' intron (kb) |
|---|---|---|---|---|---|---|---|---|
| 23 | tcatatttaaccacagtctttcccgtag | 3154 | GCTGAT | 131 | CAATAG | 3284 | gtaatggtcaaatattcatgaagtattg | 7.00 |
| 24 | tttcattgtttcttttcctcctgtcttag | 3285 | ATTGTT | 118 | GAAATG | 3402 | gtaatttaagtaacatgtatttgctgtta | 1.30 |
| 25 | ttacaatttttttttaaattcttttaag | 3403 | TCCCAT | 174 | AAAAAG | 3576 | gtatatggatgagtatttattagaagc | 1.50 |
| 26 | cttaacacattgacttttggtcgtgcag | 3577 | GTTTTA | 170 | CTATAG | 3746 | gtaagtttatacatgacatgtgaaattt | 1.30 |
| 27 | aacctgtatttaaatttctatttttag | 3747 | ATCTTG | 247 | AAACAG | 3993 | gtatggctcaatttttatgtactttcat | 3.00 |
| 28 | taaatatattttatttgtgccttgcag | 3994 | ATTGAT | 116 | TTTCAGG | 4109 | gtatgtacattttaaacttagagaactagc | 1.30 |
| 29 | tgactgtatttttccctaactctgttag | 4110 | GGATTT | 127 | AGCCCT | 4236 | gtaagtatacatgatgagtttaataaga | 0.52 |
| 30 | aagttttactaaatctgtttattttctag | 4237 | GATTCC | 200 | CCAAAG | 4436 | gtaaataacatatttagaccaatatataag | 3.00 |
| 31 | ttgttgttgttttttttaaatatatttag | 4437 | GCCTTC | 175 | AAACAG | 4611 | gtaattttctgactcatctcaaaatgta | 0.53 |
| 32 | tataattttttcttttttaaatatatttag | 4612 | GTATTG | 165 | TTGGAG | 4776 | gtaataaaatttcatcatctactatttt | 1.50 |
| 33 | gttaaagcaagtacatttctcttttag | 4777 | GAAATT | 133 | CTCAGG | 4909 | gtgctaatttaatgacatggctattt | 2.50 |
| 34 | ttaaactaattttaaaaattattttctag | 4910 | ATAATC | 96 | TTCTAG | 5005 | gtaaactacagtcatgcgctgcgtgacattt | 2.50 |
| 35 | ctgaaatagaatttctatatgtag | 5006 | AGGCTG | 172 | AGATTG | 5177 | gtgagtatttattgatacttatatgtaat | 2.00 |
| 36 | ctgataggcatttgaattgttttttcag | 5178 | TGTCAA | 142 | AAAAAG | 5319 | gtctcttaagtaataaatgttttattgaata | 1.00 |
| 37 | atttacattttctaatccttctcttctag | 5320 | TTTTTA | 177 | TGTGAA | 5496 | gtaagaagattaattagtctgataataatc | 1.60 |
| 38 | tattgggtggattgtgttgtatattctag | 5497 | GTGAAA | 178 | ATTCAG | 5674 | gtattctattaattttttaacatttaatact | 2.70 |
| 39 | ggactgagggagatattttgtttgtcag | 5675 | AGTCAG | 88 | AAAGAG | 5762 | gtaatgtaatgagtgttgctctacgtt | 2.00 |
| 40 | tgaatgacattatatctcattttttctag | 5763 | ACCTTC | 156 | GAAAAG | 5918 | gtaatggaattgaattttggttttaa | 2.00 |
| 41 | cattaaaagaggtgttcttgtgacaaacag | 5919 | AAGTCT | 88 | TTACAG | 6006 | gtaaatattagaggctctattattatgac | 3.30 |
| 42 | ctcaattttgtgtttccatgttttcag | 6007 | GATCTT | 89 | TACTAG | 6095 | gtaaattgcattttctaaacaacggtatag | 0.10 |
| 43 | cccaagctattttcacaatctttttctatag | 6096 | ACTACG | 103 | ATTCAG | 6198 | gtacattttttcccagattcctaaagcca | 1.20 |
| 44 | aacttaaaaacaacaataactcctgtttac | 6199 | GCCTTG | 149 | CGTCAG | 6347 | gtaagaaatttgactgatttttttttt | 2.50 |
| 45 | gtatattttttcttgactatctcacag | 6348 | CAAAGA | 105 | TGCCAG | 6452 | gtattatgaaaagcaaagtactacgtattt | 1.40 |

TABLE 1-continued

EXON-INTRON ORGANIZATION OF THE ATM GENE

| Exon No. | 5' intronic sequence | Exon First Base* | | Exon length (bp) | Exon Last Base* | | 3' intronic sequence | size of 3'intron (kb) |
|---|---|---|---|---|---|---|---|---|
| 46 | tttcagagtgtctttctttttcctcctag | 6453 | AGTAAA | 120 | CTCAAG | 6572 | gtatgtaattcgtgatgacttggtatccta | 4.00 |
| 47 | cttacatgaactctatgtcgtggcattcag | 6573 | ATCAGT | 235 | ACTCAG | 6807 | gtaaatacaatttaaaactatgtcatctta | 0.55 |
| 48 | atttattcccatatgtcatttcatttcag | 6808 | CTCCCT | 168 | GCAGCG | 6975 | gtttgtttttttattgctggattagtgt | 1.40 |
| 49 | tatattttaagatttttgccttttctatacag | 6976 | AACAAT | 114 | GAAAAG | 7089 | gtaagattttggagcaacccttaagatag | 1.30 |
| 50 | tataattaaattggttgtgttttcttgaag | 7090 | GCAGTA | 218 | AAACAG | 7307 | gtaactaggttctacaagtgacaattta | 1.00 |
| 51 | ttgtgttttacctaattattctatgcaag | 7308 | ATACAC | 208 | ATGAAG | 7515 | gcaagtgttactcagcccaatattctaccc | 1.00 |
| 52 | cttaattttgtgtcttttttttaatgtag | 7516 | AGAGAC | 114 | AATAAT | 7629 | gtaagtaaacctgaaaatcaaaccacaata | 0.32 |
| 53 | tgcataaatctaatagtctttttcttacag | 7630 | CTAATC | 159 | GATGAG | 7788 | gtattggattaaccatacgtacctttctag | 0.80 |
| 54 | tatgtaatgttttttgttttttattaatag | 7789 | GATCGA | 139 | AGAGAA | 7927 | gtatgttttttaaagaagaaacgttact | 1.00 |
| 55 | tcactaaaatctcttcattttaaatacag | 7928 | AAGGCA | 83 | ATTAAG | 8010 | gtaatttgcaattaactcttgattttttt | 1.00 |
| 56 | ctattatcaatcatgtttatactttattag | 8011 | GTGGAC | 141 | GTTAAG | 8151 | gtgagcttccctctctggctagccctt | 0.80 |
| 57 | acttgtttattcatgcttaattattctgaag | 8152 | GGCCGT | 117 | TATAAG | 8268 | gtaactattttgtacttctgttagttcacca | 7.50 |
| 58 | aagtaaaaggtattaatctgtaactccag | 8269 | GTGGTT | 150 | ATGATG | 8418 | gtgagtgacacccaaattaaaggttattg | 2.20 |
| 59 | aaaataattaatatatatctctatttaaag | 8419 | GAGGTG | 166 | CTATTG | 8584 | gtaatcttcttgtacatatagtacattgag | 1.50 |
| 60 | tttcagattgtttgttttcttttttctccag | 8585 | TTCGTT | 87 | ATCTAG | 8671 | gtaagtaataaaatctatgtatctattctt | 6.00 |
| 61 | cctcctaacttcactgtattctttactttag | 8672 | GTGTTG | 115 | CAGAAG | 8786 | gtaagtgatgatgaagtaaaggaggaaat | 1.00 |
| 62 | atccgtatttataatgtgttttgactctag | 8787 | ATGCTG | 64 | GTAGAG | 8850 | gtctcggtctttttggttgttttttttttt | 11.0 |
| 63 | tacctaaaacagatgtgctctctgtatag | 8851 | GTCCTT | 137 | TCTCAG | 8987 | gtgagcagtcatttttaagaaggtcctgttgt | 0.10 |
| 64 | tcactgaacctttgtgttttgtccttag | 8988 | TGATAT | ~3600 | | | | |

*The first nucleotide of the open reading frame was designated +1. §1a and 1b are alternatively spliced 5' non-coding exons.

TABLE 2 illustrates several mutations found in A–T patients

| Patient[1] | Ethnic/ geographic origin | Complementation group[4] | Mutation mRNA sequence change | Mutation Protein alteration | Codon[9] | Patient's genotype[10] |
|---|---|---|---|---|---|---|
| AT2RO | Arab | A | Deletion of 11 nt[5] | Frameshift, truncation | 499 | Homozygote |
| AT3NG | Dutch | A | Deletion of 3 nt | Deletion, 1 residue[8] | 1512 | Compound heterozygote |
| AT15LA | Philippine | A | Insertion, +A | Frameshift, truncation | 557 | Compound heterozygote |
| AT3LA[2] AT4LA[2] | African American | C | Deletion of 139 nt[6]/ Deletion of 298 nt[6] | Frameshift, trunction | 1196 | Compound heterozygotes |
| AT2BR | Celtic/Irish | C | Deletion, 9 nt | Deletion, 3 residues | 1198–1200 | Homozygote |
| AT1ABR AT2ABR | Australian (Irish/British) | E | Deletion, 9 nt | Deletion, 3 residues | 1198–1200 | Homozygote |
| AT5BX[2] AT6BX[2] | Indian/English | D | Deletion, 6 nt | Deletion, 2 residues | 1079–1080 | Compound heterozygotes |
| F-2079[3] | Turkish | ND | Insertion, +C[5] | Frameshift, truncation | 504 | Homozygote |
| AT29RM | Italian | ND | Deletion of 175 nt | Frameshift, truncation | 132 | Homozygote |
| AT103LO | Canadian | ND | Insertion, +A | Frameshift, truncation | 1635 | Homozygote |
| F-596[3] | Palestinian Arab | ND | Deletion[7] | Truncation | Most of ORF | Homozygote |

[1]Cell line designation.
[2]Sibling patients in both of whom the same mutation was idenitified.
[3]Patient expected to be homozygous by descent for an A–T mutation.
[4]According to the methods of Jaspers et al. (1988) ND: not determined.
[5]An identical sequence change waa observed in genomic DNA
[6]No evidence for deletion was observed in genomic DNA. In both siblings, a normal mRNA was observed in addition to the two deleted species. The two deleted mRNAs may represent abnormal splicing events caused by a splice site mutation.
[7]Reflects a genomic deletion segregating with the disease in Family N.
[8]The deleted serine residue is located within the PI3-kinase signature sequence (1507–1527 of SEQ ID No:2).
[9]Numbers refer to residue positions in SEQ ID No:2.
[10]In all the compound heterozygotes, the second mutation is still unidentified.

TABLE 3

Mutations in the ATM gene in patients with classical A–T.

| mRNA sequence change[1] | Predicted protein alteration | Codon[2] | Patient | Ethnic/ geographical origin | Genotype[11] |
|---|---|---|---|---|---|
| Truncations and exon skipping deletions: | | | | | |
| 9001delAG | Truncation | 3001 | 91RD90[9] | Turkish | Hmz |
| 8946insA | Truncation | 2983 | AT103LO | American | Hmz |
| 8307G → A | Trp → ter; truncation | 2769 | AT2SF | American | Compd Htz |
| 8283delTC | Truncation | 2762 | AT28RM | Italian | Compd Htz |
| 8269del403[3] | Truncation | 2758 | AT12RM | Italian | Hmz |
| 8269del1503 | Del, 50 aa | 2758 | F-2086 | Turkish | Compd Htz |
|  |  |  | GM9587 | American | Compd Htz |
| 8140C → T | Gln → ter, truncation | 2714 | IARC12/AT3 | French | Hmz |
| 7883del5 | Truncation | 2628 | ATF104 | Japanese | Hmz |
|  |  |  | JCRB316 | Japanese | Compd Htz |
| 7789del139/7630del298[4,5] | Truncation | 2544 | AT4LA | Carribean Black | Comp Htz |
| 7630del159[3] | Del, 53 aa | 2544 | F-2086 | Turkish | Compd Htz |
|  |  |  | AT13BER |  | Compd Htz |
| 7517del4 | Truncation | 2506 | AT43RM[10] | Italian | Hmz |
|  |  |  | AT59RM[10] | Italian | Hmz |
|  |  |  | AT22RM[10] | Italian | Hmz |
|  |  |  | AT57RM[10] | Italian | Compd Htz |
|  |  |  | AT7RM[10] | Italian | Compd Htz |
|  |  |  | AT8RM[10] | Italian | Compd Htz |
| 6573del5 | Truncation | 2192 | AT12BR | Australian | Compd Htz |
| 6348del105[3] | Del, 35 aa | 2116 | IARC15/AT4 | French | Hmz |
| 6199del149[3] | Truncation | 2067 | WG1101 | Canadian | Hmz |
| 5979del5 | Truncation | 1994 | AT5RM | Italian | Compd Htz |
| 5712insA | Truncation | 1905 | AT15LA | Philippino | Compd Htz |
| 5554insC | Truncation | 1852 | F-2079[9] | Turkish | Hmz |
| 5539del11 | Truncation | 1847 | AT2RO[9] | Arab | Hmz |
| 5320del355[6] | Truncation | 1774 | AT7RM | Italian | Compd Htz |
| 5320del7 | Truncation | 1774 | AT2SF | American | Compd Htz |
| 5178del142[3] | Truncation | 1727 | AT50RM | Italian | Compd Htz |
| 4612del165[3] | Del, 55 aa | 1538 | ATL105 | Japaneae | Hmz |

TABLE 3-continued

Mutations in the ATM gene in patients with classical A–T.

| mRNA sequence change[1] | Predicted protein alteration | Codon[2] | Patient | Ethnic/ geographical origin | Genotype[11] |
|---|---|---|---|---|---|
| 44437del175[3] | Truncation | 1480 | AT29RM | Italian | Hmz |
| 4110del127[3] | Truncation | 1371 | AT2TAN[9] | Turkish | Hmz |
| 3403del174[3] | Del, 58 aa | 1135 | F-2095 | Turkish | Compd Htz |
| 2839de183[3] | Truncation | 947 | F-2080[9] | Turkish | Hmz |
|  |  |  | AT10TAN[9] | Turkish | Hmz |
| 2467del372[3,4] | Del, 124 aa | 823 | AT6LA | English/Irish | Hmz |
| 2377del90[3] | Del, 30 aa | 793 | AT21RM[9] | Italian | Hmz |
| 22284delCT | Truncation | 762 | F-169[6] | Palestinian Arab | Hmz |
| 2125del125[3] | Truncation | 709 | F-2078[9] | Turkish | Hmz |
| 2113delT | Truncation | 705 | AT5RM | Italian | Compd Htz |
| 1563delAG[2] | Truncation | 522 | AT8LA[9] | Swiss/German | Hmz |
| 1339C → T | Arg → ter; truncation | 447 | F-2005[9] | Druze | Hmz |
| 1240C → T | Gln → ter; truncation | 414 | AT26RM | Italian | Hmz |
| 755delGT | Truncation | 252 | AT24RM | Italian | Hmz |
| 497del7514[7] | Truncation | 166 | F-596[9] | Palestinian-Arab | Hmz |
| −30del215 | Incorrect initiation | 5' UTR | F-303 | Bedouine | Hmz |
| 537C → T | Truncation | 35 | F-320 | Moroccan Jewish | Hmz |
|  |  |  | F-191 | Arab | Hmz |
|  |  |  | F-2084 | Bedouin | Hmz |
| 7240del4 | Truncation | 2414 | L-111 | Bedouin | Hmz |
| 2125del125 | Truncation | 709 | AT58RM | Italian | Hmz |
| 1407de1201 | Truncation | 469 | AT44RM | Italian | Hmz |
| 4777de1830 | Truncation | 1593 | F-2024 | Arab | Hmz |
| 9140 → T | Arg → ter; truncation | 3047 | AT35RM | Italian | Hmz |
| 3403del174 | Del, 58 aa | 1135 | AT42RM | Italian | Hmz |
|  |  |  | A(−T)2RM | Italian | Hmz |
| 4612del165 | Del, 55 aa | 1538 | AT2SLA | American | Hmz |
| In frame genomic deletions and insertions: |  |  |  |  |  |
| 8578del3 | Del, 1 aa | 2860 | AT3NG | Dutch | Compd Htz |
| 7636del9 | Del, 3 aa | 2547 | AT2BR | Celtic/Irish | Hmz |
|  |  |  | AT1ABR | Australian (Irish) | Hmz |
|  |  |  | AT1SF | American | Compd Htz |
| 7278del6[9] | Del, 2 aa | 2427 | AT5BI | Indian/English | Compd Htz |
|  |  |  | GM5823 | English | Compd Htz |
| 5319ins9 | Ins, 3 aa | 1774 | 251075-008T | Finnish | Compd Htz |
| 5435de13 | Del, 1 aa | 1812 | AT53RM | Italian | Hmz |
| Other base subutitutions: |  |  |  |  |  |
| 9170G → C | ter → Ser Extension of protein by 29 amino acids | ter | F-2089[9] | Turkish | Hmz |
| 8711A → G | Glu2904Gly | 2904 | AT41RM | Italian | Hmz |
| 2T → C | Met → Thr Initiation codon abolished | 1 | AT8BI | British | Compd Htz |
| 129T → C | Leu → Pro | 43 | AT51RM | Italian | Comp Htz |

[1]Presented according to the nomenclature proposed by Beaudet & Tsui (1993). Nucleotide numbers refer to their positions in the sequence of the ATM transcript (accession number U33841). The first nucleotide of the open reading frame was designated +1.
[2]Three adjacent exons skipped.
[3]One exon skipped.
[4]This allele produces two transcripts, with one or two ajacent exons skipped.
[5]The same mutation was found in two affected siblings.
[6]Two exons skipped.
[7]This transcript is produced by an allele containing a large genomic deletion spanning approximately 85 Kb within the ATM gene in Family ISAT 9 (Savitsky, et al., 1995a).
[8]For deletions, the number of the first codon on the amino terminus side is indicated. Codon numbers are according to the ATM protein sequence published by Savitsky et al. (1995b). In each section of the table, the mutations are ordered according to the codon numbers in this column, beginning with the one closest to the carboxyl terminus.
[9]Consanguineous family.
[10]All patients are from the same region.
[11]Genotypic combinations in which the mutation was found. Hmz: homozygote; Compd Htz: compound heterozygote. Each patient represents one family.

TABLE 4

Comparison of the ATM protein to related proteins in different species

| Protein | Size (aa) | Species | % identity/similarity Carboxy terminus* | Rest of protein** |
|---------|-----------|---------|------------------|-------------------|
| TEL1 | 2789 | S.cerevisiae | 45/67 | 19/44 |
| MEC1 | 2368 | S.cerevisiae | 37/63 | 20/46 |
| rad3 | 2386 | S.pombe | 38/59 | 21/46 |
| MEI-41 | 2356 | D.melanogaster | 37/59 | 22/47 |
| TOR1 | 2470 | S.cerevisiae | 33/58 | 19/45 |
| TOR2 | 2473 | S.cerevisiae | 35/60 | 20/45 |
| mTOR | 2549 | R.norvegicus | 32/59 | 13/44 |
| DNA-PK$_{cs}$ | 4096 | H.sapiens | 28/51 | 18/43 |

*350 aa of the carboxy terminus, containing the PI-3 kinase-like domain.
**The entire protein excluding the carboxy terminal 350 aa. An average value is given, since the values obtained for different parts of the proteins vary only by 1–3%.

TABLE 5

GENOMIC ORGANIZATION
Each exon and its flanking intron sequences are listed separately with the exon underlined. Exons are separated by a row of ****. Example primers are in bold.

```
                Exon 3                                (SEQ ID No:11)
  1 AGGCATACAT CACAATTTGG AATTATGCAT TGGTTTATCA ATTTACTTGT

51 TTATTGTCAC CCTGCTGCCC AGATATGACT TCATGAGGGT AGGATTTGTA

101 TCTGTTTAGT TCATTATTTG TCTAGCTATA AGTAGTAAAT ATTGTTTGCA

151 ACTATCAGTG AATGAGCATC TTCTGTTTAT GTAGATAATA CTGAACTG

****************************************************************

Exons 4–5                             (SEQ ID No:12)
  1 TTACAGCATT ACTTGTATAG ATTTTAAGGA GATCTCATTT TAAATACGGA

51  AATGTTAAGA AAAATTATTG TGCCTTTGAC CAGAATGTGC CTCTAATTGT

101 ACAGATAAAT CTAACTATAA ATGCTGCAGT ATAAAATAAT TACATACACA

151 TTTTTTCACA CCTCTTTCTC TCTATATATG CATATATACA TACACATATA

201 TATACCTATA TGTATTTTTT TTACAGACAG TGATGTGTGT TCTGAAATTG

251 TGAACCATGA GTCTAGTACT TAATGATCTG CTTATCTGCT GCCGTCAACT

301 AGAACATGAT AGAGCTACAG AACGAAAGGT AGTAAATTAC TTAAATTCAA

351 TTTTTCCTTG AAATGTGTGA TTAGTAACCC ATTATTATTT CCTTTTTATT

401 TTCAGAAAGA AGTTGAGAAA TTTAAGCGCC TGATTCGAGA TCCTGAAACA

451 ATTAAACATC TAGATCGGCA TTCAGATTCC AAACAAGGAA AATATTTGAA

501 TTGGGATGCT GTTTTTAGGT ATTCTATTCA AATTTATTTT ACTGTCTTTA

551 TTTTTCTCTT TCATATTTAT TTCTGTTGTG ATATTACTTT TGTGTGTAAG

601 TCTTAACATT TATCTTTGAT TCCTATATAT CATTATGCCT TGCATATGAA

651 TTTGGCATTT AATATTTATC CAAAACATAA TTTTTAAAGG TTGTTCATAT

701 AGAAACTTAA AAATTATAAA TTATTTCTTC AATAAAATGT TTTAGACATA

****************************************************************

Exon 6                                (SEQ ID No:13)
351 GCAGTAAAGC AATAGAAAGT CATAGAAGAT TAAGAGCTTT GCAGACCAGA
```

TABLE 5-continued

GENOMIC ORGANIZATION
Each exon and its flanking intron sequences are listed
separately with the exon underlined. Exons are separated by a
row of ****. Example primers are in bold.

```
401 TATTAAATTG GTCTTGTAGG AGTTAGGCCT TGAAAGAGAG ATTTAATTGT

451 TTTATTTGTT TTTTTCAGCT GATGTAGTAA TCTAAGCAAG GTGGTTTAAA

501 AGTTGCTCTT TGTGATGGCA TGAACAGCTT TTGAAATTAT TATAATTTAA

551 GTATTCAACG AGTTTCTGAA ATTGCATTTT GTTTTCTTGA AGATTTTTAC

601 AGAAATATAT TCAGAAAGAA ACAGAATGTC TGAGAATAGC AAAACCAAAT

651 GTATCAGCCT CAACACAAGC CTCCAGGCAG AAAAAGATGC AGGAAATCAG

701 TAGTTTGGTC AAATACTTCA TCAAATGTGC AAACAGAA
```

****************************************************************

Exon 7                    (SEQ ID No:14)
```
  1 GAGCACCTAG GCTAAAATGT CAAGAACTCT TAAATTATAT CATGGATACA

51 GTGAAAGATT CATCTAATGG TGCTATTTAC GGAGCTGATT GTAGCAACAT

101 ACTACTCAAA GACATTCTTT CTGTGAGAAA ATACTGGTGT GAAATATCTC

151 AGCAACAGTG GTTAGGTATG TTTTGAAGGT TGTTGTTTGT GAATTTTTCC

201 TCATGAAATG AAACTTCACC AAAGAAAGCA CTCTGTCTGT ATCTGTCTAT

251 ATCCCCCAAG TGACCTGACA GGTTAACAG TACTTTAGTA AAATTATATG

301 GTTATCGAAC TGACCCTTAA TTTTTATTTA TTATGTAGCT TTTGAATAA
```

****************************************************************

Exon 8                    (SEQ ID No:15)
```
  1 AATTGTTCTC TGTGTACTTC AGGCTCTATC TGAAACCTTC ACAAGATGTT

51 CATAGAGTTT TAGTGGCTAG AATAATTCAT GCTGTTACCA AAGGATGCTG

101 TTCTCAGACT GACGGATTAA ATTCCAAATT TTTGGACTTT TTTTCCAAGG

151 CTATTCAGTG TGCGAGGTAA TCTAATCTCT TTTTCTTTGT TTTGTATTGA

201 AATACTTTTG ATCTTGCAAG ACCATGTTTT AGACTCAGTA ACTAAAAATT

251 CTACCTTAAA ATAAAACATT GATCCATCAT AACAGAACTA GTGGATTCCT

301 AAAGAGACAA CCAAGTCCAA CACTTTCTGA ATATCCAATA TGCAGAACAC

351 TACGTGAAGT TTTCAAGGGG GAGATGTGTC TTGCTGAT
```

****************************************************************

Exon 9                    (SEQ ID No:16)
```
  1 ACAGAGTGGT CTCTTACACC AAATAAGAAC TAATTTTTTG TCAGTGTGAA

51 GTAATGCTGT GATTTTTTTT TTAATGAATA GTTTTGAAAT TAAGACTACT

101 GTTTGAAAAT TAGGGTTTTG TTTTTTTTTC TTTCAGCATA CCACTTCATA

151 ACTGTTCAGT TTGTACAGTT TGTTCCCCCT GTTATACCCA GTTGAGCTTG

201 TTTGTTTCTT CACAGACAAG AAAAGAGCTC TTCAGGTCTA AATCATATCT

251 TAGCAGCTCT TACTATCTTC CTCAAGACTT TGGCTGTCAA CTTTCGAATT

301 CGAGTGTGTG AATTAGGAGA TGAAATTCTT CCCACTTTGC TTTATATTTG

351 GACTCAACAT AGGCTTAATG ATTCTTTAAA AGAAGTCATT ATTGAATTAT

401 TTCAACTGCA AATTTATATC CATCATCCGA AGGAGCCAA AACCCAAGAA

451 AAAGGTATAA AGGAAATGTT TACTGTTTTG AATTTGCTTC TTCATTCAAA

501 CATAGAAGTC TAAGTATAAA ATTAGTGTTC TTTAGGAGGA TATGACTTTC
```

TABLE 5-continued

GENOMIC ORGANIZATION
Each exon and its flanking intron sequences are listed
separately with the exon underlined. Exons are separated by a
row of ****. Example primers are in bold.

```
551 CTCTGGATTT CTCTGGTTGA TAATGTTACT TAGCCATGAG AATGTTTTTC

601 ATAGAGTTTT T
```

****************************************************************

```
                    Exon 10                          (SEQ ID No:17)
  1 GTGCTTATGA ATCAACAAAA TGGAGAAGTA TTTTATACAA CTTATATGAT

51 CTGCTAGTGA ATGAGATAAG TCATATAGGA AGTAGAGGAA AGTATTCTTC

101 AGGATTTCGT AATATTGCCG TCAAAGAAAA TTTGATTGAA TTGATGGCAG

151 ATATCTGTCA CCAGGTACAG TAAGTAGGTC ATGTCACATT TAGAAATTTC

201 CTGTTAATTT TTTTTTTAAA CTGGGCATTT GGGCTTTTAA AACCTGTGTT

251 CTCACAAAAA GCCTATAAAA TGACTCTGTA CATGCAACTA TTCCTTTCAA

301 ACTATCAGAA ATATTTGGAA TTACCCTTTT AACTTAAAAG TTAATGCTTT

351 TGCAGATATT TGAAAACTAA CAATGAACTT TTTCATTCTT AAATGATTGT

401 CTCTAGGAAA TAAGGTGACC CTAACCCTAA TGATTCGATT CGACTCGA
```

****************************************************************

```
                    Exon 11                          (SEQ ID No:18)
  1 GGTTGTGGTT ATACGAGATC GTGCTGTTCC ACTCCAACCT GGGCAACAAC

51 AGCGAAATCT GGCTCAAAAA AAAAAAAAAA GAAAAAAGTG GATTTATTTT

101 TATTTTACAG GTTTTTAATG AAGATACCAG ATCCTTGGAG ATTTCTCAAT

151 CTTACACTAC TACACAAAGA GAATCTAGTG ATTACAGTGT CCCTTGCAAA

201 AGGAAGAAAA TAGAACTAGG CTGGGAAGTA ATAAAAGATC ACCTTCAGAA

251 GTCACAGAAT GATTTTGATC TTGTGCCTTG GTAAAGTGTT ACCATTTTCT

301 CATTCAGTGT CATTTTAATC TCTTGTATGT TATTTTTCAG AAAACTTTCA

351 GTGGAATCCT TTCATCTCAA CCAGAACTAA GTCATTTGTC TACCCCCAAA

401 CCTATTACTA GCAAAGGGAT ATGTGATTGC CATGACAAAT GAGATCAATC

451 ATTAATGGCT CATTTGCTTG GGCCAAGTGC AGGGCCACCT ATTTTAATCA
```

****************************************************************

```
                    Exon 12                          (SEQ ID No:19)
  1 AACTATTAAC AGCCAGTTTA TTTTTAGAGT ACTATGGAAA TGATGGTGAT

51 TTCTAATTAG GATATTGTAA GAGTACCATG TCTATATATT TCCTTTTAGT

101 TTGTTAATGT GATGGAATAG TTTTCAAATA TCCTTTTTTT TTTTTTTTA

151 GGCTACAGAT TGCAACCCAA TTAATATCAA AGTATCCTGC AAGTTTACCT

201 AACTGTGAGC TGTCTCCATT ACTGATGATA CTATCTCAGC TTCTACCCCA

251 ACAGCGACAT GGGGAACGTA CACCATATGT GTTACGATGC CTTACGGAAG

301 TTGCATTGTG TCAAGACAAG AGGTCAAACC TAGAAAGCTC ACAAAAGTCA

351 GATTATTAA AACTCTGGAA TAAAATTTGG TGTATTACCT TTCGTGGTAT

401 AAGTTCTGAG CAAATACAAG CTGAAAACTT TGGCTTACTT GGAGCCATAA

451 TTCAGGGTAG TTTAGTTGAG GTTGACAGAG AATTCTGGAA GTTATTTACT

501 GGGTCAGCCT GCAGACCTTC ATGGTAAGTT CAGCATGCAT TATGTCTGAC
```

TABLE 5-continued

GENOMIC ORGANIZATION
Each exon and its flanking intron sequences are listed
separately with the exon underlined. Exons are separated by a
row of ****. Example primers are in bold.

```
551 TTACAGATAA ACACACACAG ACACACACAC ACTCACATAT CCCTGATCAT

601 TTCCATAGTT TGTTACTTCA GTTAAAGATG TCAAATTCTA TTTCAGATGC

651 TTTTCTTGTT TGGCCGAGAA GACTTAATAA ATGCATAAGT GAATTTAGTT

701 TCAAATGTTG ACAAATTATT AAAGACTAAT GTTAAGGAAT TTCTTTTT

*************************************************************

Exon 13                    (SEQ ID No:20)
  1 AGAATTATGA AGAGTTTAAA TTTCTTTTAT GTGCAATTTA TCATTATTTA

51 TTAAATAGCC ATGTTAAAT TGTAGTACTA TGCACTGTTA ATAAACGAGC

101 TATTTTTTAA TCAAGAATCT TCCCAAATGT AATCAGACTT TTAACAGTTT

151 TTATGTTCAT TTAGTCACCT TAACTAAATG TATGTGCCAG GCACTGTCCT

201 GATAGATAAA GTCTTTGCCC CTCCAATAGC TTGCTTTTCA CAATTGTCCT

251 TTGTTTTGTT ATAGTCCTGC AGTATGCTGT TGACTTTGG CACTGACCAC

301 CAGTATAGTT CCAGGAACGG TAAAAATGGG AATAGAGCAA AATATGTGTG

351 AAGTAAATAG AAGCTTTTCT TTAAAGGAAT CAATAATGAA ATGGCTCTTA

401 TTCTATCAGT TAGAGGGTGA CTTAGAAAAT AGCACAGAAG TGCCTCCAAT

451 TCTTCACAGG TAATTTAAGT TCATTAGCAT GCTGCTGTTT TTTTTGTTTG

501 TTTTATCAGG CTCTCTCCAC TTATTTGATG CCAGATGGCT TTATTTTATA

551 ATAATAATGC AGAATTTCCC AGATCTAACC TTAATTATTA AATATTATGT

601 TTGTTTTTAC AGtTATCTGT GTCTTTATGC CTGATTGCTT CTGAAATAAA

651 GGGTTGTCTC ACTGTGAGAA TATGGGGGAT GTGCATGAAA AATGCACAT

*************************************************************

Exon 14                    (SEQ ID No:21)
  1 TGGATCCAAT TAAAGTACTT TTGCTTTAAT TTTACAACCT TTTATTTATT

51 TCAGAAATAA TGTTAAACAT GCTGTTTCTA AACAGTATTG GAAATGATAA

101 TAACAATGGT TGTCCTCCTT AAATTGTCCT TTTAGATATT AAGAAATTTA

151 GTATAGATGA AAGCAATTTT AATCTAGGAT CCAAATTTTA GAAGTCAAGA

201 TTTATAGCTA AACATGGATG TTAAAGTTTA AAGTATTCTT TACATGGCTT

251 TTGGTCTTCT AAGTGAAGCT TTTTGTTTTT CTTTGTAGTA ATTTTCCTCA

301 TCTTGTACTG GAGAAAATTC TTGTGAGTCT CACTATGAAA AACTGTAAAG

351 CTGCAATGAA TTTTTTCCAA AGCGTGCCAG AATGGTATGT TATCTAATAA

401 TGCTCTTTAT CATTTTAAGC TATAGCTTTA ATTACAAAGA TGATAATTTT

451 CGCTGGGTAG tAGCTGCATC TTAATAANGG TCACCTAACT TGGTCCAAAA

501 AAATTGCAAC TGTTAGCCAG GGAAGAGGTT GTTTTAATTC AGTGATTGT

*************************************************************

Exon 15                    (SEQ ID No:22)
  1 TTTCTACTGA ATAATGACAT TTGATATAAG TAGGTCTCAA AGTCCGAAGA

51 AGAGAAGGCA TTTAAAAGAA TAATCTATTA ATTATATGAA GTAGTCTTTG

101 AATGATGTAG ATACTAGGTT AATGTTTTCC TTTGTAATAT ATTGCTAATA

151 CATATAAGGC AAAGCATTAG GTACTTGGTT TATATATTAA AGATCTTACT
```

TABLE 5-continued

GENOMIC ORGANIZATION
Each exon and its flanking intron sequences are listed
separately with the exon underlined. Exons are separated by a
row of ****. Example primers are in bold.

```
201 TTCTTGAAGT GAACACCACC AAAAAGATAA AGAAGAACTT TCATTCTCAG

251 AAGTAGAAGA ACTATTTCTT CAGACAACTT TTGACAAGAT GGACTTTTTA

301 ACCATTGTGA GAGAATGTGG TATAGAAAAG CACCAGTCCA GTATTGGCTT

351 CTCTGTCCAC CAGAATCTCA AGGAATCACT GGATCGCTGT CTTCTGGGAT

401 TATCAGAACA GCTTCTGAAT AATTACTCAT CTGAGGTGAG ATTTTTTAAA

451 AAAAGAACTA AGCTTATATA TGATTCAACT TTGGTAAACT GTTAGGAAGG

501 AGAAATAGGG GCAGGAAAAA CAGCAAGGAT GGTGGGAGGC TTCATTTTAA

551 AAGCAAAGTG GCAGTAAAGG GCTCTAAATT GGACAACTTA GCATAATTAA

601 AGGAAAACTC AAGAATAATA ATTTGAGTAC TTCCTTT
```

****************************************************************

```
                    Exon 16                     (SEQ ID No:23)
  1 CCATCAGGAG ATACTTAGGC TATTTTTCTT GAGAATCCTG GTTATAATTC

51 TACAGTGATC TCCTAGTTGT TTTTAGAGCT ATCCAGGATA TGCCACCTTT

101 AACTCAGTTA ACTGAACTTT TGTTTTTTAA TATGTATGTA GAATTTGTTC

151 TTACAAAAGA TAGAGTATAC TAAATTATTT ATGAAATATA TATATTTTA

201 TTTGTGGTTT ACTTTAAGAT TACAAATTCA GAAACTCTTG TCCGGTGTTC

251 ACGTCTTTTG GTGGGTGTCC TTGGCTGCTA CTGTTACATG GGTGTAATAG

301 CTGAAGAGGA AGCATATAAG TCAGAATTAT TCCAGAAAGC CAAGGTAGGA

351 GAATTTATAC TAATAAAGTT TCGGATAAAT TTGAATGAAA TGTATTCCTG

401 TGAAAATTAT TACATTTGTT TGGAAGACAT TAAATTGTAT GCAGGTTAAC

451 CCTTTCTCTT TTATTTATGT AATGTGAGAA GAAATTATAC TATGTATTTT

501 TTAAATTGTT TTAATTGTTT AATTTTTAAT TATTATTATA CTTTAAGTTC

551 TGGGGTACAT GATGCAGA
```

****************************************************************

```
                    Exon 17                     (SEQ ID No:24)
  1 AAGATTTGCC ATTTTAAAAA ATTGTTAATG AGTTTTGCTT AAACTGTATG

51 ACCACGTGGA ACTTCTAAAA ACATTTCATT TTTTCTCTTA AGTGCACTTT

101 ATTTTTTATT TTATAGTATG TCCAAGATCA AAGTACACTG AAAAAGCAA

151 TACTAAACTA TAATTTTAAC TGGAATTTGC ATTTTTCCTT CTATTCACAA

201 TAGTCTCTAA TGCAATGTGC AGGAGAAAGT ATCACTCTGT TTAAAAATAA

251 GACAAATGAG GAATTCAGAA TTGGTTCCTT GAGAAATATG ATGCAGCTAT

301 GTACACGTTG CTTGAGCAAC TGTACCAAGG TAAGATTTTC TTCTTCTTGT

351 TTTGTTTTTT GAGATAGGAT CTTTCTCTGT CACCCAGGCT GGAGTGCAGT

401 GGGATTGTCA CAACTCATTG TAGCCTTGAC CTCCTGGTTT CCAGCAATTC

451 TCCTGCCTCA GTCTCCCAAG TAATTGGGAC TACAGGCATG TACCACCTAG

501 CTAAAATTTT CTTTTTACTT GAAAGTGTAG C
```

****************************************************************

Exon 18                     (SEQ ID No:25)

TABLE 5-continued

GENOMIC ORGANIZATION
Each exon and its flanking intron sequences are listed
separately with the exon underlined. Exons are separated by a
row of ****. Example primers are in bold.

```
  1 TGTTGTTAAA GCACAATGAA AGATGTACAG TATAGTTATT ATAACTCTAA

51 GAAAAGATGT GTTTTTGAAG CAGCATATAT ATTGGCCCTA ATAGTAAACT

101 ATTTATCTAC ATTCCATTCA AGATAGAGAA AACACTGTCT GCCAAGAATA

151 ATTGTTTTTA TTTCTTTGTT GCTTGGTTCT TTGTTTGTCT TAATTGCAGA

201 AGAGTCCAAA TAAGATTGCA TCTGGCTTTT TCCTGCGATT GTTAACATCA

251 AAGCTAATGA ATGACATTGC AGATATTTGT AAAAGTTTAG TAAGTATGCT

301 TCCTGTTTTG CTATCATATT TTGATTCTAA TAGGCATAAT TTTTTTGTTG

351 AAATATCTTT GTAAATAAGG ATGCATCTCA CAACATATAG CTCTTAACAT

401 TTTTACAAAT GTGGAAATTA AGGCCAGGTG CGGTGGCTCA TGCCTGTAAC

451 CCCAGCACTT TGGGAGGCCG AGGTGG
```

****************************************************************

```
                           Exon 19                  (SEQ ID No:26)
  1 TTACAGGTGC CCACCACCAC ACCCAGCTAA TTTTTGTATT TTAAATAGAG

51 ACAAGGTTTC ACCATGTTGG CCAGGCTGGT TTCGAACTCC CGACCTCAGG

101 TGATCCACCT GGCTCAGCCT CCCAAATTGC TGAGATTACA GATGTGAGCC

151 ACTGTGCCCA GCCTGATTAG GTAAATTTTG ACTACAGCAT GCTCCTGCAA

201 GAAGCCATCT TGAACATCTT TGTTTCTCTT CCTTGAAGGC ATCCTTCATC

251 AAAAAGCCAT TTGACCGTGG AGAAGTAGAA TCAATGGAAG ATGATACTAA

301 TGGAAATCTA ATGGAGGTGG AGGATCAGTC ATCCATGAAT CTATTTAACG

351 ATTACCCTGA TAGTAGTGTT AGTGATGCAA ACGAACCTGG AGAGAGCCAA

401 AGTACCATAG GTAAATACAT ATTTACTACT TGGGATTTCT TTTACTTCTT

451 TATATTGATT TGGCAGTATA AGAGGCCTCA TTGATATCAA TTTTGTGCTT

501 ATTTCATTTT CTCTTAGTAT AGCCTTTTAG GATTGTTCCT TTCTTATATA

551 CTTTATTTTT TTTTTATTTT TACTGGAATT TATTAGTTTC ATATTTTATC

601 CTCCATAGAA GGAACTTAAG ATAACTATTA AAGA
```

****************************************************************

```
                           Exon 20                  (SEQ ID No:27)
  1 TTTAAATTAT TTCTTGACAA CAGAATCTTG GATAATTTTT CAAAAAGACT

51 TTTGAAGCTT TCAGTATATA ATTAATTTCA CTATAATTTT GCTTTTCATA

101 TACTTTTTTT TGTGAAGAGG AGGAAATTTG AGTTAATATG ACTATATATG

151 GCTGTTGTGC CCTTCTCTTA GTGTTAATGA GTGCTTTTTA TTTTTAGGTG

201 CCATTAATCC TTTAGCTGAA GAATATCTGT CAAAGCAAGA TCTACTTTTC

251 TTAGACATGC TCAAGTTCTT GTGTTTGTGT GTAACTACTG CTCAGACCAA

301 TACTGTGTCC TTTAGGGCAG CTGATATTCG GAGGAAATTG TTAATGTTAA

351 TTGATTCTAG CACGCTAGAA CCTACCAAAT CCCTCCACCT GCATATGGTG

401 AGTTACGTTA AATGAAGAAG CTCTTGGATT TTATCTGATG TTGCTGACTA

451 AATGTAATGA GTTGACATGT AAGAATCACA TGGTGTCTTT GAAGAATTGA

501 AATTGCTTTC TTGAGAAATG AACCTGAGAC TAGTTGGAAA ATAACACTTT
```

TABLE 5-continued

GENOMIC ORGANIZATION
Each exon and its flanking intron sequences are listed
separately with the exon underlined. Exons are separated by a
row of ****. Example primers are in bold.

```
551 TAACGTGCTG TGAGCAAATT TAAGTGGATG CTGAAATATT AAA
```

****************************************************************

```
                    Exons 21-22                    (SEQ ID No:28)
  1 AGGCGCCTGC CACCACCCCT GGCTAATTTT TGTGTTTTTA GTAGAGATGG
 51 AGTTTCACCA TATTGGCCAG GCTGTTCTCA AACTCCTGAC CTTGTGATCT
101 GCCTGCTTCA GCCTCCCAAA GTGCTGGGAT TACAGGTtTG AGCCACTGCA
151 CCCGGCCTAT GTTTATATAC TTTTTAAAGT AAATGATTTG TGGATAAACC
201 TGATTTTTTT CCCTCCTACC ATCTTAGTAT CTAATGCTTT TAAAGGAGCT
251 TCCTGGAGAA GAGTACCCCT TGCCAATGGA AGATGTTCTT GAACTTCTGA
301 AACCACTATC GTAAGAAATT AAAACCCTTA TGTTATGTTC ACTTTAAAGT
351 TATAAAATAA CTGATGTGTT CTTAAGCTTA ATAAAGTGGA ACTTTTTTTT
401 TTTTTTTACC ACAGCAATGT GTGTTCTTTG TATCGTCGTG ACCAAGATGT
451 TTGTAAAACT ATTTTAAACC ATGTCCTTCA TGTAGTGAAA AACCTAGGTC
501 AAAGCAATAT GGACTCTGAG AACACAAGGG ATGCTCAAGG ACAGTTTCTT
551 ACAGTAATTG GAGCATTTTG GTAGGTACAG TCTATTTTGT GGTCCTATTT
601 TTCTTTTGCT ATCTGTGGAT ACGAATGCAA GTTTTGTATC CACATCAGTG
651 ATTTCTTCTG ATCTGCCTAC ATAGCTAATA CATCTGGAAA GAATAGCAGA
701 ATGTTATTTG TGTTTCCCTC AGTCGCTTGA GAACTACAT TGCTTTTGT
751 TTAAGGCTTG GCTTTCTAA
```

****************************************************************

```
                    Exons 23-24                    (SEQ ID No:29)
  1 ATTCCTTTTA CCACTAATTT CCTTTTAGCT TGAATTTTTG GCAAGGTGAG
 51 TATGTTGGCA TATTCCACAT AATGACAAAT AAGTTTAGCA CAGAAAGACA
101 TATTGGAAGT AACTTATAAT AACCTTTCAG TGAGTTTTCT GAGTGCTTTT
151 ATCAGAATGA TTATTTAACT TTGGAAAACT TACTTGATTT CAGGCATCTA
201 ACAAAGGAGA GGAAATATAT ATTCTCTGTA AGAATGGCCC TAGTAAATTG
251 CCTTAAAACT TGCTTGAGG TGAGTTTTTG CATTTTTTA GTAAGATCTC
301 CATTGAAAAT TTTAAAGCAG TCTTTGTTTG TTAATGAGTA ATTTTTCTCT
351 ATTTCATATT TAACCACAGT TCTTTTCCCG TAGGCTGATC CTTATTCAAA
401 ATGGGCCATT CTTAATGTAA TGGGAAAAGA CTTTCCTGTA AATGAAGTAT
451 TTACACAATT TCTTGCTGAC AATCATCACC AAGTTCGCAT GTTGGCTGCA
501 GAGTCAATCA ATAGGTAATG GGTCAAATAT TCATGAAGTA TTTGGAATGC
551 TGCAGATGGC AGTAGAATGT CTTACATAGT AACAGCTCAC AGTTGCAATA
601 TTAAAAATAG CTAACACTTG TTGAGTATAT ACGGTGTGCC TGGCATTTAT
651 GTTTATTCTT AATTCTTATA CTTCTGTCAC TTAGATTCTA TTATTTCCTT
701 CAATTTATAA AT
```

****************************************************************

```
                    Exon 25                        (SEQ ID No:30)
  1 CTAAGCTGCT GGTCTGAACC TCTTTAAATA AACTCAGGTT TTGTTAGTCT
```

TABLE 5-continued

GENOMIC ORGANIZATION
Each exon and its flanking intron sequences are listed
separately with the exon underlined. Exons are separated by a
row of ****. Example primers are in bold.

```
 51 TTAAGAAAGA GCTAGTATGT TATTATGTCT CACAGAGTGA TTTATTTTTG

101 TTCTGGAATA TGCTTTGGAA AGTAGGGTTT GAAATTAGAA AATTATTTCA

151 CTTTTTGTTT GTTTGTTTGC TTGCTTGTTT TAAGATTGTT CCAGGACACG

201 AAGGGAGATT CTTCCAGGTT ACTGAAAGCA CTTCCTTTGA AGCTTCAGCA

251 AACAGCTTTT GAAATGCAT ACTTGAAAGC TCAGGAAGGA ATGAGAGAAA

301 TGGTAATTTT AAGTAACATG TATTTGCTGT TATCATATGC TTGCTATGAA

351 TATCCCATAA ATTACTTCAC CAAGTTTGGT ATAAGAGAGT TTATAATCCA

401 GTAGTTTACA GTATAAAGCT GCTCTTCCCC AACTGTATGA ATTGATTGAA

451 ACTGCATTCT TTCTGGGTCA CAATGGGTCA AATCATAGCA ATTTCTTTTG

501 GTTTAGCA
```

****************************************************************

Exon 26                    (SEQ ID No:31)
```
  1 AAAATTGGTA TGTAAACAAT TACAATTTAC ATTACAATTT TTTTTTAAAT

51 TTCTTTTTAA GTCCCATAGT GCTGAGAACC CTGAAACTTT GGATGAAATT

101 TATAATAGAA AATCTGTTTT ACTGACGTTG ATAGCTGTGG TTTTATCCTG

151 TAGCCCTATC TGCGAAAAAC AGGCTTTGTT TGCCCTGTGT AAATCTGTGA

201 AAGAGAATGG ATTAGAACCT CACCTTGTGA AAAAGGTATA TATGGATGAG

251 TATTTTATTA GAAGCTTCCT TAGGTCACTG TGAAATAATT TAAAAAGTTA

301 AAGCTAGATT TTCTGAGTGG CACTTATTTA AGACTAGGAA ACAATTTTAT

351 TTTTTAGGTT GGGAATATTG GAAAGCAGTT ATACAAAAAC TATTCAAATG

401 GTATATTTAT GGTATGCACT GTTTCTTACA TTCCA
```

****************************************************************

Exon 27                    (SEQ ID No:32)
```
  1 TGCTATGtGT CAGATACTGT GCCAGTTGAG TACATTTTCT TAATTATTAT

51 TCCCATCTCA TAGATGAGGA AATCAAGAAA AGTTGAATGA ATGTTGTTTC

101 TAGGTCCTAC TCTAAATAAT ATTAACAAGC ATTTAAATGA TTTATTTTTT

151 TCATTTTTCT TAACACATTG ACTTTTTGGT TCGTGCAGGT TTTAGAGAAA

201 GTTTCTGAAA CTTTTGGATA TAGACGTTTA GAAGACTTTA TGGCATCTCA

251 TTTAGATTAT CTGGTTTTGG AATGGCTAAA TCTTCAAGAT ACTGAATACA

301 ACTTATCTTC TTTTCCTTTT ATTTATTAA ACTACACAAA TATTGAGGAT

351 TTCTATAGGT AAGTTTATAC ATGACATATG TGAAATTTGT TTAATTTAAA

401 ATTAGTTAAC AATACTTAGC AAGTCCCCTC ACCAGCAACA CACATACCAT

451 ACCCATACAC ATGTGTGTGT GGGAGCCTAC ATAGTATGAG AAGCAGGACA

501 GCTTCTTTTA ATAAGAATGT ATTGAAGGGA GTCACTGGAC TTCAGATC
```

****************************************************************

Exon 28                    (SEQ ID No:33)
```
  1 ATTTTTTTAA TGTGACTATT TAGAATTTAC TTAATTTTTC CATTTATAAA

51 ATTAAAGAAT GTTTAATAAT CTGGATAAAG TATGATACTT TAATGCTGAT
```

TABLE 5-continued

GENOMIC ORGANIZATION
Each exon and its flanking intron sequences are listed
separately with the exon underlined. Exons are separated by a
row of ****. Example primers are in bold.

```
101 GGTATTAAAA CAGTTTTTAA GAACTATTTT ATAAAATTTT ACTTGGAAAA

151 GTTATATATA ACCTGTATTT TAAATTTTTC TATTTTTAGA TCTTGTTATA

201 AGGTTTTGAT TCCACATCTG GTGATTAGAA GTCATTTTGA TGAGGTGAAG

251 TCCATTGCTA ATCAGATTCA AGAGGACTGG AAAAGTCTTC TAACAGACTG

301 CTTTCCAAAG ATTCTTGTAA ATATTCTTCC TTATTTTGCC TATGAGGGTA

351 CCAGAGACAG TGGGATGGCA CAGCAAAGAG AGACTGCTAC CAAGGTCTAT

401 GATATGCTTA AAAGTGAAAA CTTATTGGGA AACAGGTAT GGCTTCAATT

451 TTTATGTACT TTTCATTCCC TGAATGATAT GAGATATAAC CTTTAAGTTT

501 TAAGGCTATT TATTCGATTT ATTCGTATTT ATATATTGAA ACTTAGCTTG

551 TGGTAATCAT TATCTAGCAT AGCCAACCCA TGAATTTTTT TGGTTATGTC

601 GTGTTGTCTC CCTCTGATTG GCTTTTAACT A
```

************************************************************

```
            Exon 29                        (SEQ ID No:34)
  1 GGGGGCCTTG TTTGGCTGAT TTTCATACTT TTTCCTCTCA GTCTACAGGT

51 TGGCTGCATA AAGAAAAAG GTAGAGTTAT TTATAATCTT GTAAATCTTG

101 GACTTTGAGT CATCTATTTT CTTTTACAGT CATCGAATAC TTTTGGAAAT

151 AAGGTAATAT ATGCCTTTTG AGCTGTCTTG ACGTTCACAG ATATAAAATA

201 TTAAATATAT TTTAATTTTG TGCCCTTGCA GATTGATCAC TTATTCATTA

251 GTAATTTACC AGAGATTGTG GTGGAGTTAT TGATGACGTT ACATGAGCCA

301 GCAAATTCTA GTGCCAGTCA GAGCACTGAC CTCTGTGACT TTTCAGGGTA

351 TGTACATTTT AAACTTAGAG AACTAGCTCT AACTTCACAA GTTTTTAAAG

401 AAGTTTATTG GTTGACACCT TCAATGTCTA TTTCAATTTA TAGACATCAC

451 TCTTTTTAAA AAATTTTCTT CAAAAATAGC CACCTTTGAA TTGAGGTAA
```

************************************************************

```
            Exons 30-31                    (SEQ ID No:35)
  1 TAATCTGATT TATATATCTG GACTGTGATA TGTCATTTGT GATTTTATTG

51 AAAGTATAGT TTTTCAGTAG AAAAATGGTT TTTGAATTTG GGGGTTATTA

101 AAATCTAAAT TTTCATTTTG GAAGTTCACT GGCTATGAAC AAAACTTTTT

151 AAAACGATGA CTGTATTTTT TCCCTTAACT CTGTTAGGGA TTTGGATCCT

201 GCTCCTAATC CACCTCATTT TCCATCGCAT GTGATTAAAG CAACATTTGC

251 CTATATCAGC AATTGTCATA AAACCAAGTT AAAAAGCATT TTAGAAATTC

301 TTTCCAAAAG CCCTGTAAGT ATACATGATG AGTTTAATAA TAGAACATTC

351 CTTCTTTTTT AGCTAAAAAA ACTTTGTAAA TACATCTTAA AGAGGAAAAG

401 TAAACAAATG AAAAATTTAT CTCATAATTA AAAGGAAAA CATTCATTTA

451 CAAGTTTAAA TGGTATTTTA CTTGTCAGCA TTAATTGAAA TATGTTACAT

501 ATGAGAACAG AATCTTGTGA CACTTTAGTG ATATATTAGC TCAGGGAATA

551 TATCTACTTT TTCATAGGAA TATACTATTT AATTGTAGTT TACTTTCTGA

601 AAATTAAATA AATTGGCAAT AGTTTAAGAT AGTAATTTTC TTAATGTAAC
```

TABLE 5-continued

GENOMIC ORGANIZATION
Each exon and its flanking intron sequences are listed
separately with the exon underlined. Exons are separated by a
row of ****. Example primers are in bold.

```
 651 ATTTTGTACT TGATATCAAA CCCAAATCTA AATTCTGTTA TTTAGTTATT

701 TTAAATATAA AATGTGTAGG TATTCAAATA TTTGAAGAAA AAATATAAAG

751 TGTATTTATT GTAGCCGAGT ATCTAATTAA ACAAGTTTTT ACTAAATCTG

801 TTTATTTTCT TAGGATTCCT ATCAGAAAAT TCTTCTTGCC ATATGTGAGC

851 AAGCAGCTGA ACAAATAAT GTTTATAAGA AGCACAGAAT TCTTAAAATA

901 TATCACCTGT TTGTTAGTTT ATTACTGAAA GATATAAAAA GTGGCTTAGG

951 AGGAGCTTGG GCCTTTGTTC TTCGAGACGT TATTTATACT TTGATTCACT

1001 ATATCAACCA AGGTAAATA ACATATTTAG ACCAATATAT AAGCAGTCTT

1051 TCTATCCTGT TCTTCCTGTT TTTTTGCTTT GTTTTGTTTT GTTTTGAGAC

1101 AAAGACTCAC TCTGTCCGCC CAGGCTGGGT GCAGTCACGG CTCACTGCAT

1151 CCTCAACCTC CTGGGTTCAG ATTATCCTTC CTCCTCACCC TGCCGGGTAG

1201 CTGGGGCTAC AGGAG
```

****************************************************************

```
                 Exons 32-33                      (SEQ ID No:36)
   1 ATGTTTCTAT TAAAGGATGG AAGCTTAGAG CTGCCTATTC TGCATTTTGC

51 TGATGTGACT TCTCTTTTTG GCTTATAAGC CATTAAAATA TTTTNGTCAA

101 GGCATATAAG AATTAGAGAT GCTGAACCAA AGGACTTCTG AATGAATTTA

151 TTTCAGAGTA ATTTTCCAGA ACTTACTGGT TGTTGTTGTT TTTTTTTCTC

201 CCTATATTAG GCCTTCTTGT ATCATGGATG TGTCATTACG TAGCTTCTCC

251 CTTTGTTGTG ACTTATTAAG TCAGGTTTGC CAGACAGCCG TGACTTACTG

301 TAAGGATGCT CTAGAAAACC ATCTTCATGT TATTGTTGGT ACACTTATAC

351 CCCTTGTGTA TGAGCAGGTG GAGGTTCAGA AACAGGTAAT TTTCTGACTC

401 ATCTTCAAAA ATGGTATTTA AAATATATAA AGTATTGTTA GAAGGATTTG

451 AGTGTTTTAT GTTTATTTGG TATAATTGGT GATTTTATTG AGAATATTTT

501 TTGTAAAATG ATTGGAAAAA TATTCTTAAT GAATTAACCT TTGTAATCAA

551 TTACAGAGCA CTTGGTACTT TTGATAGTTT TATCTACTGT GCTGAAGTGG

601 AGAGGTAGTC AAAACTAGGG ATAGCAGTTC GCAACGTTAT GGTGGTATTT

651 GAGTTACTAC TTATATAAAC TGTTTCATTA ATATTGGCAT TTTTTTTAAC

701 CTCAGTACCC ATCTTGTAGT AGTACCTTAC ATAGTTATTG AATTATTTGA

751 AAACACAGAA ACTAAAAGCT GGGTATCTTA GACGTAATAA GAACATTTAA

801 TCTGATCTAG GTTAATAGAT TTTATCATTT ATTACAGTAA GTTTTGTTGG

851 CTTACTTTAA AATTATTTCT CTCCTTATAA TTTTTTCTTT TTAAATTATA

901 TTTAGGTATT GGACTTGTTG AAATACTTAG TGATAGATAA CAAGGATAAT

951 GAAAACCTCT ATATCACGAT TAAGCTTTTA GATCCTTTTC CTGACCATGT

1001 TGTTTTTAAG GATTTGCGTA TTACTCAGCA AAAAATCAAA TACAGTAGAG

1051 GACCCTTTTC ACTCTTGGAG GTAATAAAAA TTTCATCATC TACTATTTTT

1101 TATTAGAGAA CATAGTAGTA CTTTTCAAAA ATCTGTAATG CTCTAGCAGT

1151 AAAAAATGGA ATCTTTTCTT TAATTGTGAT TAAAAATATA TACGTAGGCC
```

TABLE 5-continued

GENOMIC ORGANIZATION
Each exon and its flanking intron sequences are listed
separately with the exon underlined. Exons are separated by a
row of ****. Example primers are in bold.

```
1201 AGGCACATTG GCTCATGCCT ATAATCTCAG CACTTT

****************************************************************

Exon 34                          (SEQ ID No:37)
  1 GACTCTGTCT AAAAAAGAGT ATTAAAACAT TGTAGGGTTT GCAGTGGAAG

51 AAATCATTTA TTTCTTCCTT GATTAGTAGT AATAGAGACA TGAGTCAGTG

101 TCTATAAATG GCACTTAACT AATTTTTTTC TTTTATTAAG TTTTATTTCA

151 CAGGCTTAAC CAATACGTGT TAAAAGCAAG TTACATTTTC TCTTTTAGGA

201 AATTAACCAT TTTCTCTCAG TAAGTGTTTA TGATGCACTT CCATTGACAA

251 GACTTGAAGG ACTAAAGGAT CTTCGAAGAC AACTGGAACT ACATAAAGAT

301 CAGATGGTGG ACATTATGAG AGCTTCTCAG GGTGCTAATT TTAAATGACA

351 TGGGCTATTT CTACCTGTTT CTTTTTGGAA AGAATATTTT GCAAAGTCTT

401 GCTCTTGGTT TCATTGTCAC AGACTTAGTT CAGACTCTCA TCATTTAGTT

451 CAGACCCTCA TTTCTCATCT AACTGTAAAA CTGGTCCTAA CTGGTCTTCT

501 CACCCTGAAC TCTTCCTGTT TTATTCATCC TCTGCCAGAT G

****************************************************************

Exon 36                          (SEQ ID No:38)
  1 ACCTCTGTCT CCCAAAGTGC TGGGATTACA GTCGTGAGCC ACCGCACTCG

51 GCCTTAAGGT TAATTCTTGA AGTACAGAAA ACAGCATTA TAGTTTGGAA

101 ATTAGAAAAT ATCAGTTTTA TGTATGATCT CTTACCTATG ACTCTACTGA

151 AATAGAATTT CTATATGTAG AGGCTGTTGG AAGCTGCTTG GGAGAAGTGG

201 GTCCTATAGA TTTCTCTACC ATAGCTATAC AACATAGTAA AGATGCATCT

251 TATACCAAGG CCCTTAAGTT ATTTGAAGAT AAAGAACTTC AGTGGACCTT

301 CATAATGCTG ACCTACCTGA ATAACACACT GGTAGAAGAT TGGTGAGTAT

351 TTATTGATAC CTTATATGTA ATCTCAATAT GACATTCATG GAGAATGATA

401 CTTCACACAA ATAGATATTC TCAGTAACTA AGCTTTGTC CTTTTTTAAA

451 TCTCAGTGTC TTTATGAAAA TTCTTATATT TTTATTAATT CACATAATTA

501 TTTACCCTAC TATGTGCCAG ACACTTGATA TAATGGT

****************************************************************

Exon 37                          (SEQ ID No:39)
  1 GTTGCAGTGA TTAGTAATTC AAGTTTACTG AATGACTAGT GAAAGTCCTT

51 TGATACTTTT ATTTGATATT GGAGAATTTT GTAAATGTAA AGTTTCCTAA

101 AACCAATTTT AAATTTTAGT TTGAAATTT TTTCAGTGGA GGTTAACATT

151 CATCAAGATT AATAACTGGT GTACTTGATA GGCATTTGAA TTGTTTTTTT

201 CAGTGTCAAA GTTCGATCAG CAGCTGTTAC CTGTTTGAAA AACATTTTAG

251 CCACAAAGAC TGGACATAGT TTCTGGGAGA TTTATAAGAT GACAACAGAT

301 CCAATGCTGG CCTATCTACA GCCTTTTAGA ACATCAAGAA AAAAGGTCTC

351 TTAAGTAATA AATGTTTATT GAATACCCAG CATATCTAAA ACAGTTCTGT

401 TTGCTGTGGG TCATGACTGT TAAATTGCTT GAAATAGTAT TGTACTAACT
```

TABLE 5-continued

GENOMIC ORGANIZATION
Each exon and its flanking intron sequences are listed
separately with the exon underlined. Exons are separated by a
row of ****. Example primers are in bold.

```
451 ATTAACCTTT CCTATAAGTA ATTTAAGCCA TATTTCATAA ATCCAGGGAA

501 TGTGTTATTT TTAATTTATT ATGGCAGTGT G
```

****************************************************************

```
                        Exon 38                     (SEQ ID No:40)
  1 AAACATAAAT GTTTTCATCT TAAAAGGTAA ACATTGCCTC CAGATTTAGT

51 TTTAACTGTA TTTAGCTTTA TTCAGAAAGA TTTGTTATAC TCATTTTGTG

101 TAGGAAAGGT ACAATGATTT CCACTTCTCT TATTTACATT TTCTAATCCC

151 TTTCTTTCTA GTTTTTAGAA GTACCCAGAT TGACAAAGA AAACCCTTTT

201 GAAGGCCTGG ATGATATAAA TCTGTGGATT CCTCTAAGTG AAAATCATGA

251 CATTTGGATA AAGACACTGA CTTGTGCTTT TTTGGACAGT GGAGGCACAA

301 AATGTGAAAT TCTTCAATTA TTAAAGCCAA TGTGTGAAGT AAGAAGATTA

351 ATTAGTCTGA TATAATTCCT TGTTTATGAC CTGTTTATCT AAAGAGTGCT

401 GTGATACTGC ACATCATCTT CACATAATAT CACCCCCACT CAAACTGTTG

451 TAAATTTATT AAAGTGAGCA TCCGTATTTA GTCATAACTT TATGCATTAG

501 GTTTCAGCTT CGGGATAGCA ACATACT
```

****************************************************************

```
                        Exon 39                     (SEQ ID No:41)
  1 CCTAGTGTGG TTTTTTAAAC ACCACCTAAT ACATGTTTTT TGTTTGTTTT

51 TTTAGCAGTA TGTTGAGTTT ATGGCAGATT AATCTATCAT CTTTTAGAAA

101 TTTAATATGT CAACGGGGCA TGAAAATTTT AAGTAAAATG TATTAATTTT

151 ACTCATTTTT ACTCAAACTA TTGGGTGGAT TTGTTTGTAT ATTCTAGGTG

201 AAAACTGACT TTTGTCAGAC TGTACTTCCA TACTTGATTC ATGATATTTT

251 ACTCCAAGAT ACAAATGAAT CATGGAGAAA TCTGCTTTCT ACACATGTTC

301 AGGGATTTTT CACCAGCTGT CTTCGACACT TCTCGCAAAC GAGCCGATCC

351 ACAACCCCTG CAAACTTGGA TTCAGGTATT CTATTAAATT TTTAACATTA

401 ATACTGTAAA CTCAGTTCTA GAGAAAGATG GATTTAAGAT GGAATCCCAC

451 TAAAAGCACT TTACAGGATT AAATCTATAA CCTCTAAATT TGTTTCTTCA

501 TCTATGGAAT GGAGATAAAA GTTGCCAACA GTTGCAACAA GTTTTCAATG

551 AAATAATGTG TGTAAAG
```

****************************************************************

```
                        Exon 40                     (SEQ ID No:42)
  1 TAAGTTCTCA CTTTTTTTAA GATAACAGTT TCTTTTAAAA GCAAAAGAAA

51 TCCTATTAAA TTCCTTCAGA ACCAATTTTG TGTTAGGTAC TGCCCACCAG

101 AACCTTATAG CATAGTGGGA GACAGACACA TAAACAAGAA GGAAGAAGGT

151 GTGTAAGCAA GAATGCCTGG GACTGAGGGG AGATATTTTT GTTTGTCAGA

201 GTCAGAGCAC TTTTTCCGAT GCTGTTTGGA TAAAAAATCA CAAAGAACAA

251 TGCTTGCTGT TGTGGACTAC ATGAGAAGAC AAAAGAGGTA ATGTAATGAG

301 TGTTGCTTCT TACGTTTAGG ATCTAGAGTG TAACTTGTTA ACTATCGGCT

351 GAATTTTAAC ATGATTATTT TAGGTGAAGG TGTTGCAAAG TGTTATATTT
```

TABLE 5-continued

GENOMIC ORGANIZATION
Each exon and its flanking intron sequences are listed
separately with the exon underlined. Exons are separated by a
row of ****. Example primers are in bold.

```
401 AATTTGTGTG ATATTTATAT CTCCTTGCAG tAATCCATAT TCAGGATAGC

451 AGTTTGGTTA AATCAGTGTC AAGAA

****************************************************************
                    Exon 41                           (SEQ ID No:43)
  1 TTAATTAAAT AGGACTCTTC AGCCATGTTA TCTTATAATG TTTATAGGTA

51 TATATTGGGG AAATGTGGTT TTTGGGAATT TGTAATTTTC TGTTAAGCAG

101 TCACTACCAT TGTATTCTAT ATCAACATGC TTTTATTTTG ATATTGAAGT

151 TTAAAAAAGT GAATGACATT ATATCTCATT TTTCTTTAGA CCTTCTTCAG

201 GAACAATTTT TAATGATGCT TTCTGGCTGG ATTTAAATTA TCTAGAAGTT

251 GCCAAGGTAG CTCAGTCTTG TGCTGCTCAC TTTACAGCTT TACTCTATGC

301 AGAAATCTAT GCAGATAAGA AAAGTATGGA TGATCAAGAG AAAAGGTAAT

351 GGAATTTAGA ATTTTTGGTT TTTAAAATTA ATGTTGGCAT TGTCTCAATA

401 AGGGTATATA GTAAAGATTT ATTTTGCCTC CTGTTCCCCA TTTAAAAGAT

451 ATTTTAGATA GAAATTTTGT TTTAAAGTGA AATTATAATA AATTTTTAAA

501 AAGGAATATG TAATTCCTGT TCTGAAAT

****************************************************************
                    Exon 42                           (SEQ ID No:44)
  1 CTTTTCCATC CTAGGTATAA ATGGTATTAT GTTTTAAAGT ATAAGTGATT

51 TATTCTGTTT TGTTTGCCAC CTTCATTAGT TTTTTTCTGT CAAAGTCTAT

101 AGTATATGTA TTCAGGAGCT TCCAAATAGT ATGTTCTCAT TAAAAGAGGT

151 GTTCTTGTGA CAAACAGAAG TCTTGCATTT GAAGAAGGAA GCCAGAGTAC

201 AACTATTTCT AGCTTGAGTG AAAAAAGTAA AGAAGAAACT GGAATAAGTT

251 TACAGGTAAA TATTAGAGGC TCTATTATTT ATGACAGTAT TTATCTCATA

301 CTTTGGGTTA TTTTGTTATA GACACTGTAC AGATGCCATG TGATTTTTAA

351 ACTGAATTTA CTTACTGGAC TAAGCATCAT ATATATAAAA TTATGGTCTG

401 AAGCTTAAGC CTTAGAGTAG ACAGACTTGA GTTCTAATAC TGAC

****************************************************************
                    Exon 43-44                        (SEQ ID No:45)
  1 TTGTCCTGCA CAGTTCAAAC TCGTGTTGTT TGAACTGTAT TTCAGAACTG

51 TATTTCAGAA TCATTACATT TTATTTCTAT AACATAACAT TTAGAGTTGG

101 GAGTTACATA TTGGTAATGA TACAATTTAA AATTTGCTAA ATTTATAGAC

151 CGATTTTTTT TCCTTCTTCA ATTTTTGTTG TTTCCATGTT TTCAGGATCT

201 TCTCTTAGAA ATCTACAGAA GTATAGGGGA GCCAGATAGT TTGTATGGCT

251 GTGGTGGAGG GAAGATGTTA CAACCCATTA CTAGGTAAAT TGCATTTTTC

301 TAAACAACGG TATAGTAATT CTGTTTATGA AGGAGTTATG TGTGTGTTAA

351 ACCCAAAGCT ATTTTCACAA TCTTTTCTTA TAGACTACGA ACATATGAAC

401 ACGAAGCAAT GTGGGGCAAA GCCCTAGTAA CATATGACCT CGAAACAGCA

451 ATCCCCTCAT CAACACGCCA GGCAGGAATC ATTCAGGTAC ATTTTTTCCC
```

TABLE 5-continued

GENOMIC ORGANIZATION
Each exon and its flanking intron sequences are listed
separately with the exon underlined. Exons are separated by a
row of ****. Example primers are in bold.

```
501 AGATTTGGTA AAGCCATCAC TAGTGTAGTG CTGAGGTTAT TTCAGTATGT

551 TGGTGGATAT TTACACAGCC AGATAAACTC TAGAGATAAG ACTAGAACTT

601 ATCTGTTTTT CAGAGGATTA GGCTAAACAT TCAGGGATAC TCCTGAAGCA

651 GAGGGATGCA AAAAAAAGAG AAAAAATTCA GGGAGACA
```

****************************************************************

```
                          Exon 45                      (SEQ ID No:46)
  1 CCTCCTGCCT CAGCCTCCCA AAGTGCTGAG ATTACAGGCA TGAGCCACCA

51 CACCCAGCTG ATATTTTGGG ATTTTAAATG ATATTGTGAA CTAAAATTTG

101 TCTAAGTTAA TTTGTATCTT TGCTGTTTTT TTCTCTGGTT TTCTGTTGAT

151 ATCTTTGATT ACTTAACTTA AAAACAAAAT AACTCCTGTT TAGGCCTTGC

201 AGAATTTGGG ACTCTGCCAT ATTCTTTCCG TCTATTTAAA AGGATTGGAT

251 TATGAAAATA AAGACTGGTG TCCTGAACTA GAAGAACTTC ATTACCAAGC

301 AGCATGGAGG AATATGCAGT GGGACCATTG CACTTCCGTC AGGTAAGAAA

351 TTTGACTTGA TTTTTTTTTT TTTGCCTCTC TCCTCATTCT AAACAACAAC

401 TGTTTTTCTC TTCTATGA
```

****************************************************************

```
                          Exon 46                      (SEQ ID No:47)
  1 TTTTTCTGCT TAAAGAATTT AAATGACTCA TAAAATTTGT ATTTCTTACC

51 AAAAATTCTA GAAATGCATT TTTTAGAATG GAGAAATGTT AATTTAAAAA

101 TTTTGTCCTT TGGTGAAGCT ATTTATACAT GTATATCTTA GGGTTCTGTT

151 TTTAAGTATA TTTTTTTCTT TGACTTATCT CACAGCAAAG AAGTAGAAGG

201 AACCAGTTAC CATGAATCAT TGTACAATGC TCTACAATCT CTAAGAGACA

251 GAGAATTCTC TACATTTTAT GAAAGTCTCA AATATGCCAG GTATTATGAA

301 AAGACAAAGT TACTGTATTT TAACATTTAA TGTCATGGCT TCTTTTCTGA

351 AAACTTGAGA AACAATTTTA ATGTAAGGAT TTGCATTGAT GAAGAGATAA

401 AGACTTGGTG GCTGTGATCA GATGTTTCCT TGTAATTCTC TGCCCTCCTT

451 CAAAACAAAT TGTTTCTGGG ATTCCAGGTT CATTCTTTAC CCTGACCCTT

501 CAAGAAAGTT TTG
```

****************************************************************

```
                          Exon 47                      (SEQ ID No:48)
  1 AGTGTAAGTG GACCATGCAT TTAAATTTGT GTTGTTCAAG GGTCAGTTGT

51 ATTCTGTTTC CACTGCTATT TTGTACTCAC TGCTGCTTGT TAGTATTATT

101 AGATCAGTAG CATAGCCTAT GATGAGAACT CTTTAACAAC AAATTTAAAC

151 ATTTATTTCC CTGCAAACCT CTTCTTTATT TTCAGAGTGT CTTTTCTTTT

201 TTGCTACTAG AGTAAAAGAA GTGGAAGAGA TGTGTAAGCG CAGCCTTGAG

251 TCTGTGTATT CGCTCTATCC CACACTTAGC AGGTTGCAGG CCATTGGAGA

301 GCTGGAAAGC ATTGGGGAGC TTTTCTCAAG GTATGTAATT CGTATGACTT

351 TGTTATCCTA AAGTGCAGCT TTTCTGTTAC CAATAGTGAC TTTAAAAAAT

401 AAAAACTATA GGCCGGGCAC GGTGGCTCAT GCCTGTAATC CTAGCACTTT
```

TABLE 5-continued

GENOMIC ORGANIZATION
Each exon and its flanking intron sequences are listed
separately with the exon underlined. Exons are separated by a
row of ****. Example primers are in bold.

```
 451 AGAAGGCTGA AGTGGGTGGA TCACTTGAGG TCAGGAGTTC AAGACCAGCC

501 TGGCCAACAT GGT

****************************************************************
              Exons 48-49                          (SEQ ID No:49)
   1 TGTATTATTA TAATATTATA TCGTAAGTTC CAGGACTTAC ATAGTTTTTT

51 TTTTTTTTTT TTCATTTCTC TTGCTTACAT GAACTCTATG TCGTGGCATT

101 CAGATCAGTC ACACATAGAC AACTCTCTGA AGTATATATT AAGTGGCAGA

151 AACACTCCCA GCTTCTCAAG GACAGTGATT TTAGTTTTCA GGAGCCTATC

201 ATGGCTCTAC GCACAGTCAT TTTGGAGATC CTGATGGAAA AGGAAATGGA

251 CAACTCACAA AGAGAATGTA TTAAGGACAT TCTCACCAAA CACCTTGTAG

301 AACTCTCTAT ACTGGCCAGA ACTTTCAAGA ACACTCAGGT AAATACAATT

351 TAAAACTATG TCATCTTACC TCTTGACTTT CCTTTTATTA TTTAAAAAAC

401 TGAAAGCCTG AGGGAAAAAG AAATGTCATT AAGAGATAGA GATCTCTATT

451 AATATATAGT AAAAATAATT GTTAAGAGT  TCCCATTTTG GAATTAGATC

501 TGACTTTTAA GCCTTGGGCA AGGGTACTTA ATCTTTCTC  AACCTCAATT

551 TCCTGGTTAT AAAATGAGAA GATACCTAAC TTACTATATT GATAACAATT

601 CAGTGATTTT ATATACTGTG TGTATGTACA CACAGATACA CATACATACA

651 TATAGAGAGA GACAGACAGA CAGACAGATA GGCAGACGTG GGGTGGGGAG

701 ATTGTCAATG CAGACAGAGA GGGTCCTTAA AGATAGTCCC TGACAAGTAG

751 TTAAAGTCCT CAAATGAATG GTAGTTGCTG CTTTCATTAT TATTATTATT

801 CAAGGTAGTA GTATCAAGTA GTAAAAGTAT TTATTCCCAT ATGTCATTTT

851 CATTTCAGCT CCCTGAAAGG GCAATATTTC AAATTAAACA GTACAATTCA

901 GTTAGCTGTG GAGTCTCTGA GTGGCAGCTG GAAGAAGCAC AAGTATTCTG

951 GGCAAAAAAG GAGCAGAGTC TTGCCCTGAG TATTCTCAAG CAAATGATCA

1001 AGAAGTTGGA TGCCAGCTGT GCAGCGGTTT GTTTTTTTTA TTGGCTGGAT

1051 TAGTGTTTTA CTGTTATTTA AAAAAACACA AATGTACTTT AAAATATTTT

1101 TAATAACAAT TTTATTAGAG CCTTGAAATT AGTAATTTAT TAACAAGATA

1151 TTGTAAAACT AGTCTTGAAA ATTAATTTGT AAATGAAGTT TAGAAACTTT

1201 TTCCTATATA TCACAATTCT ATCAGTCCAT CATGTGGTCG ATTCATTTAA

1251 TATA

****************************************************************
              Exon 50                              (SEQ ID No:50)
   1 TAATAATAAT AAACAGAGGA TGATCATTTC CtACATGGGA TTATTAAAAT

51 AGTTGTATGG CAAAAGCAGA TGAGGAAAAA CTTTTTTTTT CCCACCCACC

101 AAGGAAAAAC ATTTTTAACC TGCTTTTTTC CCCCGTACAT GAAGGGCAGT

151 TGGGTACAGT CATGGTAATG CATTATATTT TAAGATTTTG CCTTTCTTAT

201 ACAGAACAAT CCCAGCCTAA AACTTACATA CACAGAATGT CTGAGGGTTT

251 GTGGCAACTG GTTAGCAGAA ACGTGCTTAG AAAATCCTGC GGTCATCATG
```

TABLE 5-continued

GENOMIC ORGANIZATION
Each exon and its flanking intron sequences are listed
separately with the exon underlined. Exons are separated by a
row of ****. Example primers are in bold.

```
301 CAGACCTATC TAGAAAAGGT AAGATTTTTG GAGCAACCCT TAAGATAGTT

351 ACTTAGCATG AATATGCTTC ATCTTTTCAT CAAGATCAAT ATATTTCCAA

401 AGCAAATAAA AGTATGGTTT TATTTTTCTA TATATTATTA CTGTTGTAGC

451 TCTGTATAGT CTCTAGGGTG GAGTGAAACA TTGTTACAAA ACAAAGCAGC

501 CAATTTGAAA AGTAAGCCCA AGTATAGTAT CTCTTCT

****************************************************************

Exon 51                    (SEQ ID No:51)
  1 TTTAAGAAAA TGTACGAATT TGTGTTGGGC CACATTCAAA GCCGTCCTGG

51 GCCACATGCG GCCCATGGGC CGTGGGTTGG ACAAGTTTGC AATAGTTCAT

101 ATAATTTAGC TAGCTTTTAT ATGTATATAA GTTAAATTTT AGTGTATTAC

151 CTTAATTTGA GTGATTCTTT AGATGTATTT AGTATTTGTA AATATAATTT

201 AAATTGGTTG TGTTTTCTTG AAGGCAGTAG AAGTTGCTGG AAATTATGAT

251 GGAGAAAGTA GTGATGAGCT AAGAAATGGA AAAATGAAGG CATTTCTCTC

301 ATTAGCCCGG TTTTCAGATA CTCAATACCA AAGAATTGAA AACTACATGA

351 AATCATCGGA ATTTGAAAAC AAGCAAGCTC TCCTGAAAAG AGCCAAAGAG

401 GAAGTAGGTC TCCTTAGGGA ACATAAAATT CAGACAAACA GGTAACTAGG

451 TTTCTACAAG TGACAATTTT ATGTTCACCA GTTAACTGAG TGAGTGTTTT

501 TGCATAGAAA GAGTGACTTG GTCTTTTTAT CTGATATAGT TTTGAGCTCT

551 AAAGGTCGGC TTAACTATAT ATAGATTATC TTGGTCTTTT GGGTTCTTTT

601 CGGTTTTTGT TTTTTGTGTT TTTTTTGAG ACAAGGTCTC ACTCTGTCAC

651 CCAGGCTGGA GTACAgtGGc GTGATCACT

****************************************************************

Exon 52                    (SEQ ID No:52)
  1 TCCCCTTTGT CCTTTGATGC TTAGGAAGGT GTGTGAATTG CACAGTTAAG

51 ACAAAAGTAA GTTTATTCCC TTTATAATCC TTAGAAGTTT GCTTTTTTCC

101 CTGGGATAAA AACCCAACTT TTTTCATTAA ATGTTGTATA TCATGTGTGA

151 TTTTGTAGTT CTGTTAAAGT TCATGGCTTT TGTGTTTTAC CTTAATTATT

201 CTATGCAAGA TACACAGTAA AGGTTCAGCG AGAGCTGGAG TTGGATGAAT

251 TAGCCCTGCG TGCACTGAAA GAGGATCGTA AACGCTTCTT ATGTAAAGCA

301 GTTGAAAATT ATATCAACTG CTTATTAAGT GGAGAAGAAC ATGATATGTG

351 GGTATTCCGG CTTTGTTCCC TCTGGCTTGA AAATTCTGGA GTTTCTGAAG

401 TCAATGGCAT GATGAAGGCA AGTGTTACTC AGCCCAATAT TCTACCCTGT

451 GCTTGAAAAA CTTAGACATA AGCCCCTTGA TGTCAGGAAT CGTGTATACC

501 TCTTTGTATT CCTAGCACTT GGTCCAGTGC TCTACACATA AGTAGCATTT

551 TGTAGTTTTC TAAACTTTGA TCCATATTTA GGATTATTTA CAAGTTCTAG

601 TCTTGTTTCT

****************************************************************

Exon 53-54                 (SEQ ID No:53)
```

TABLE 5-continued

GENOMIC ORGANIZATION
Each exon and its flanking intron sequences are listed
separately with the exon underlined. Exons are separated by a
row of ****. Example primers are in bold.

```
  1 AATCCAGTTT AATTTAGGAC CCAATATTTT GATTTACCAA TGCATTAATC

51 TAGAGTACCC ATTAGAAAGA CCTTCAGATA AGAAAAGAAA TGAAGGAAAA

101 CAATATAGTT AGTGAAGTTT TGTTAACCAC TTGTGCTAAT AGAGGAGCAC

151 TGTCTTAAAA TAACTTACTT GCTTAGATGT GAGAATATTT GAAATACCTT

201 GTTTCTTAAT TTTGTGTCTT TTTTTTAATG GTAGAGAGAC GGAATGAAGA

251 TTCCAACATA TAAATTTTTG CCTCTTATGT ACCAATTGGC TGCTAGAATG

301 GGGACCAAGA TGATGGGAGG CCTAGGATTT CATGAAGTCC TCAATAATGT

351 AAGTAAACCT GAAAATCAAA CCACAATAAT TATTTTTATT CTATTATTAC

401 TATATATTAT ATAAAGTATA TATACCATTC CCTCTAAGAA ATGGAAATAC

451 AAAATTTTGT ATTTTTTGTC TTCTCACATC ACATAAGTTA CTCATTTTCT

501 CTCTCTAATT CCTCATAGGC CTCTGCCTTT TTCTCACACA TGCAGGCATA

551 CACGCTCTAC CCACTGCAGT ATCTAGACAG TAATACACAT TTTAATGTTA

601 AGCAAAATGA AAAATATGGA TTATATTTTT TTGTTTATTT GCATAAATCT

651 AATAGTTCTT TTCTTACAGC TAATCTCTAG AATTTCAATG GATCACCCCC

701 ATCACACTTT GTTATTATA CTGGCCTTAG CAAATGCAAA CAGAGATGAA

751 TTTCTGACTA AACCAGAGGT AGCCAGAAGA AGCAGAATAA CTAAAAATGT

801 GCCTAAACAA AGCTCTCAGC TTGATGAGGT ATTGGGATTA ACCATACGTA

851 CCTTTTAGAA GTGTGATATT CAGTCTTTCC TAGAATATTT CTTTTTAAAA

901 TCTTGTGTTA TTAAGATGCC ATCTAAAATC GGTTCAAGGC TGGCACGGTG

951 GCTCACGCCT GTAATCCCAG CACTTTGGGA GGCTGAGG
```

****************************************************************

Exon 55                    (SEQ ID No:54)
```
  1 GAAAGGCACC TAAGTCATTG ACGAGAGTAT GTATCTTTGA TGTATTTCAT

51 TTATGACTGT TTTGTTTGTA TCTGAGGAAT TATAATCATT CCATAGTCTA

101 GATTTGTGCA TAAATTCTGT TTTTCTCTTT GTTTTTCTAA CTCTGAGAAG

151 TTTAAATGTT GGGTAGTTCC TTATGTAATG TTTTTTGTTT TTTATTAATA

201 GGATCGAACA GAGGCTGCAA ATAGAATAAT ATGTACTATC AGAAGTAGGA

251 GACCTCAGAT GGTCAGAAGT GTTGAGGCAC TTTGTGATGC TTATATTATA

301 TTAGCAAACT TAGATGCCAC TCAGTGGAAG ACTCAGAGAA GTATGTTTTT

351 TTTAAAGAAG AAACGTTACT TTCTTGCTGT GTTACTCTCT GTAGAGATAT

401 ATTAGTTATA GAGCCTAATA AGTAAATCTG CTTAAAATCA CAAACGTAAT

451 CCAAAAGCTT AATTTATATC TGATGGCTTC AACATTCCCT GGTTACTTTT

501 TCACTTAATA TCTCTTAATA GAACTGGTAA TAGGTGA
```

****************************************************************

Exon 56                    (SEQ ID No:55)
```
  1 CTGTTGAGCT TTGACTCTGA GCTGCATAGT GGCCAAAGCC CAGAGTCTTC

51 ATTTCTCAAT CAGAGCCTGA ACCACAGATT AGCAACAAGT TGGGGCCAGT

101 GGTATCTGCT GACTATTCCT GCTTGACCTT CAATGCTGTT CCTCAGTTTG
```

TABLE 5-continued

GENOMIC ORGANIZATION
Each exon and its flanking intron sequences are listed separately with the exon underlined. Exons are separated by a row of ****. Example primers are in bold.

```
151 TCACTAAAAT CTCTTCATTT TTAAATACAG AAGGCATAAA TATTCCAGCA

201 GACCAGCCAA TTACTAAACT TAAGAATTTA GAAGATGTTG TTGTCCCTAC

251 TATGGAAATT AAGGTAATTT GCAATTAACT CTTGATTTTT TTTAAACTAA

301 ATTTTTTTTA TTAGATTGAA CCATTTGAAA TAGTATTTTT ATGTAGGTCA

351 AAATTGGTTA AATATTGGCA AATTTCATAT GTTTCAACCT ATAATTTCTC

401 AGTATTATAT TTCCTTTGCC C
```

************************************************************

```
                    Exon 57                     (SEQ ID No:56)
  1 ATATTAGTGA ATCTTTGATG AAACAGTAGT TAAAGTTACG AGCGTGAGCC

51 ACCACACCCG GCCTAAAGTT GTAGTTCTTA ACCACTATCA CATCGTCATT

101 TGTTTCTCTG TTTAATATTA AAATTGCCAT TTATAATGTA TTGTGCTTTA

151 AGTGCAAATA GTGTATCCGA CCTATTAGCA ATCATGTTTA TACTTTTATT

201 AGGTGGACCA CACAGGAGAA TATGGAAATC TGGTGACTAT ACAGTCATTT

251 AAAGCAGAAT TTCGCTTAGC AGGAGGTGTA AATTTACCAA AAATAATAGA

301 TTGTGTAGGT TCCGATGGCA AGGAGAGGAG ACAGCTTGTT AAGGTGAGCC

351 TTCCCTTCTC TGGCTTAGCC CTTAGAGTTT TAGTGATGAA AATTTTTAGT

401 TCATATTTCT TTCTGCTTTA TTGGGGATTT GGGTCTTTAT TTGGGAATA
```

************************************************************

```
                    Exon 58                     (SEQ ID No:57)
  1 GGGAAACTTT CTAAATCAGT GTAAATGTTG TAGCTTATTC TAAATGAAAG

51 AATGGCAGTA GGTATTTAAT TATTTGGGAG ACTGTCAAGA GGTGCACAGA

101 TGCTCAGATT GGTTTGAGTG CCCTTTGCTA TTCTCAGATG ACTCTGTGTT

151 TTTATAATAA AATAAACTGT ACTTGTTTAT TCATGCTTAA TTATTCTGAA

201 GGGCCGTGAT GACCTGAGAC AAGATGCTGT CATGCAACAG GTCTTCCAGA

251 TGTGTAATAC ATTACTGCAG AGAAACACGG AAACTAGGAA GAGGAAATTA

301 ACTATCTGTA CTTATAAGGT AACTATTTGT ACTTCTGTTA GTTCACCAAA

351 AACATATAAA AGATGCCATT TGGTTGGGTG AAGTGGCTCA TGCCCATATT

401 CATAATGCTT TGGGAGGCCA AGGTGGGAGG ATTGCTTGAG GCCAGGAGTT

451 CGAGACCAGC CTCAGCAACA TAGTGAGACC CCATCTTGAC AAAAAGTTAA

501 AAAAAAAAA AAAACCAGAG
```

************************************************************

```
                    Exon 59                     (SEQ ID No:58)
  1 TTCTTTGAGC TTAAGTTTAT TTCCGATTGG TTTCCTCCAA GGAGCTTTGT

51 CTTCTATGGA CAGAGAAATA TTAATACAAC TTGAAAAAAA ATGCTTTGCA

101 CTGACTCTGA TAGCTGAATG ATCATCAAAT GCTCTTTAAT GGCCTTTTAA

151 AAGTAAAAGG TATTTAATCT GTAACTCCAG GTGGTTCCCC TCTCTCAGCG

201 AAGTGGTGTT CTTGAATGGT GCACAGGAAC TGTCCCCATT GGTGAATTTC

251 TTGTTAACAA TGAAGATGGT GCTCATAAAA GATACAGGCC AAATGATTTC

301 AGTGCCTTTC AGTGCCAAAA GAAAATGATG GTGAGTGACA CCCAAAATTA
```

TABLE 5-continued

GENOMIC ORGANIZATION
Each exon and its flanking intron sequences are listed
separately with the exon underlined. Exons are separated by a
row of ****. Example primers are in bold.

```
351 AAGGTTATTG TAAGATTATT TAATGGCTTA TTAAAGCTGA CAGCTGTCAG

401 ATATTATAGA ATACAAAAAA ACTTTAATTT CATCAGGTAA TTGTCAAAGA

451 TACTAAGTAA AAGAAAAACT CATCAGAATG AAAGTGTGTG AGTGAAAAAG

501 GAAGGATTTT AAACTACAT
```

****************************************************************

```
                 Exon 60                              (SEQ ID No:59)
  1 ATCACTTGTA ATTAATTGCT TCCCTGTCCA GACTGTTAGC TTCTTGTAGG

51 TAATGTATCC TGTTCATCTT TATTGCCCCT ATATCTGTCA TATTTTTATA

101 TAAAAATGTG TATATTAGTT TAATTGAACA CAATATTGAA AAATAATTAT

151 ATATATTCTC TATTTAAAGG AGGTGCAAAA AAAGTCTTTT GAAGAGAAAT

201 ATGAAGTCTT CATGGATGTT TGCCAAAATT TCAACCAGT TTTCCGTTAC

251 TTCTGCATGG AAAAATTCTT GGATCCAGCT ATTTGGTTTG AGAAGCGATT

301 GGCTTATACG CGCAGTGTAG CTACTTCTTC TATTGGTAAT CTTCTTGTAC

351 ATATAGTAGA TTGAGCACTT TGTTGTTTGG CAGGTTTTAT TTTTGTTTGA

401 TTCAGCACTT TTTCTACATT CTGAGTTGCA GGGGATGAT AGTGATGATG

451 TGGTTAGTAA CCATCCCATC TTCATTATTA AATCATATGT TTCTTGTTCA

501 TCCTGATTCT TAGTGTCTAC CTTTTTATAA CTTATGCAGA AGAGAATTCT
```

****************************************************************

```
                 Exon 61                              (SEQ ID No:60)
  1 AATCATCTAG GATTTGTAAA ATGCAATATG CATTAAAATA GCTGGCAAGA 51 TTTGAGTTAA ACTCaACATG GCCGGTTATG CACATCATTT AAGTAGGCTA

101 AAAATCCTAA ACTACTTAAA GATTATACCA AGTCAGTGGT CTTAATTGAA

151 ATTATGGCTA TATATTAGAA AGAGATGGAA TCAGTGATTT CAGATTGTTT

201 GTTTCTTTTT TCTCCAGTTG GTTACATACT TGGACTTGGT GATAGACATG

251 TACAGAATAT CTTGATAAAT GAGCAGTCAG CAGAACTTGT ACATATAGAT

301 CTAGGTAAGT AATAAAATCT ATGTATCTAT TCTTTTTAGT AAATATTTGG

351 TCATCATGGA ATGTTGTTTG CCTACCAAGA TATTACAAAT ATAAGAGACA

401 GATAAATCGA AGCAGTAAAT ATTGGGTTTT TTTGTTTTCA GCATAAACAG

451 TTGTCCTAGA AGAAACAGTT AACT
```

****************************************************************

```
                 Exon 62                              (SEQ ID No:61)
  1 GATTTGAGGT GGATCTCACA GACAGTGACA AAGATGAGGA AGGCAGCCAG

51 AGCAGAAGTA AACTACTGTA CATACTAGTG TTCATAGAAC GTAGGTAACA

101 TGTGGTTTCT TGCCTTTGTA AAGTTCACAT TCTAACTGGA AAGAAAGTAA

151 ATTAGCTGTC AAACCTCCTA ACTTCACTGT ATTCTTTACT TTAGGTGTTG

201 CTTTTGAACA GGGCAAAATC CTTCCTACTC CTGAGACAGT TCCTTTTAGA

251 CTCACCAGAG ATATTGTGGA TGGCATGGGC ATTACGGGTG TTGAAGGTGT

301 CTTCAGAAGG TAAGTGATAT GAAGTAAAGG AGGGAAATAA TTTTTGATGT
```

TABLE 5-continued

GENOMIC ORGANIZATION
Each exon and its flanking intron sequences are listed
separately with the exon underlined. Exons are separated by a
row of ****. Example primers are in bold.

```
351 CAAAATTACA TGGGCTGGGC ATGGTTCTTT GCACCTGTAA TCCCAGCTAC

401 TCAAGAGGCT GAAGTGGGAG GATTGTTTGA GCCCAGGAGT TTGAGTCCAG

451 CCTAGGCAAT ACAGCAAGAC CCTGTATCTA AAA
```

****************************************************************

```
                    Exon 63                     (SEQ ID No:62)
  1 TTCTTGTAAA TGCCAAGCTT GTGAAATAGT CAAATACATA TTTGTATTCA

51 TTTCAAACGT CTAATGAAAG CCCACTCTGC CAAGTATTAT GCTATTTTGA

101 GATACAGATA TGTAGATTAT TAAGCATAGG CTCAGCATAC TACACATGAG

151 AGTATACAGA TAAAGATATG TTGACAACAT TGGTGTGTAA CAAAATCCGT

201 ATTTATAATG TGTTTGACTC TAGATGCTGT GAGAAAACCA TGGAAGTGAT

251 GAGAAACTCT CAGGAAACTC TGTTAACCAT TGTAGAGGTA AAGTATTTTA

301 TAAGGAAGAC TTTATTTT
```

****************************************************************

```
                   Exons 64-65                  (SEQ ID No:63)
  1 AAGAACAGAT GTTCTCTCTG TTTAGGTCCT TCTATATGAT CCACTCTTTG

51 ACTGGACCAT GAATCCTTTG AAAGCTTTGT ATTTACAGCA GAGGCCGGAA

101 GATGAAACTG AGCTTCACCC TACTCTGAAT GCAGATGACC AAGAATGCAA

151 ACGAAATCTC AGGTGAGCAG TATTTTAAGA AGGTCCTGTT GTCAGTATTT

201 CAGATTTTCT TATTCCCAAG GCCTTTAAAC TGGTCACCTG GACTGGAACC

251 TTTGTGTTTT TGTCCTTAGT GATATTGACC AGAGTTTCGA CAAAGTAGCT

301 GAACGTGTCT TAATGAGACT ACAAGAGAAA CTGAAAGGAG TGGAAGAAGG

351 CACTGTGCTC AGTGTTGGTG GACAGGTGAA TTTGCTCATA CAGCAGGCCA

401 TAGACCCCAA AAATCTCAGC CGACTTTTCC CAGGATGGAA AGCTTGGGTG

451 TGA (stop codon) Exon 65 continues beyond the TGA stop
    codon into the 3'UTR (SEQ ID No:8)
```

****************************************************************

REFERENCES

Aicardi et al., "Ataxia-ocularmotor apraxia: A syndrome mimicking ataxia-telangiectasia" Ann. Neurol. 24:497–502 (1988).

Aksentijevitch et al., "Familial Mediterranean fever in Moroccan Jews: Demonstration of a founder effect by extended haplotype analysis" Am. J. Hum. Genet., 53:644–651 (1993).

Ambrose et al., "A physical map across chromosome 11q22-23 containing the major locus for ataxia-telangiectasia. Genomics, 21:612–619 (1994a).

Ambrose et al., 1994b. Structure and expression of the Huntington's disease gene: evidence against simple inactivation due to an expanded CAG repeat. Som. Cell Mol. Genet. 20:27–38.

Anderson and Kunkel, "The molecular and biochemical basis of Duchenne muscular dystrophy" Trends Biochem. Sci. 17:289–292 (1992).

Attree et al., "The Lowe's oculocerebrorenal syndrome gene encodes protein highly homologous to inositol polyphosphate-5-phosphatase" Nature, 358:239–242 (1992).

Ballabio et al., "Molecular heterogeneity of steroid sulfatase deficiency: a multicenter study on 57 unrelated patients, at DNA and protein levels" Genomics 4:36–40 (1989).

Barker, "A more robust, rapid alkaline denaturation sequencing method", BioTechniques, 14(2):168–169 (1993).

Barnes, 1994. PCR amplification of up to 35-kb DNA with high fidelity and high yield from lambda bacteriophage templates. Proc. Natl. Acad. Sci. 91:2216–2220.

Berger et al., "Isolation of a candidate gene for Norrie disease by positional cloning" Nature Genet. 1:199–203, (1992)

Beaudet and Tsui, "A suggested nomenclature for designating mutations" Hum. Mutat. 2:245–248 (1993).

Broughton et al., "Mutations in the xeroderma pigmentosum group D DNA repair/transcription gene in patients with trichothiodystrophy" Nature Genet. 7:189–194 (1994).

Broughton et al., "Molecular and cellular analysis of the DNA repair defect in a patient in xeroderma pigmentosum group D who has the clinical features of xeroderma pigmentosum and Cockayne's syndrome" *Am. J. Hum. Genet.* 56:167–174 (1995).

Brown et al., "Control of p70 S6 kinase by kinase activity of FRAP in vivo" Nature 377:441–446 (1995).

Buckler et al., "Exon amplification: a strategy to isolate mammalian genes based on RNA splicing" *Proc. Natl. Acad. Sci. USA*, 88:4005–4009 (1991).

Burke and Olson, "Preparation of Clone Libraries in Yeast Artificial-Chromosome Vectors" in *Methods in Enzymology*, Vol. 194, "Guide to Yeast Genetics and Molecular Biology", eds. C. Guthrie and G. Fink, Academic Press, Inc., Chap. 17, pp. 251–270 (1991).

Byrne et al., "Ataxia-without-telangiectasia" *J Neurol. Sci.* 66:307–317 (1984).

Capecchi, "Altering the genome by homologous recombination" *Science* 244:1288–1292 (1989).

Chakravarti et al., "Nonuniform recombination within the human beta-globin gene cluster" *Am. J. Hum. Genet.*, 36:1239–1258 (1984).

Chelly et al., "Isolation of a candidate gene for Menkes disease that encodes a potential heavy metal binding protein" *Nature Genet.* 3:14–19 (1993).

Cheng et al., 1994. Effective amplification of long targets from cloned inserts and human genomic DNA. Proc. Natl. Acad. Sci. 91:5695–5699.

Chessa et al., "Heterogeneity in ataxia telangiectasia: classical phenotype associated with intermediate cellular radiosensitivity" Am. J. Med. Genet. 42:741–746 (1992).

Chillon et al., "Mutations in the cystic fibrosis gene in patients with congenital absence of the vas deferens" *New Engl. J. Med.* 332:1475–1480 (1995).

Church et al., "Isolation of genes from complex sources of mammalian genomic DNA using exon amplification" *Nature Genet.* 6:98–104 (1993).

Church et al., 1994. Isolation of genes from complex sources of mammalian genomic DNA using exon amplification. Nature Genet. 6:98–94.

Collins, F. S. "Positional cloning: let's not call it reverse anymore" *Nature Genet.*, 1:3–6 (1992).

Cooper and Krawczak, *Human gene mutation*. BIOS Scientific Publishers, London (1993).

Davies et al., "Targeted alterations in yeast artificial chromosomes for inter-species gene transfer", *Nucleic Acids Research*, 20(11):2693–2698 (1992).

Derry et al., "WSP gene mutations in Wiskott-Aldrich syndrome and X-linked thrombocytopenia" *Hum. Mol. Genet.* 4:1127–1135 (1995).

Dickinson et al., "High frequency gene targeting using insertional vectors", *Human Molecular Genetics*, 2(8):1299–1302 (1993).

Dietz and Kendzior, "Maintenance of an open reading frame as an additional level of scrutiny during splice site selection" *Nature Genet.* 8:183–188 (1994).

Duyk et al., "Exon trapping: A genetic screen to identify candidate transcribed sequences in cloned mammalian genomic DNA" *Proc. Natl. Acad. Sci. USA*, 87:8995–8999 (1990).

Fiorilli et al., "Variant of ataxia-telangiectasia with low-level radiosensitivity" *Hum. Genet.* 70:274–277 (1985).

Fodor et al, "Multiplexed biochemical assays with biological chips", *Nature* 364:555–556 (1993)

Foord and Rose, 1994. Long-distance PCR. PCR Methods Appl. 3:S149–S161.

Foroud et al. "Localization of the AT locus to an 8 cM interval defined by STMY and S132"*Am. J. Hum. Genet.,* 49:1263–1279 (1991).

Friedman and Weitberg, "Ataxia without telangiectasia" Movement Disorders 8:223–226 (1993).

Frohman, M. A. "On beyond classic RACE (rapid amplification of cDNA ends)" *PCR Methods and Applications,* 4:S40–S58 (1994).

Frohman et al., "Rapid production of full-length cDNAs from rare transcripts: Amplification using a single gene-specific oligonucleotide primer" *Proc. Natl. Acad. Sci. USA,* 85:8998–9002 (1988).

Gatti et al., "Genetic haplotyping of ataxia-telangiectasia families localizes the major gene to an 850 kb region on chromosome 11q23.1" *Int. J. Radiat. Biol.* (1994).

Gatti et al. "Localization: of an ataxia-telangiectasia gene to chromosome 11q22–23" *Nature,* 336: 577–580 (1988).

Gibson et al., "A nonsense mutation and exon skipping in the Fanconi anaemia group C gene" *Hum. Mol. Genet.* 2:797–799 (1993).

Gilad et al., *Hum. Mol. Genet.* 5:433–439 (1996).

Gilboa et al. "Transfer and expression of cloned genes using retroviral vectors" *BioTechniques* 4(6):504–512 (1986).

Gottlieb and Jackson, "Protein kinases and DNA damage" *Trends Biochem. Sci.* 19:500–503 (1994).

Greenwell et al., "TEL1, a gene involved in controlling telomere length in *Saccharomyces cerevisiae*, is homologous to the human ataxia telangiectasia (ATM) gene" Cell 82:823–829 (1995).

Hastbacka et al., "Linkage disequilibrium mapping in isolated founder populations: diastrophic dysplasia in Finland" *Nature Genet.,* 2:204–211 (1992).

Harding, "Clinical features and classification of inherited ataxias" *Adv. Neurol.* 61:1–14 (1993).

Harnden, "The nature of ataxia-telangiectasia: problems and perspectives" *Int. J. Radiat. Biol.* 66:S13–S19 (1994).

Hogervorst et al., "Rapid detection of BRCA1 mutations by the protein truncation test" *Nature Genetics* 10:208–212 (1995).

Huxley et al., "The human HPRT gene on a yeast artificial chromosome is functional when transferred to mouse cells by cell fusion", *Genomics,* 9:742–750 (1991).

Jackson, 1991. A reappraisal of non-consensus mRNA splice sites. Nucleic Acids Res. 19:3795–3798.

Jakobovits et al., "Germ-line transmission and expression of a human-derived yeast artificial chromosome", *Nature* 362:255–261 (1993).

James et al., "A radiation hybrid map of 506 STS markers spanning human chromosome 11", *Nature Genet.* 8:70 (1994).

Jarvi et al., Cystic fibrosis transmembrane conductance regulator and obstructive azoospermia" *The Lancet* 345:1578 (1995).

Jaspers et al., "Genetic complementation analysis of Ataxi-aTelangiectasia and Nijmegen breakage syndrome: A survey of 50 patients", *Cytogenet. Cell Genet.,* 49:259 (1988).

Kawasaki E S. Amplification of RNA. In: PCR protocols: A Guide to Methods and Applications, Innis M A, Gelfand D H, Sninsky J J, White T J, eds. Academic Press, 1990, pp21–27.

Kerem et al., "Identification of the cystic fibrosis gene: genetic analysis" *Science,* 245:1073–1080 (1989).

Kolluri et al., "Identification of WASP mutations in patients with Wiskott-Aldrich syndrome and isolated thrombocytopenia reveals allelic heterogeneity at the WAS locus" *Hum. Mol. Genet.* 4:1119–1126 (1995).

Kozak et al., "An analysis of 5'-noncoding sequences from 699 vertebrate messenger RNAs" *Nucleic Acids Res.,* 15:8125–8148 (1987).

Lamb et al., "Introduction and expression of the 400 kilobase precursor amyloid protein gene in transgenic mice", *Nature Genetics*, 5:22–29 (1993).

Lange et al., "Localization of an ataxia-telangiectasia gene to a 850 kb interval on chromosome 11q23.1 by linkage analysis of 176 families in an international consortium" *Am. J. Hum. Genet.* 57:112–119 (1995).

Lehesjoki et al., "Localization of the EPM1 gene for progressive myoclonus epilepsy on chromosome 21: linkage disequilibrium allows high resolution mapping" *Hum. Mol. Genet.*, 2:1229–1234 (1993).

Lichter et al., "High-resolution mapping of human chromosome 11 by in situ hybridization with cosmid clones" *Science* 247:64–69 (1990).

Litt and Luty, "A hypervariable microsatellite revealed by in vitro amplification of a dinucleotide repeat within the cardiac muscle actin gene" *Am. J. Hum. Genet.*, 44:397–401 (1989).

Liu and Sommer, "Restriction endonuclease fingerprinting (REF): a sensitive method for screening mutations in long, contiguous segments of DNA" *BioTechniques* 18:470–477 (1995).

Llerena et al., "Spontaneous and induced chromosome breakage in chorionic villus samples: a cytogenetic approach to first trimester prenatal diagnosis of ataxia-telangiectasia syndrome" *J. Med. Genet.*, 26:174–178 (1989).

Lovett et al., "Direct selection: A method for the isolation of cDNA encoded by large genomic regions", *Proc. Natl. Acad. Sci. USA* 88, 9628 (1991)

Maserati et al., "Ataxia-without-telangiectasia in two sisters with rearrangements of chromosomes 7 and 14" *Clin. Genet.* 34:283–287 (1988).

McConville et al., "Genetic and physical mapping of the ataxia-telangiectasia locus on chromosome 11q22–23" *Int. J. Radiat. Biol.* (1994).

McConville et al., "Paired STSs amplified from radiation hybrids, and from associated YACs, identify highly polymorphic loci flanking the ataxia-telangiectasia locus on chromosome 11q22–23" *Hum. Mol. Genet.*, 2:969–974 (1993).

McConville et al., "Fine mapping of the chromosome 11q22–23 region using PFGE, linkage and haplotype analysis; localization of the gene for ataxia telangiectasia to a 5 cM region flanked by NCAM/DRD2 and STMY/CJ52.75, phi2.22" *Nucleic Acids Res.*, 18:4335–4343 (1990).

Miki et al. "A strong candidate for the breast and ovarian cancer susceptibility gene BRCA1" *Science*, 266:66–71 (1994).

Mitchison et al., "Fine genetic mapping of the Batten Disease locus (CLN3) by haplotype analysis and demonstration of allelic association with chromosome 16p microsatellite loci" *Genomics*, 16:455–460 (1993).

Morgan et al., "The selective isolation of novel cDNAs encoded by the regions surrounding the human interleukin 4 and 5 genes" *Nucleic Acids Res.*, 20:5173–5179 (1992).

Nehls et al., 1994a. Exon amplification from complete libraries of genomic DNA using a novel phage vector with automatic plasmid excision facility: application to the mouse neurofibromatosis-1 locus. Oncogene 9:2169–2175.

Nehls et al., 1994b. The sequence complexity of exons trapped from the mouse genome. Current Biology 4:983–989.

Orita et al. Detection of polymorphisms of human DNA by gel electrophoresis as single-strand conformation polymorphisms. Proc Natl Acad Sci USA 1989; 86:2766–2770

Oskato et al., "Ataxia-telangiectasia: allelic association with 11q22–23 markers in Moroccan-Jewish patients. 43rd *Annual Meeting of the American Society of Human Genetics*, New Orleans, La. (1993).

Ozelius et al., "Strong alleleic association between the torsion dystonia gene (DYT1) and loci on chromosome 9q34 in Ashkenazi Jews" *Am. J. Hum. Genet.* 50:619–628 (1992).

Parimoo et al., "cDNA selection: Efficient PCR approach for the selection of cDNAs encoded in large chromosomal DNA fragments" *Proc. Natl. Acad. Sci. USA*, 88:9623–9627 (1991).

Pease et al., "Light-generated oligonucleotide arrays for rapid DNA sequence analysis", *Proc. Natl. Acad. Sci. USA* 91(11):5022–5026 (1994)

Richard et al., "A radiation hybrid map of human chromosme 11q22–23 containing the Ataxia-Telangiectasia disease locus", *Genomics* 17, 1 (1993).

Roberts et al., 1993. Exon structure of the human dystrophin gene. Genomics 16:536–538.

Rothstein, "Targeting, disruption, replacement, and allele rescue: integrative DNA transformation in yeast" in *Methods in Enzymology*, Vol. 194, "Guide to Yeast Genetics and Molecular Biology", eds. C. Guthrie and G. Fink, Academic Press, Inc., Chap. 19, pp. 281–301 (1991).

Rotman et al., "Three dinucleotide repeat polymorphisms at the ataxia-telangiectasia locus" *Human Molecular Genetics* (1994b).

Rotman et al., "A YAC contig spanning the ataxia-telangiectasia locus (groups A and C) on chromosome 11q22–23. *Genomics* (1994c).

Rotman et al., "Physical and genetic mapping of the ATA/ATC locus in chromosome 11q22–23" *Int. J. Radiat. Biol.* (1994d).

Rotman et al., "Rapid identification of polymorphic CA-repeats in YAC clones" *Molecular Biotechnology* (1995).

Savitsky et al., "A single gene with homologies to phosphatidylinositol 3-kinases and rad3+ is Mutated in all complementation groups of ataxia-telangiectasia" *Science*, 268:1749–1753 (Jun. 23, 1995a)

Savitsky et al., "The complete sequence of the coding region of the ATM gene reveals similarity to cell cycle regulators in different species" *Hum. Mol. Genet.* 4:2025–2032 (1995b).

Schedl et al., "A yeast artificial chromosome covering the tyrosinase gene confers copy number-dependent expression in transgenic mice", *Nature*, 362:258–261 (1993).

Sirugo et al., "Friedreich ataxia in Louisiana Acadians: Demonstration of a founder effect by analysis of microsatellite-generated extended haplotypes" *Am. J.Hum. Genet.*, 50:559–566 (1992).

Shiloh, "Ataxia-telangiectasia: closer to unraveling the mystery" *European Journal of Human Genetics* (1995)

Shiloh et al., *Am. J. Hum. Genet.* 55 (suppl.), A49 (1994a)

Shiloh, et al., 1994b. Genetic, physical and functional analysis of the ataxia-telangiectasia locus on chromosome 11q22–23. 44th Annual Meeting of the American Society of Human Genetics, Montreal. Am. J. Hum. Genet. 55:A49.

Sommer, "Recent human germ-line mutation: Inferences from patients with hemophilia B" *Trends Gene.* 11:141–147 (1995).

Steingrimsdottir et al., "Mutations which alter splicing in the human hypoxanthine-guanine phosphoribosyl-transferase gene" *Nucleic Acids Res.* 6:1201–1208 (1992).

Strauss et al., "Germ line transmission of a yeast artificial chromosome spanning the murine $\alpha_1$ (I) collagen locus", *Science*, 259:1904–1907 (1993).

Tagle et al., "Magnetic capture of expressed sequences encoded within large genomic segments" *Nature*, 361:751–753 (1993).

Taylor et al., "Genetic and cellular features of ataxia telangiectasia" *Int. J. Radiat. Biol.* 65:65–70 (1994).

Taylor et al., Variant forms of ataxia telangiectasia. J. Med. Genet. 24, 669–677 (1987).

The European Polycystic Kidney Disease Consortium, "The polycystic kidney disease 1 gene encodes a 14 kb transcript and lies within a duplicated region on chromosome 16" *Cell,* 77:881–894 (1994).

The Huntington's Disease Collaborative Research Group, "A novel gene containing a trinucleotide repeat that is expanded and unstable on Huntington's disease chromosomes" *Cell,* 72:971–983 (1993).

Trofatter et al., "A novel moesin-, ezrin-, radixin-like gene is a candidate for the neurofibromatosis 2 tumor suppressor" *Cell,* 72:791–800 (1993).

Vanagaite et al., "Physical localization of microsatellite markers at the ataxia-telangiectasia locus at 11q22–23. *Genomics,* 22:231–233 (1994a).

Vanagaite et al., "High-density microsatellite map of ataxia-telangiectasia locus" *Human Genetics* 95:451–453 (1995).

Vetrie et al., "The gene involved in X-linked agammaglobulinemia is a member of the src family of protein-tyrosine kinases" *Nature,* 361:226–233 (1993).

Weber and May, "Abundant class of human DNA polymorphisms which can be typed using the polymerase chain reaction" *Am. J. Hum. Genet.,* 44:388–396 (1989).

Weemaes et al., "Nijmegen breakage syndrome: A progress report" *Int. J. Radiat. Biol.* 66:S185–S188 (1994).

Ying and Decoteau, "Cytogenetic anomalies in a patient with ataxia, immune deficiency, and high alpha-fetoprotein in the absence of telangiectasia" *Cancer Genet. Cytogenet.* 4:311–317 (1983).

Zakian, "ATM-related genes: What do they tell us about functions of the human gene!" *Cell* 82:685–687 (1995).

Ziv et al., "Ataxia-telangiectasia: linkage analysis in highly inbred Arab and Druze families and differentiation from an ataxia-microcephaly-cataract syndrome" *Hum. Genet.,* 88:619–626 (1992).

Ziv et al., "The ATC (ataxia-telangiectasia complementation group C) locus localizes to 11q22–q23. *Genomics,* 9:373–375 (1991).

Ziv et al., "Ataxia telangiectasia: a variant with altered in vitro phenotype of fibroblast cells" *Mutation Res.* 210:211–219 (1989).

What is claimed is:

1. A purified, isolated and cloned nucleic acid sequence encoding a ATM polypeptide containing mutations which cause ataxia-telangiectasia wherein the mutation is one set forth in Tables 2 and 3.

2. A purified, isolated and cloned nucleic acid sequence according to claim 1 where the nucleic acid is mRNA.

3. The nucleic acid sequence of claim 1 wherein mutation events are those set forth in Table 3 such that a resulting sequence is altered imparting ataxia-telangiectasia.

4. A vector comprising an expression control sequence operatively linked to the nucleic acid sequence of claim 1.

5. A host cell, wherein the host cell is selected from the group of suitable eucaryotic and procaryotic cells, which is transformed with the vector of claim 4.

6. The host cell of claim 5 wherein it is *E. coli*.

7. A kit for detecting a nucleic acid sequence encoding an ATM polypeptide of claim 1 said kit including:

a nucleic acid probe and PCR primers which specifically detect and amplify a non-mutant ATM encoding sequence, at least one nucleic acid probe and PCR primer pair which specifically detect and amplify an ATM nucleic acid sequence containing a mutation as set forth in Table 2 and 3 wherein the mutation causes ataxia-telangiectasia, and detection means for indicating the presence of the mutation.

* * * * *